(12) United States Patent
Bassaganya-Riera et al.

(10) Patent No.: US 12,281,096 B2
(45) Date of Patent: **\*Apr. 22, 2025**

(54) CRYSTALLINE FORMS OF PIPERAZINE-1,4-DIYLBIS((6-(1H-BENZO[D]IMIDAZO-2-YL)PYRIDIN-2YL)METHANONE)

(71) Applicant: NImmune Biopharma, Inc., Blacksburg, VA (US)

(72) Inventors: Josep Bassaganya-Riera, Blacksburg, VA (US); Andrew Leber, Blacksburg, VA (US); Raquel Hontecillas, Blacksburg, VA (US)

(73) Assignee: NImmune Biopharma, Inc., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/946,236

(22) Filed: Sep. 16, 2022

(65) Prior Publication Data

US 2023/0028533 A1 Jan. 26, 2023

Related U.S. Application Data

(63) Continuation of application No. 17/517,184, filed on Nov. 2, 2021, now Pat. No. 11,492,342.

(60) Provisional application No. 63/108,958, filed on Nov. 3, 2020.

(51) Int. Cl.
*A61K 31/497* (2006.01)
*C07D 401/14* (2006.01)

(52) U.S. Cl.
CPC .......... *C07D 401/14* (2013.01); *A61K 31/497* (2013.01); *C07B 2200/13* (2013.01)

(58) Field of Classification Search
CPC .................................................. A61K 31/497
See application file for complete search history.

(56) References Cited

U.S. PATENT DOCUMENTS

| | | |
|---|---|---|
| 7,994,364 B2 | 8/2011 | Fischer |
| 8,372,995 B2 | 2/2013 | Krishnan |
| 8,513,224 B2 | 8/2013 | Hotter |
| 9,556,146 B2 | 1/2017 | Bassaganya-Riera |
| 9,839,635 B2 | 12/2017 | Bassaganya-Riera |
| 10,028,950 B2 | 7/2018 | Bassaganya-Riera |
| 10,201,538 B2 | 2/2019 | Bassaganya-Riera |
| 10,493,072 B2 | 12/2019 | Bassaganya-Riera |
| 10,537,565 B2 | 1/2020 | Hurter |
| 10,682,349 B2 | 6/2020 | Bassaganya-Riera |
| 10,849,895 B2 | 12/2020 | Bassaganya-Riera |
| 11,197,891 B2 | 12/2021 | Bassaganya-Riera |
| 2019/0160100 A1 | 5/2019 | Bassaganya-Riera et al. |

FOREIGN PATENT DOCUMENTS

| | | |
|---|---|---|
| CA | 2609875 C | 1/2014 |
| EP | 3243824 A1 | 11/2017 |
| GB | 2523089 A | 8/2015 |
| WO | WO 2016/064445 A1 | 4/2016 |
| WO | WO 2019/108418 A1 | 6/2019 |

OTHER PUBLICATIONS

International Search Report and Written Opinion for PCT/US2021/057706 dated Feb. 3, 2022.
Bissel P, Boes K, Hinckley J, Jortner BS, Magnin-Bissel G, Werre SR, Ehrich M, Carbo A, Philipson C, Hontecillas R, Philipson N, Gandour RD, Bassaganya-Riera J. Exploratory Studies With BT-11: A Proposed Orally Active Therapeutic for Crohn's Disease. *Int J Toxicol*. Sep. 2016;35(5):521-9.
Carbo A, Gandour RD, Hontecillas R, Philipson N, Uren A, Bassaganya-Riera J. An N,N-Bis(benzimidazolylpicolinoyl)piperazine (BT-11): A Novel Lanthionine Synthetase C-Like 2-Based Therapeutic for Inflammatory Bowel Disease. *J Med Chem*. Nov. 23, 2016;59(22):10113-10126.
Leber A, Hontecillas R, Zoccoli-Rodriguez V, Bassaganya-Riera J. Activation of LANCL2 by BT-11 Ameliorates IBD by Supporting Regulatory T Cell Stability Through Immunometabolic Mechanisms. *Inflamm Bowel Dis*. Aug. 16, 2018;24(9):1978-1991.
Leber A, Hontecillas R, Zoccoli-Rodriguez V, Ehrich M, Davis J, Chauhan J, Bassaganya-Riera J. Nonclinical Toxicology and Toxicokinetic Profile of an Oral Lanthionine Synthetase C-Like 2 (LANCL2) Agonist, BT-11. *Int J Toxicol*. Mar./Apr. 2019;38(2):96-109.
Leber A, Hontecillas R, Zoccoli-Rodriguez V, Chauhan J, Bassaganya-Riera J. Oral Treatment with BT-11 Ameliorates Inflammatory Bowel Disease by Enhancing Regulatory T Cell Responses in the Gut. *J Immunol*. Apr. 1, 2019;202(7):2095-2104.
Leber A, Hontecillas R, Zoccoli-Rodriguez V, Colombel JF, Chauhan J, Ehrich M, Farinola N, Bassaganya-Riera J. The Safety, Tolerability, and Pharmacokinetics Profile of BT-11, an Oral, Gut-Restricted Lanthionine Synthetase C-Like 2 Agonist Investigational New Drug for Inflammatory Bowel Disease: A Randomized, Double-Blind, Placebo-Controlled Phase I Clinical Trial. *Inflamm Bowel Dis*. Mar. 4, 2020;26(4):643-652.
Remington's Pharmaceutical Sciences, Sixteenth Edition, E, W. Martin (Mack Publishing Co., Easton, Pa., 1980. (Book).
Stephenson, G. A; Stowell, J. G; Toma, P. H; Dorman, D. E.; Greene, J. R.; Byrne, S. R.; "Solid state analysis of polymorphic, isomorphic and solvated forms of Dirithromycin", *J. Am. Chem. Soc*., 1994,116, 5766.

*Primary Examiner* — Brian E McDowell
(74) *Attorney, Agent, or Firm* — Daniel A. Blasiole; DeWitt LLP

(57) ABSTRACT

Crystalline forms of piperazine-1,4-diylbis((6-(1H-benzo[d]imidazo-2-yl)pyridine-2-yl)methanone), compositions containing one or more crystalline forms of piperazine-1,4-diylbis((6-(1H-benzo[d]imidazo-2-yl)pyridine-2-yl)methanone), processes for preparing crystalline forms of piperazine-1,4-diylbis((6-(1H-benzo[d]imidazo-2-yl)pyridine-2-yl)methanone), and methods of using crystalline forms of piperazine-1,4-diylbis((6-(1H-benzo[d]imidazo-2-yl)pyridine-2-yl)methanone).

16 Claims, 48 Drawing Sheets

CRYSTALLINE FORMS OF PIPERAZINE-1,4-DIYLBIS((6-(1H-BENZO[D]IMIDAZO-2-YL)PYRIDIN-2YL)METHANONE)

FIELD OF THE INVENTION

The present invention is directed to crystalline forms of piperazine-1,4-diylbis((6-(1H-benzo[d]imidazo-2-yl)pyridine-2-yl)methanone), compositions containing one or more crystalline forms of piperazine-1,4-diylbis((6-(1H-benzo[d]imidazo-2-yl)pyridine-2-yl)methanone), processes for preparing crystalline forms of piperazine-1,4-diylbis((6-(1H-benzo[d]imidazo-2-yl)pyridine-2-yl)methanone), and methods of using crystalline forms of piperazine-1,4-diylbis((6-(1H-benzo[d]imidazo-2-yl)pyridine-2-yl)methanone).

BACKGROUND

Piperazine-1,4-diylbis((6-(1H-benzo[d]imidazo-2-yl)pyridine-2-yl)methanone) (omilancor) is a small molecule that targets lanthionine synthetase C-like 2 (LANCL2). LANCL2 is a receptor expressed in mammalian cells that has been connected to immune and metabolic responses. LANCL2 has been shown to be differentially expressed in regulatory CD4+ T cells and supports the suppressive capacity of these cells. As such, LANCL2 is a therapeutic target linked to the promotion of anti-inflammatory responses and restoration of immune tolerance. LANCL2 has particular importance in the field of autoimmune and chronic inflammatory disease. The activation of LANCL2 has also been connected to improved systemic glycemic control and insulin sensitivity and altered metabolic processes within immune cells.

Piperazine-1,4-diylbis((6-(1H-benzo[d]imidazo-2-yl)pyridine-2-yl)methanone) has been studied in the context of inflammatory bowel disease and colitis. When orally administered, piperazine-1,4-diylbis((6-(1H-benzo[d]imidazo-2-yl)pyridine-2-yl)methanone) is poorly systemically absorbed, allowing for high concentrations of drug in the targeted local environment without generating high systemic exposures. In mice, piperazine-1,4-diylbis((6-(1H-benzo[d]imidazo-2-yl)pyridine-2-yl)methanone) reduces local TNFα production in the gastrointestinal tract and fecal calprotectin levels, two key biomarkers of response in IBD. In murine and human cells, piperazine-1,4-diylbis((6-(1H-benzo[d]imidazo-2-yl)pyridine-2-yl)methanone) induces changes in CD25/STAT5 signaling and late-stage glycolysis to support the differentiation of Tregs and the maintenance of Treg phenotype.

Modulation of the crystal form of piperazine-1,4-diylbis((6-(1H-benzo[d]imidazo-2-yl)pyridine-2-yl)methanone) has the potential to improve purity, obtain reproducible particle size, and finely tune the pharmacokinetic profile to provide adequate levels of piperazine-1,4-diylbis((6-(1H-benzo[d]imidazo-2-yl)pyridine-2-yl)methanone) to the target site for the treatment of diseases such as including chronic inflammatory, immune-mediated, and autoimmune diseases.

There is a need for stable crystal forms of piperazine-1,4-diylbis((6-(1H-benzo[d]imidazo-2-yl)pyridine-2-yl)methanone).

SUMMARY OF THE INVENTION

The present invention is directed to crystalline forms of piperazine-1,4-diylbis((6-(1H-benzo[d]imidazo-2-yl)pyridine-2-yl)methanone). The invention is also directed to compositions, including pharmaceutical compositions, containing one or more crystalline forms of piperazine-1,4-diylbis((6-(1H-benzo[d]imidazo-2-yl)pyridine-2-yl)methanone). The invention is further directed to processes for preparing crystalline forms of piperazine-1,4-diylbis((6-(1H-benzo[d]imidazo-2-yl)pyridine-2-yl)methanone). The invention is further directed to methods of using the crystalline forms of piperazine-1,4-diylbis((6-(1H-benzo[d]imidazo-2-yl)pyridine-2-yl)methanone), such as in the therapeutic treatment of disease.

The objects and advantages of the invention will appear more fully from the following detailed description of the preferred embodiment of the invention made in conjunction with the accompanying drawings.

DETAILED DESCRIPTION OF THE INVENTION

Figure 1:
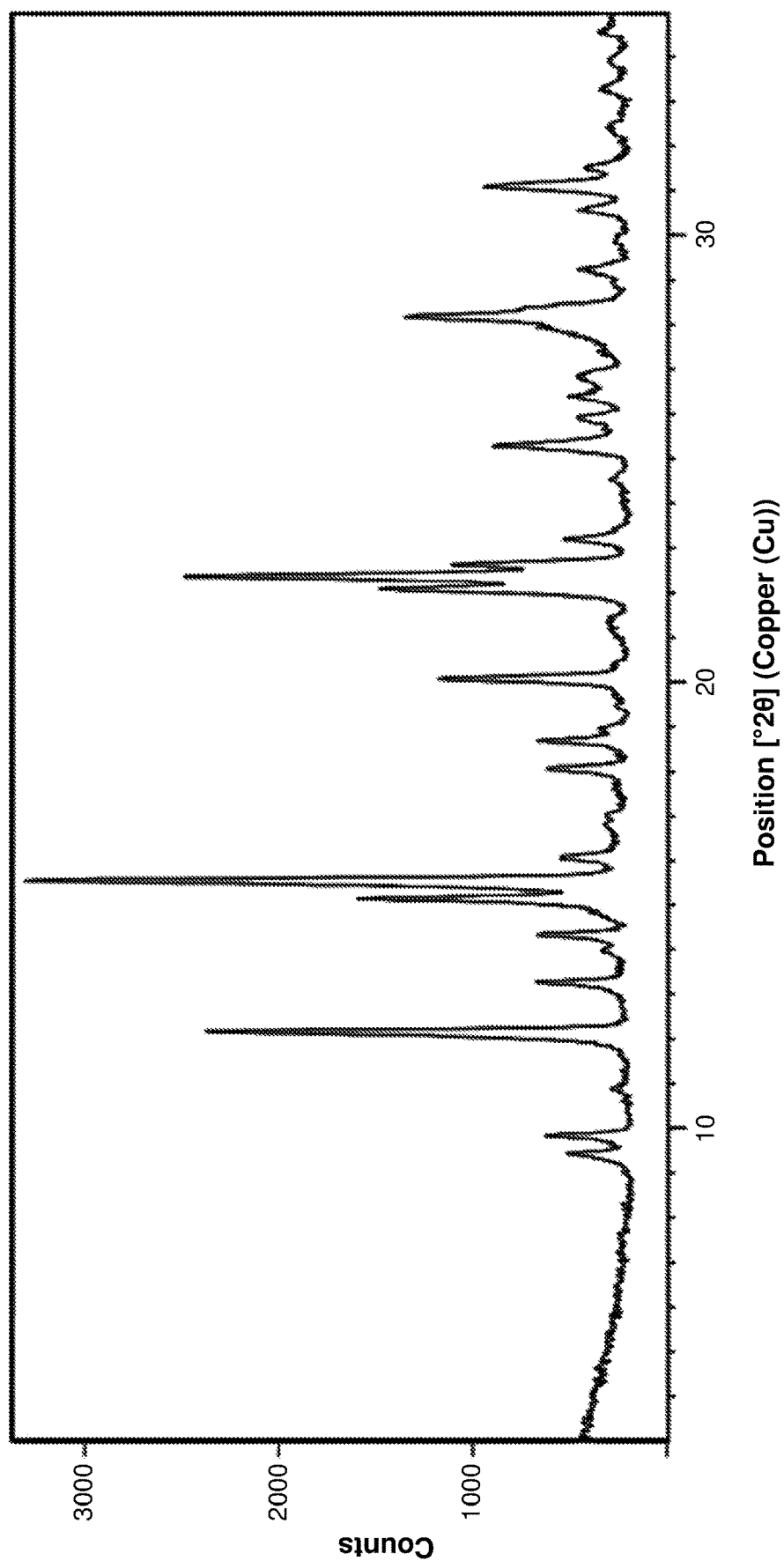
FIG. 1. X-ray powder diffraction (XRPD) graph displaying a 2θ diffractogram of piperazine-1,4-diylbis((6-(1H-benzo[d]imidazo-2-yl)pyridine-2-yl)methanone) (BT-11) free base (Form 0).

The invention provides various forms of piperazine-1,4-diylbis((6-(1H-benzo[d]imidazo-2-yl)pyridine-2-yl)methanone). The general term "piperazine-1,4-diylbis((6-(1H-benzo[d]imidazo-2-yl)pyridine-2-yl)methanone)" encompasses any form thereof, including any salt, hydrate, solvate, free acid form, free base form, crystalline form, co-crystalline form, amorphous form, or polymorph thereof. An exemplary free base form of piperazine-1,4-diylbis((6-(1H-benzo[d]imidazo-2-yl)pyridine-2-yl)methanone) has the following structure:

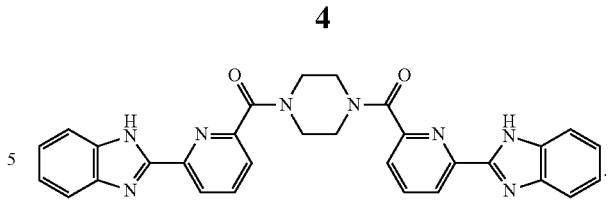

An exemplary dihydrochloride form of piperazine-1,4-diylbis((6-(1H-benzo[d]imidazo-2-yl)pyridine-2-yl)methanone) has the following structure:

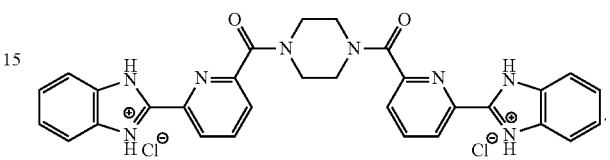

Piperazine-1,4-diylbis((6-(1H-benzo[d]imidazo-2-yl)pyridine-2-yl)methanone) is also referred to herein as "BT-11," consistent with the current literature. See U.S. Pat. No. 9,556,146 to Bassaganya-Riera et al.; U.S. Pat. No. 9,839,635 to Bassaganya-Riera et al.; U.S. Pat. No. 10,028,950 to Bassaganya-Riera et al.; U.S. Pat. No. 10,201,538 to Bassaganya-Riera et al.; U.S. Pat. No. 10,493,072 to Bassaganya-Riera et al.; U.S. Pat. No. 10,682,349 to Bassaganya-Riera et al.; U.S. Pat. No. 10,849,895 to Bassaganya-Riera et al; US 2019/0160100 A1 to Bassaganya-Riera et al.; Bissel et al. 2016 (Bissel P, Boes K, Hinckley J, Jortner B S, Magnin-Bissel G, Werre S R, Ehrich M, Carbo A, Philipson C, Hontecillas R, Philipson N, Gandour R D, Bassaganya-Riera J. Exploratory Studies With BT-11: A Proposed Orally Active Therapeutic for Crohn's Disease. *Int. J Toxicol.* 2016 September; 35(5):521-9); and Carbo et al. 2016 (Carbo A, Gandour R D, Hontecillas R, Philipson N, Uren A, Bassaganya-Riera J. An N,N-Bis(benzimidazolylpicolinoyl)piperazine (BT-11): A Novel Lanthionine Synthetase C-Like 2-Based Therapeutic for Inflammatory Bowel Disease. *J Med Chem.* 2016 Nov. 23; 59(22):10113-10126); Leber et al. 2018 (Leber A, Hontecillas R, Zoccoli-Rodriguez V, Bassaganya-Riera J. Activation of LANCL2 by BT-11 Ameliorates IBD by Supporting Regulatory T Cell Stability Through Immunometabolic Mechanisms. *Inflamm Bowel Dis.* 2018 Aug. 16; 24(9):1978-1991); Leber et al. 2019 *Int J Toxicol.* (Leber A, Hontecillas R, Zoccoli-Rodriguez V, Ehrich M, Davis J, Chauhan J, Bassaganya-Riera J. Nonclinical Toxicology and Toxicokinetic Profile of an Oral Lanthionine Synthetase C-Like 2 (LANCL2) Agonist, BT-11. *Int J Toxicol.* 2019 March/April; 38(2):96-109); Leber et al. 2019 *J Immunol.* (Leber A, Hontecillas R, Zoccoli-Rodriguez V, Chauhan J, Bassaganya-Riera. J. Oral Treatment with BT-11 Ameliorates Inflammatory Bowel Disease by Enhancing Regulatory T Cell Responses in the Gut. *J. Immunol.* 2019 Apr. 1; 202(7):2095-21104); and Leber et al 2020 (Leber A, Hontecillas R, Zoccoli-Rodriguez V, Colombel J F, Chauhan J, Ehrich M, Farinola N, Bassaganya-Riera J. The Safety, Tolerability, and Pharmacokinetics Profile of BT-11, an Oral, Gut-Restricted Lanthionine Synthetase C-Like 2 Agonist Investigational New Drug for Inflammatory Bowel Disease: A Randomized, Double-Blind, Placebo-Controlled Phase I Clinical Trial. *Inflamm Bowel Dis.* 2020 Mar. 4; 26(4):643-652).

The invention particularly provides various crystalline forms of piperazine-1,4-diylbis((6-(1H-benzo[d]imidazo-2-yl)pyridine-2-yl)methanone). Exemplary crystalline forms of piperazine-1,4-diylbis((6-(1H-benzo[d]imidazo-2-yl) pyridine-2-yl)methanone) provided herein include Form 0, Form 1, Form 2, Form 3, Form 4, Form 5, Form 6, Form 7, Form 8, Form 9, Form 10, Form 11, Form 12, and Form 13.

Crystalline compounds are solids with ordered arrays of molecules, whereas amorphous compounds are composed of disordered molecules. These arrays are also termed crystal lattices and are composed of repeating structural segments called unit cells. When the same molecule, such as an organic molecule, can order itself in a solid in more than one way, that molecule exhibits what is called polymorphism. For example, the element carbon exhibits polymorphism (in elements it is termed allotropism). Solid carbon exists in at least three known crystalline forms: graphite, diamond, and fullerenes. Although each crystalline form is carbon, each has different properties because the solid-state structure of each form differs. For example, whereas diamond is one of the hardest substances known, graphite is extremely soft. Many organic compounds are also known to be polymorphic in that their structures differ in how they pack together to form crystalline solids. See e.g., Stephenson, G. A; Stowell, J. G; Toma, P. H; Dorman, D. E.; Greene, J. R.; Byrne, S. R.; "Solid state analysis of polymorphic, isomorphic and solvated forms of Dirithromycin", *J. Am. Chem. Soc.,* 1994, 116, 5766.

Based on a chemical structure, which is the chemical connectivity of atoms to make a molecule, one cannot predict with any degree of certainty whether a compound will crystallize, under what conditions it will crystallize, how many crystalline forms of the compound might exist, or the solid-state structure of any of those forms. The term "solid-state structure" as used herein means the structure obtained when molecules pack together to form a solid.

Sometimes solvent or water molecules become incorporated into the crystal lattice of a crystalline solid. Such a crystalline solid may be referred to as a solvate or hydrate, respectively. Solvates, hydrates, and polymorphs are often called crystalline forms or crystalline solid forms. Here, as in most of the solid-state chemical arts, weakly bound solvates and hydrates are also included as crystalline forms where the solvent or water molecules are in channels or not incorporated into the crystal lattice. Amorphous forms are often referred to as solid forms, but they are not crystalline solid forms.

Different crystalline forms of the same compound often possess different solid-state properties such as melting point, solubility, handling, and stability. Thus, once different crystalline forms of the same compound have been identified, the optimum crystalline form under any given set of processing and manufacturing conditions may be determined as well as the different solid-state properties of each crystalline form.

There are a number of analytical methods one of ordinary skill in the art in solid-state chemistry can use to analyze solid forms. The term "analyze" as used herein means to obtain information about the solid-state structure of solid forms. For example, X-ray powder diffraction is a suitable technique for differentiating amorphous forms from crystalline forms and for characterizing and identifying crystalline forms of a compound. X-ray powder diffraction is also suitable for quantifying the amount of a crystalline form (or forms) in a mixture. In X-ray powder diffraction, X-rays are directed onto a crystal and the intensity of the diffracted X-rays is measured as a function of twice the angle between the X-ray source and the beam diffracted by the sample. The intensity of these diffracted X-rays can be plotted on a graph as peaks with the x-axis being twice the angle (this is known as the "2θ" angle) between the X-ray source and the diffracted X-rays and with the y-axis being peak intensity of the diffracted X-rays. This graph is called an X-ray powder diffraction pattern or powder pattern. Different crystalline forms exhibit different powder patterns because the location of the peaks on the x-axis is a property of the solid-state structure of the crystal.

Such powder patterns, or portions thereof, can be used as an identifying fingerprint for a crystalline form. Thus, one could take a powder pattern of an unknown sample and compare that powder pattern with a reference powder pattern. A positive match would mean that the unknown sample is of the same crystalline form as that of the reference. One could also analyze an unknown sample containing a mixture of solid forms by adding and subtracting powder patterns of known compounds.

When selecting peaks in a powder pattern to characterize a crystalline form or when using a reference powder pattern to identify a form, one identifies a peak or collection of peaks in one form that are not present in the other solid forms.

The term "characterize" as used herein means to select an appropriate set of data capable of distinguishing one solid form from another. That set of data in X-ray powder diffraction is the position of one or more peaks. Selecting which piperazine-1,4-diylbis((6-(1H-benzo[d]imidazo-2-yl) pyridine-2-yl)methanone) X-ray powder diffraction peaks define a particular form is said to characterize that form.

The term "identify" as used herein means taking a selection of characteristic data for a solid form and using those data to determine whether that form is present in a sample. In X-ray powder diffraction, those data are the x-axis positions of the one or more peaks characterizing the form in question as discussed above. For example, once one determines that a select number of X-ray diffraction peaks characterize a particular solid form of piperazine-1,4-diylbis ((6-(1H-benzo[d]imidazo-2-yl)pyridine-2-yl)methanone), one can use those peaks to determine whether that form is present in a sample containing piperazine-1,4-diylbis((6- (1H-benzo[d]imidazo-2-yl)pyridine-2-yl)methanone).

When characterizing and/or identifying crystalline forms of the same chemical compound with X-ray powder diffraction, it is often not necessary to use the entire powder pattern. A smaller subset of the entire powder pattern can often be used to perform the characterization and/or identification. By selecting a collection of peaks that differentiate the crystalline form from other crystalline forms of the compound, one can rely on those peaks to both characterize the form and to identify the form in, for example, an unknown mixture. Additional data can be added, such as from another analytical technique or additional peaks from the powder pattern, to characterize and/or identify the form.

Due to differences in instruments, samples, and sample preparation, peak values can be reported with the modifier "about" in front of the peak values. This is common practice in the solid-state chemical arts because of the variation inherent in peak values. A typical precision of the 2θ x-axis value of a peak in a powder pattern is on the order of plus or minus 0.2° 2θ. Thus, a powder diffraction peak that appears at "about 9.2° 2θ," means that the peak could be between 9.0° 2θ and 9.4° 2θ when measured on most X-ray diffractometers under most conditions. Variability in peak intensity is a result of how individual crystals are oriented in the sample container with respect to the external X-ray source (known as "preferred orientation"). This orientation effect does not provide structural information about the crystal.

X-ray powder diffraction is just one of several analytical techniques one may use to characterize and/or identify crystalline forms. Spectroscopic techniques such as Raman (including microscopic Raman), infrared, and solid-state NMR spectroscopies may be used to characterize and/or identify crystalline forms. These techniques may also be used to quantify the amount of one or more crystalline forms in a mixture.

Thermal techniques such as melting point do not necessarily, in and of themselves, characterize and/or identify different crystalline forms of a compound because it is possible that different crystalline forms of the same compound would have indistinguishable melting points. In such circumstances, however, melting points could be used together with another analytical method, such as X-ray powder diffraction, to characterize and/or identify crystalline forms.

The entire X-ray powder diffraction may be used to characterize each crystalline form of piperazine-1,4-diylbis((6-(1H-benzo[d]imidazo-2-yl)pyridine-2-yl)methanone), however, one may select a smaller subset of peaks in each pattern to characterize each crystalline form of piperazine-1,4-diylbis((6-(1H-benzo[d]imidazo-2-yl)pyridine-2-yl)methanone). Those selected peaks may then be used to identify the presence of particular crystalline forms of piperazine-1,4-diylbis((6-(1H-benzo[d]imidazo-2-yl)pyridine-2-yl)methanone) in an unknown sample of or containing piperazine-1,4-diylbis((6-(1H-benzo[d]imidazo-2-yl)pyridine-2-yl)methanone).

Various methods of characterizing crystalline forms are provided by U.S. Pat. Nos. 8,372,995 and 10,537,565, each of which is incorporated herein by reference.

An aspect of the invention is directed to a crystal form of piperazine-1,4-diylbis((6-(1H-benzo[d]imidazo-2-yl)pyridine-2-yl)methanone) having a peak within at least one, at least two, at least three, at least four, at least five, or each 2θ value range(s) selected from 12.4 to 12.8, 16.9 to 17.3, 20.5 to 20.9, 22.1 to 22.5, 23.2 to 23.6, and 28.2 to 28.6 degrees in an X-ray powder diffraction pattern obtained using Cu K alpha radiation. In some versions, the crystal form of piperazine-1,4-diylbis((6-(1H-benzo[d]imidazo-2-yl)pyridine-2-yl)methanone) has a peak within one or both 2θ value range(s) selected from 12.4 to 12.8 and 16.9 to 17.3. In some versions, the crystal form of piperazine-1,4-diylbis((6-(1H-benzo[d]imidazo-2-yl)pyridine-2-yl)methanone) has a peak within a 2θ value range of 12.4 to 12.8 degrees. In some versions, the crystal form of piperazine-1,4-diylbis((6-(1H-benzo[d]imidazo-2-yl)pyridine-2-yl)methanone) has a peak within a 2θ value range of 16.9 to 17.3 degrees. In some versions, the crystal form of piperazine-1,4-diylbis((6-(1H-benzo[d]imidazo-2-yl)pyridine-2-yl)methanone) has a peak within at least one, at least two, at least three, or each 2θ value range(s) selected from 20.5 to 20.9, 22.1 to 22.5, 23.2 to 23.6, and 28.2 to 28.6 degrees. In some versions, the crystal form of piperazine-1,4-diylbis((6-(1H-benzo[d]imidazo-2-yl)pyridine-2-yl)methanone) further has a peak within a 2θ value range of 9.8 to 10.2 degrees. In some versions, the crystal form of piperazine-1,4-diylbis((6-(1H-benzo[d]imidazo-2-yl)pyridine-2-yl)methanone) further has a peak within a 2θ value range of 14.1 to 14.5 degrees. In some versions, the crystal form of piperazine-1,4-diylbis((6-(1H-benzo[d]imidazo-2-yl)pyridine-2-yl)methanone) further has a peak within a 2θ value range of 19.2 to 19.6 degrees. In some versions, the crystal form of piperazine-1,4-diylbis((6-(1H-benzo[d]imidazo-2-yl)pyridine-2-yl)methanone) further has a peak within a 2θ value range of 25.3 to 25.7 degrees. An exemplary crystal form of piperazine-1,4-diylbis((6-(1H-benzo[d]imidazo-2-yl)pyridine-2-yl)methanone) having these characteristics is provided herein as Form 2.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to any pattern provided in any one of FIGS. 11, 12, 13, 14A, and 14B. "Substantially similar" in this context and other similar contexts herein refers to an X-ray powder diffraction pattern having peaks at about the same 2θ values as the peaks present in the patterns provided herein, wherein "about" refers to a value of plus or minus 0.2° 2θ. An exemplary crystal form of piperazine-1,4-diylbis((6-(1H-benzo[d]imidazo-2-yl)pyridine-2-yl)methanone) having these characteristics is provided herein as Form 2.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 5. An exemplary crystal form of piperazine-1,4-diylbis((6-(1H-benzo[d]imidazo-2-yl)pyridine-2-yl)methanone) having these characteristics is provided herein as Form 2.

An aspect of the invention is directed to a crystal form of piperazine-1,4-diylbis((6-(1H-benzo[d]imidazo-2-yl)pyridine-2-yl)methanone) with the unit cell dimensions a=12.81 Å, α=90°, b=12.56 Å, β=105.25°, c=9.48 Å, γ=90°. An exemplary crystal form of piperazine-1,4-diylbis((6-(1H-benzo[d]imidazo-2-yl)pyridine-2-yl)methanone) having these characteristics is provided herein as Form 2.

Figure 3:
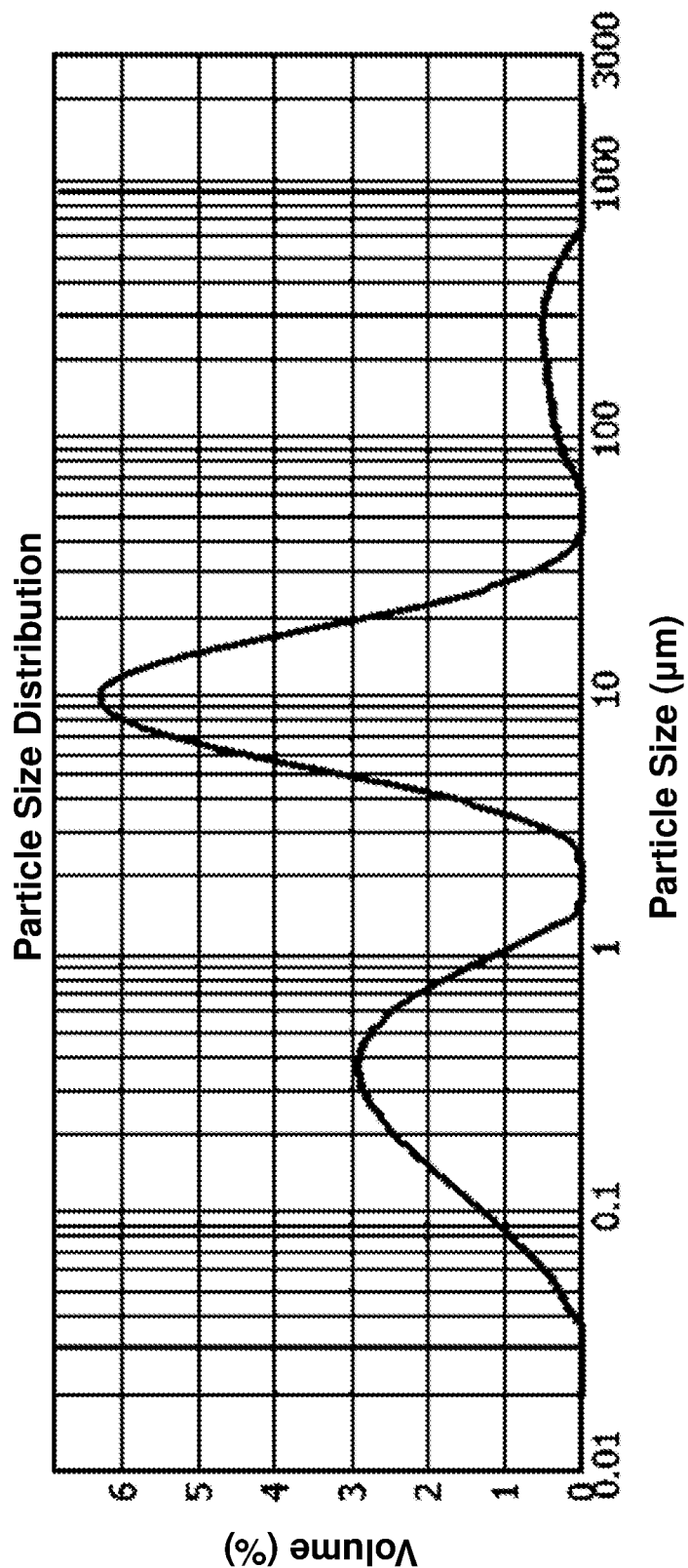
FIG. 3. Power spectral density (PSD) graph of volume percentage versus particle size of BT-11 free base Form 0
Figure 10:
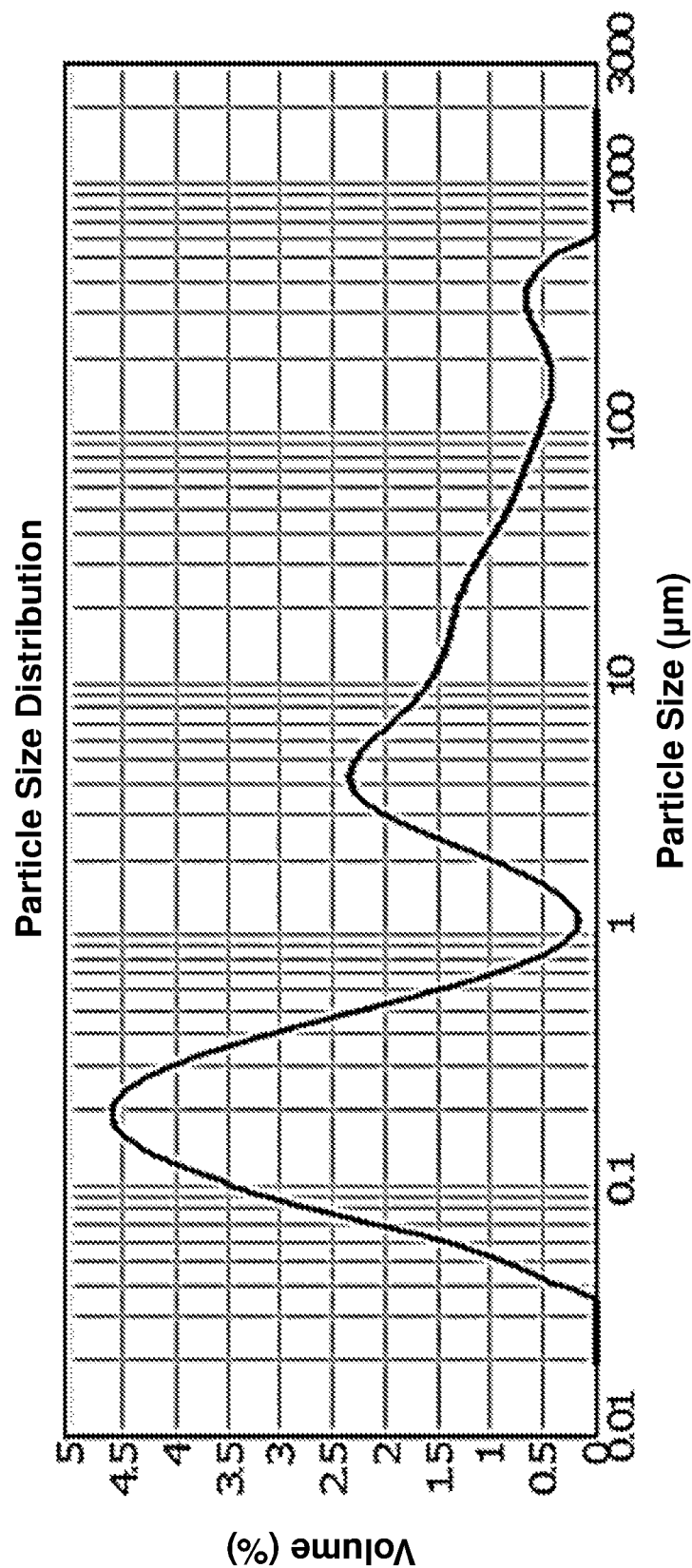
FIG. 10. PSD graph of volume percentage versus particle size for BT-11 dihydrochloride Form 1.
Figure 11:
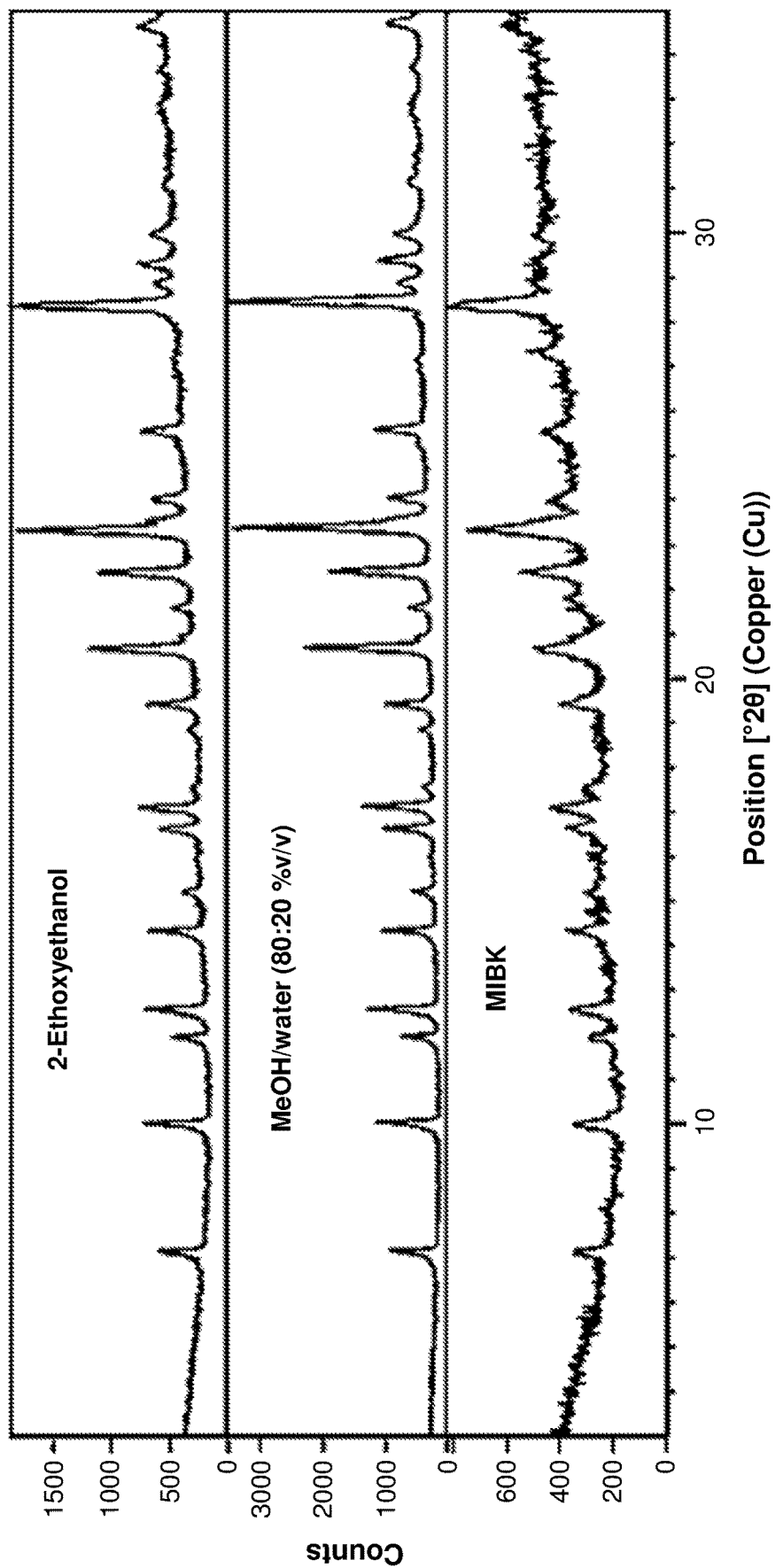
FIG. 11. XRPD 2θ diffractograms of BT-11 dihydrochloride Form 2 produced from Methods I, II, and III.
Figure 12:
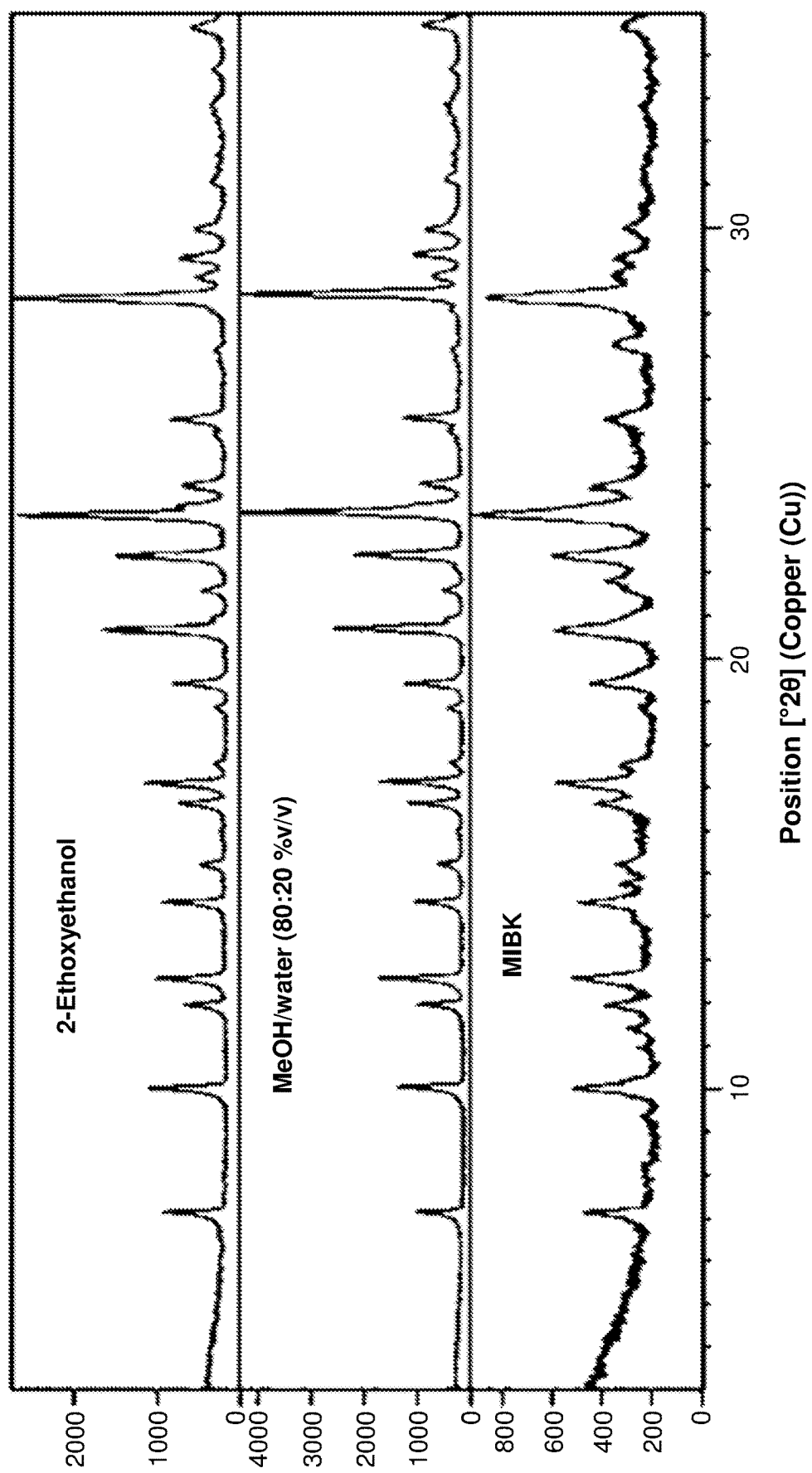
FIG. 12. Post-drying XRPD 2θ diffractograms of BT-11 dihydrochloride Form 2 produced from Methods IV and V.
Figure 13:
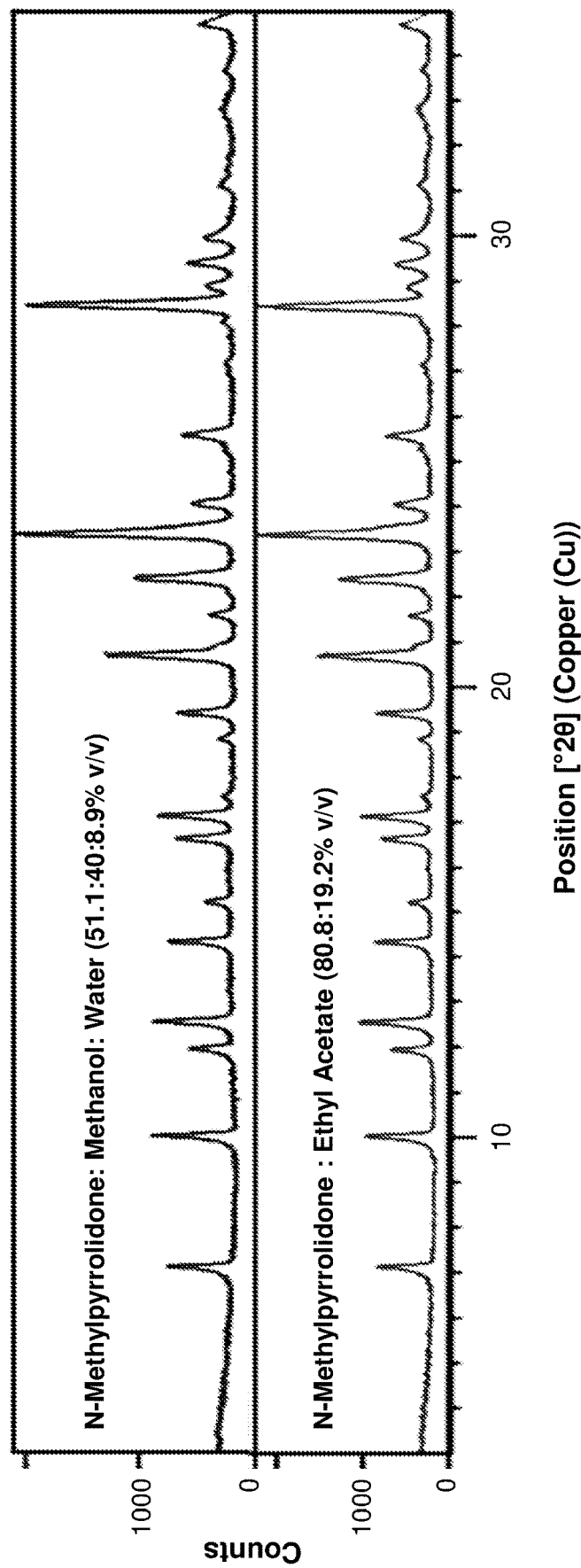
FIG. 13. XRPD 2θ diffractogram of BT-11 dihydrochloride Form 2 produced upon slurrying BT-11 free base in NMP:methanol:water (51:40:9) or NMP:ethyl acetate (81:19).
Figure 14A:
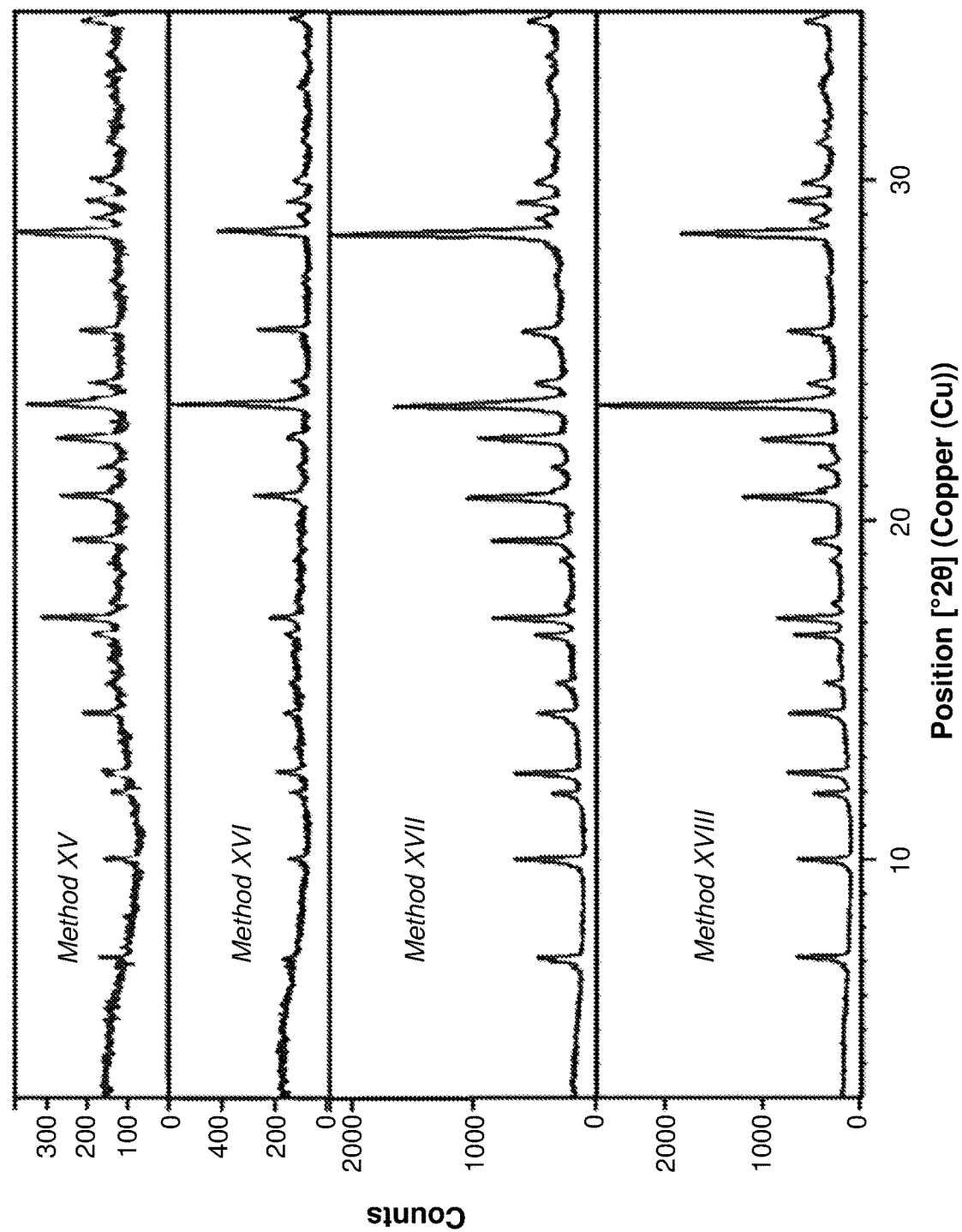
FIG. 14A and FIG. 14B. XRPD diffractograms for BT-11 dihydrochloride Form 2 produced from Methods XV, XVI, XVII, XVIII, XIX, XX, XXI, and XXII.
Figure 14B:
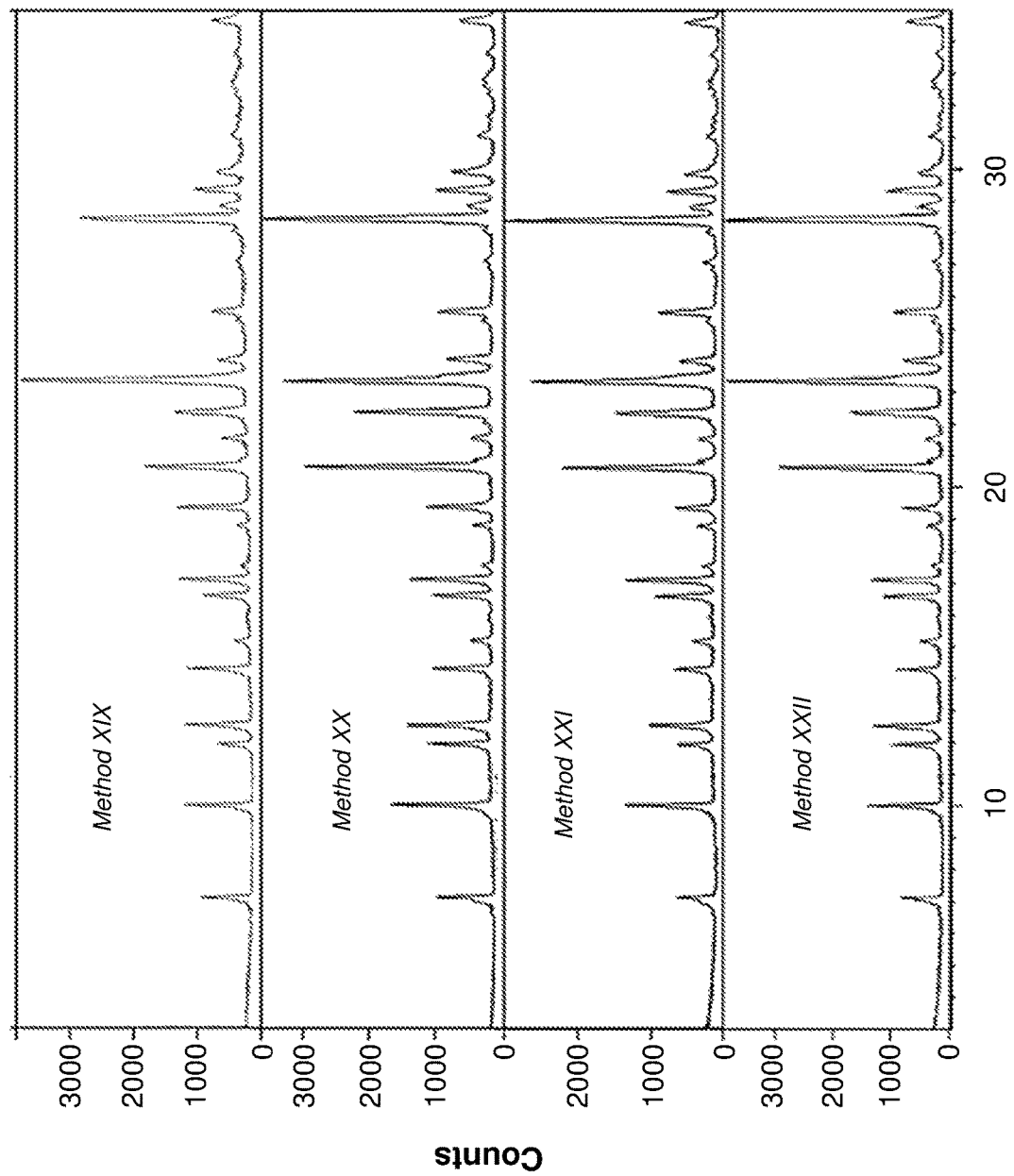
Figure 20:
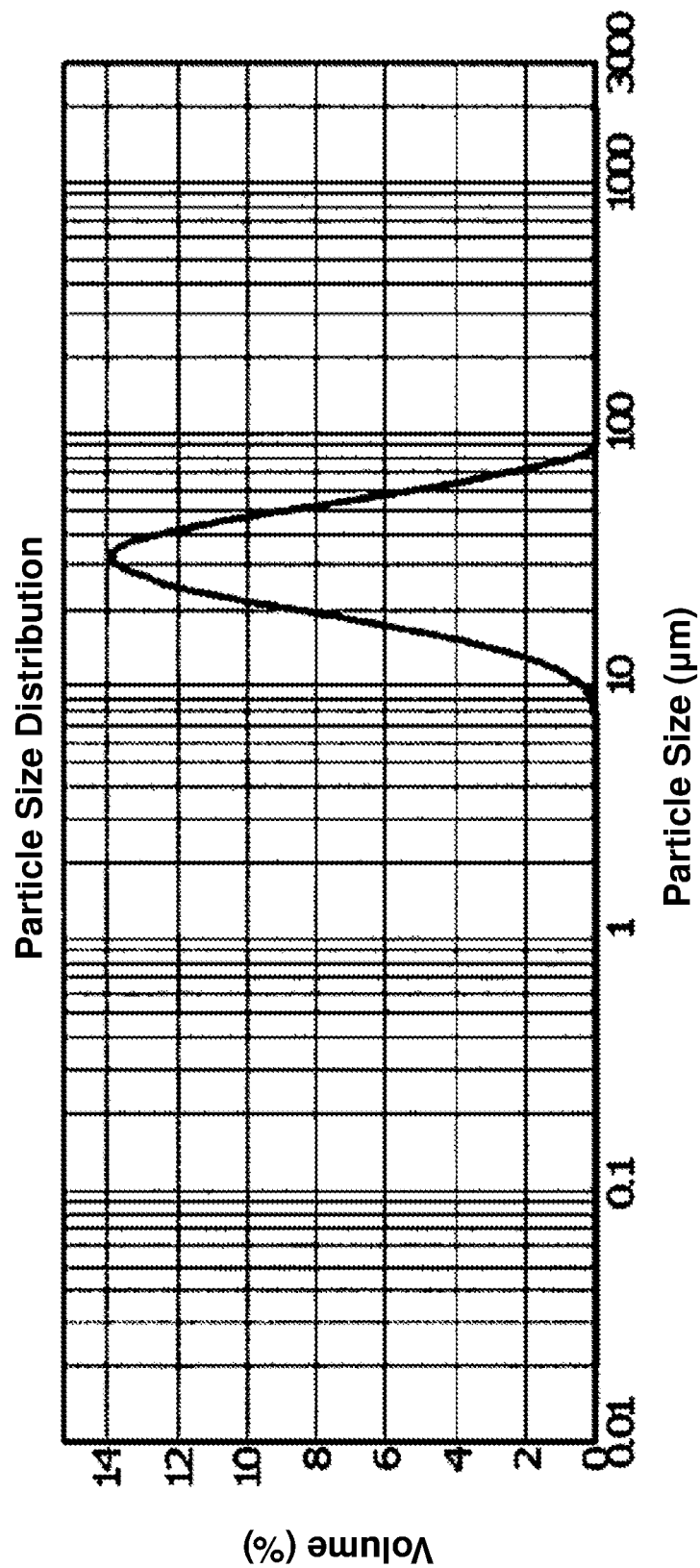
FIG. 20. PSD graph of volume percentage versus particle size for BT-11 dihydrochloride Form 2.
Figure 21A:
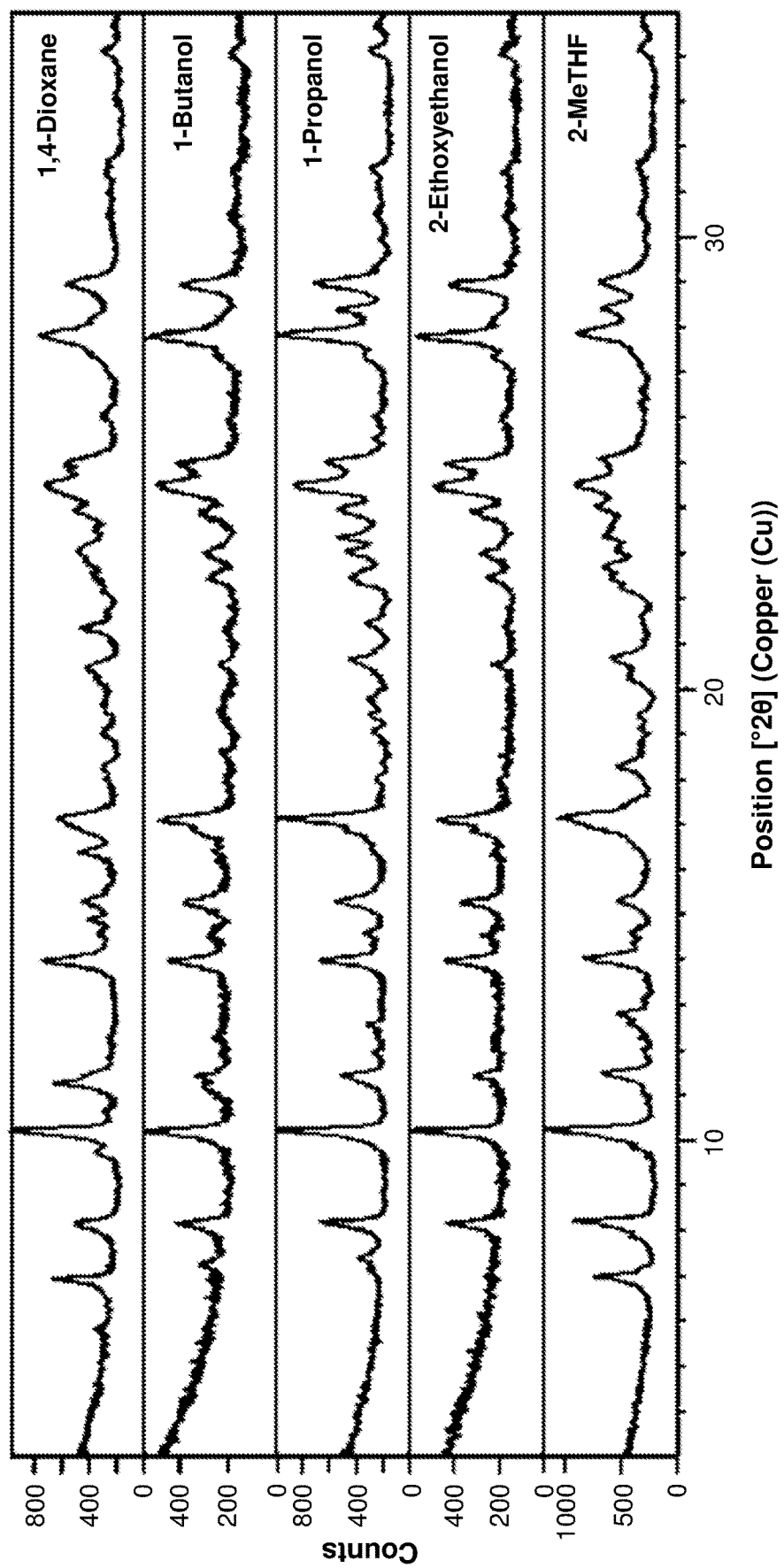
FIGS. 21A-21D. XRPD 2θ diffractograms of BT-11 dihydrochloride Form 3 produced from various solvents.
Figure 21B:
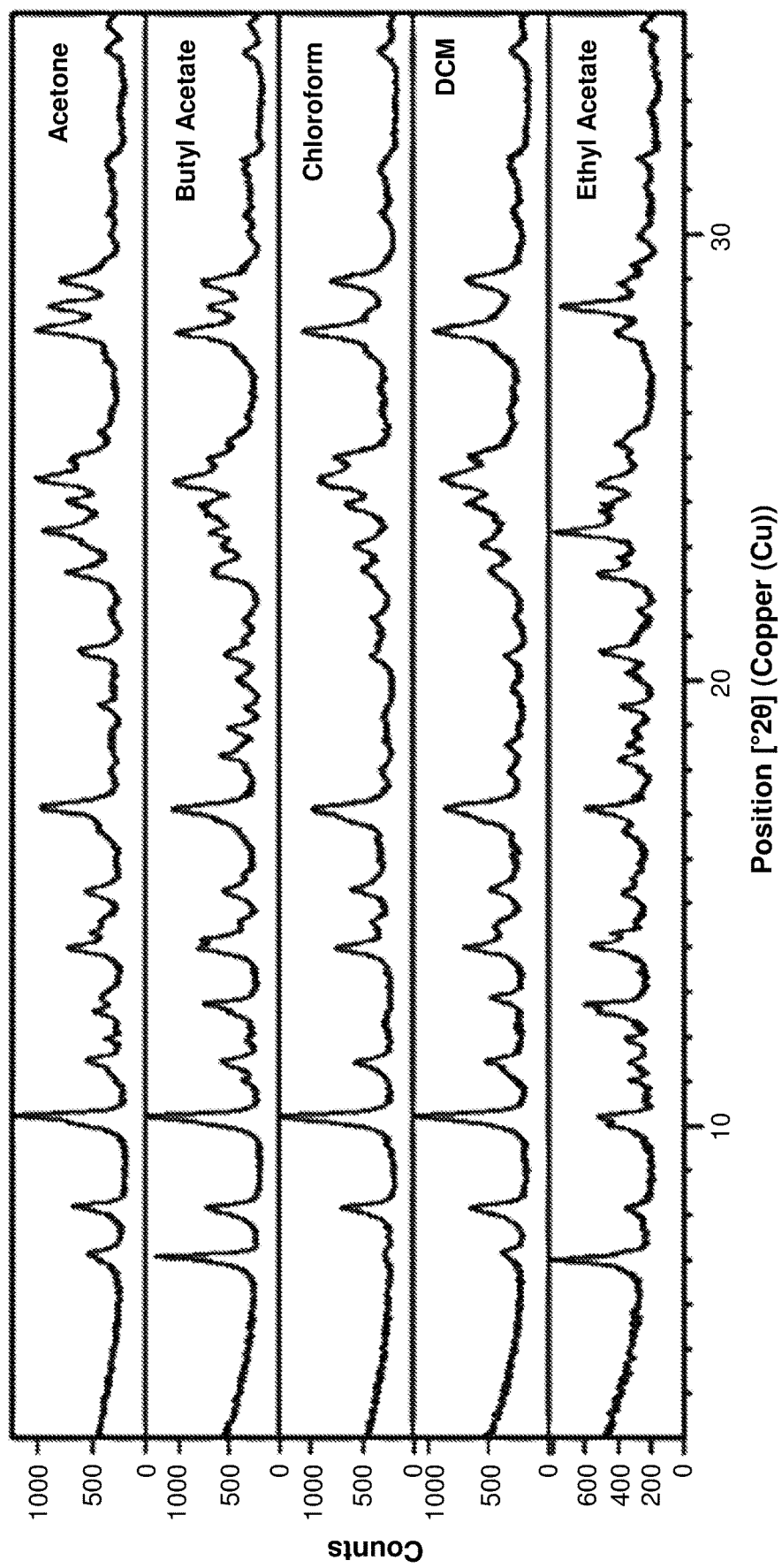
Figure 21C:
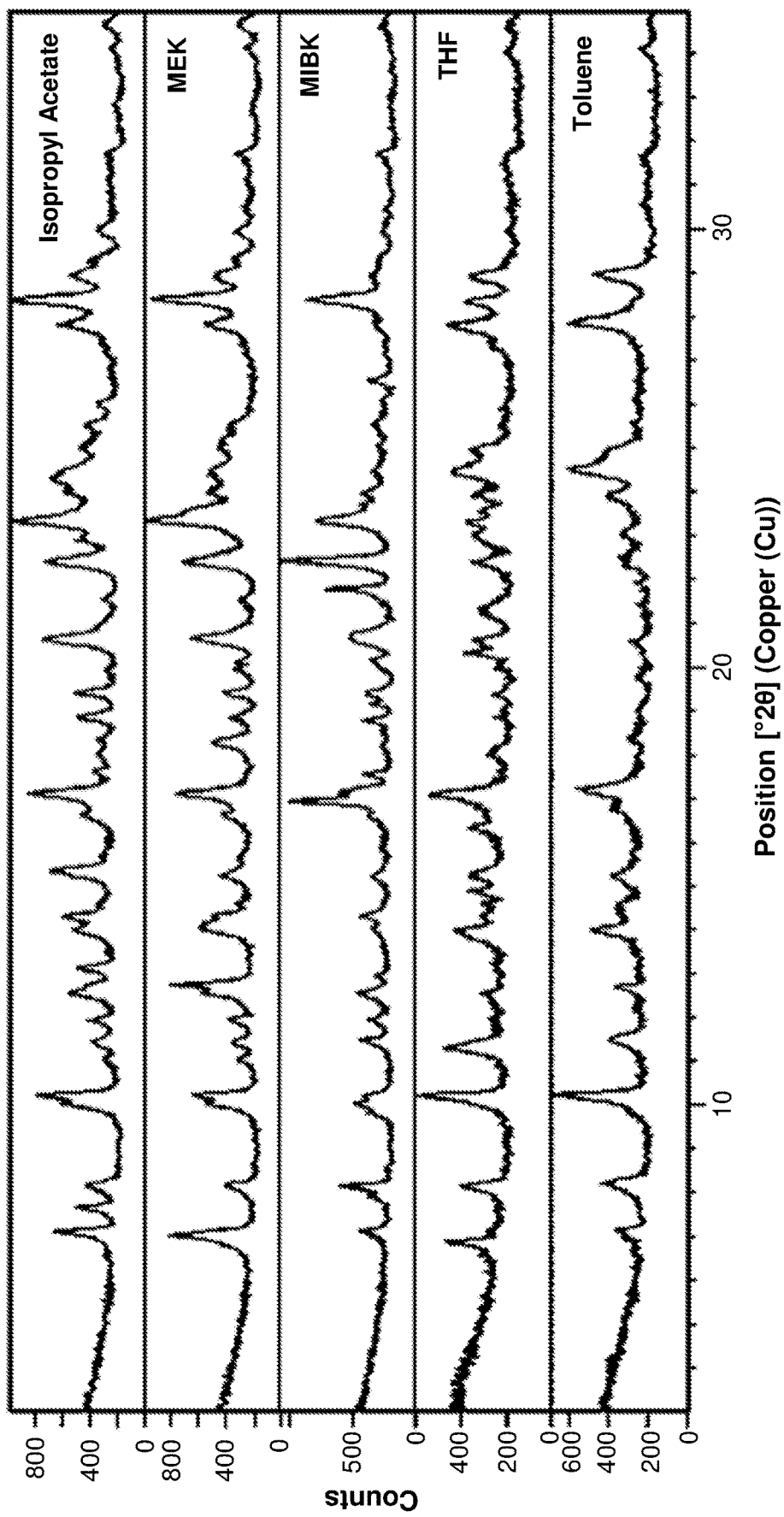
Figure 21D:
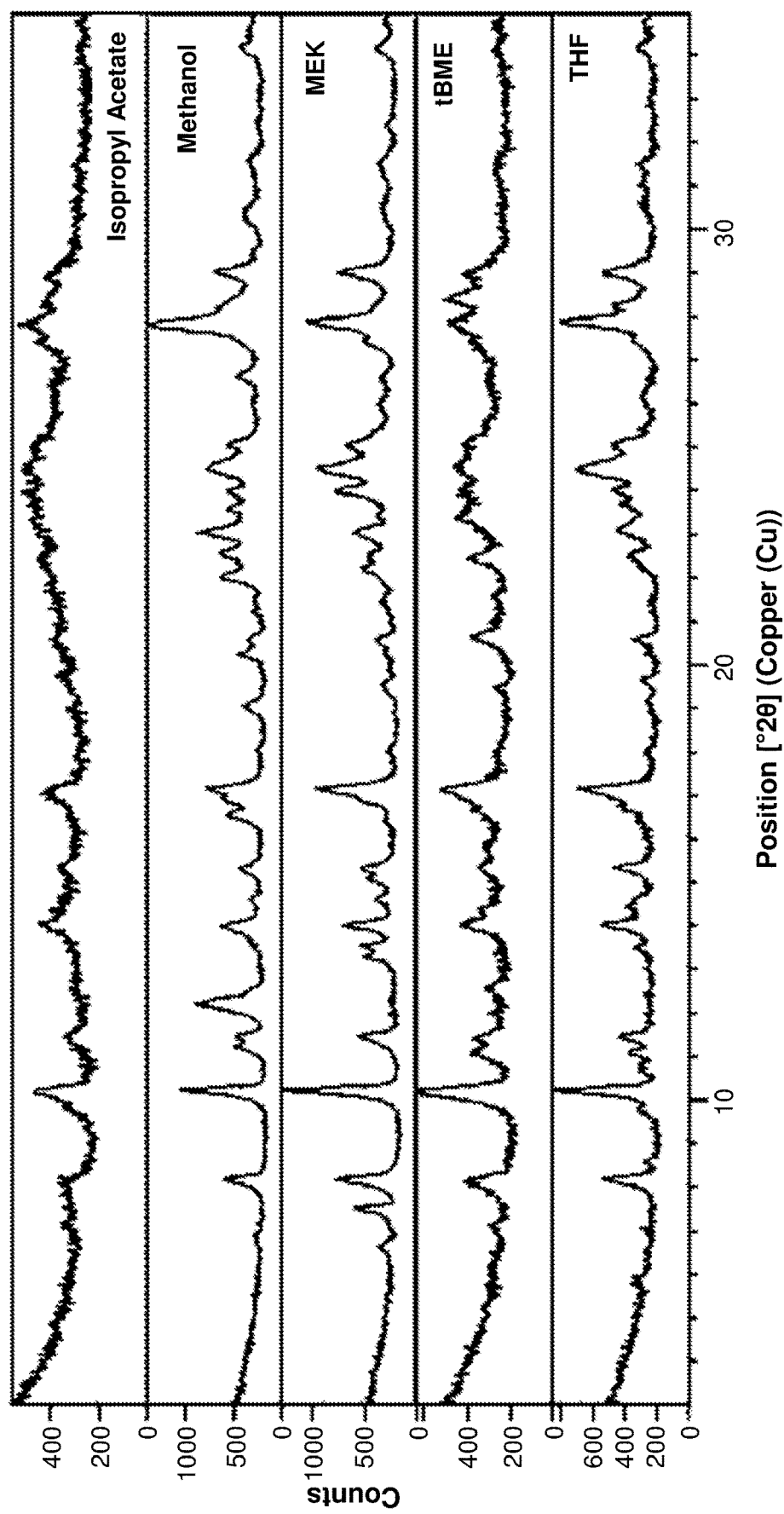

Form 2 of piperazine-1,4-diylbis((6-(1H-benzo[d]imidazo-2-yl)pyridine-2-yl)methanone) has many advantages over the other forms provided herein. These advantages include increased thermostability, a substantially normalized and uniform size distribution (compare, e.g., FIG. 20 with FIGS. 3 and 10), and enhanced gut-restricted pharmacokinetic properties after oral administration (see, e.g., Table 20). The increased thermostability results in an increased shelf-life. The normalized and uniform size is advantageous for formulating piperazine-1,4-diylbis((6-(1H-benzo[d]imidazo-2-yl)pyridine-2-yl)methanone) in compositions, such as pharmaceutical compositions. In particular, control of particle size improves batch-to-batch consistency in tissue penetration and bioavailability, potentially improving reproducibility of clinical efficacy and performance in addition to normalizing manufacturing processes. The enhanced gut-restricted pharmacokinetic properties are advantageous for orally administering piperazine-1,4-diylbis((6-(1H-benzo[d]imidazo-2-yl)pyridine-2-yl)methanone) for the treatment of intestinal diseases, such as inflammatory bowel diseases (e.g., ulcerative colitis and/or Crohn's disease).

Any aspect of the invention described herein as pertaining to a crystal form of piperazine-1,4-diylbis((6-(1H-benzo[d]imidazo-2-yl)pyridine-2-yl)methanone) exemplified by Form 2 can have a Dv50 within a range of about 13-55 μm, such as about 20-48 μm, about 27-41 μm or about 26.9-40.7 μm. Any aspect of the invention described herein as pertaining to a crystal form of piperazine-1,4-diylbis((6-(1H-benzo[d]imidazo-2-yl)pyridine-2-yl)methanone) exemplified by Form 2 can have a Dv10 within a range of about 5-28 μm, such as about 9-24, about 13-20 μm, or about 12.5-20.3 μm. Any aspect of the invention described herein as pertaining to a crystal form of piperazine-1,4-diylbis((6-(1H-benzo[d]imidazo-2-yl)pyridine-2-yl)methanone) exemplified by Form 2 can have a Dv90 within a range of about 18-117 μm, such as about 34-100, about 51-84, or about 50.9-83.9 μm. Any aspect of the invention described herein as pertaining to a crystal form of piperazine-1,4-diylbis((6-(1H-benzo[d]imidazo-2-yl)pyridine-2-yl)methanone) exemplified by Form 2 can have a Dv50 within a range of about 13-55 µm, such as about 20-48 µm, about 27-41 µm or about 26.9-40.7 µm; a Dv10 within a range of about 5-28 µm, such as about 9-24, about 13-20 µm, or about 12.5-20.3 µm; and a Dv90 within a range of about 18-117 µm, such as about 34-100, about 51-84, or about 50.9-83.9 µm, with the proviso that the Dv10 is a lower value than the Dv50 and the Dv50 is a lower value than the Dv90. "Dv50," "Dv10," and "Dv90" are common terms in the art pertaining to particle size and refer to the maximum particle size for a given percentage volume of a sample, wherein "D" refers to diameter, "v" refers to a distribution weighting by volume, and "50," "10," and "90" refer to percentages of sample below the given diameter values. For example, the Dv50 is the maximum particle diameter below which 50% of the same volume exists. The Dv50 is also known as the median particle size by volume. The Dv50, the Dv10, and the Dv90 together provide an indication of the width or breadth of a particle size distribution.

An aspect of the invention is a crystal form of piperazine-1,4-diylbis((6-(1H-benzo[d]imidazo-2-yl)pyridine-2-yl)methanone) having a peak within at least one, at least two, at least three, at least four, at least five, at least six, or each 2θ value range(s) selected from 10.1 to 10.5, 13.8 to 14.2, 16.9 to 17.3, 23.7 to 24.1, 24.3 to 24.7, 27.7 to 28.1, and 28.8 to 29.2 degrees in an X-ray powder diffraction pattern obtained using Cu K alpha radiation. In some versions, the piperazine-1,4-diylbis((6-(1H-benzo[d]imidazo-2-yl)pyridine-2-yl)methanone) has a peak within at least one, at least two, at least three, or each 2θ value range(s) selected from 10.1 to 10.5, 16.9 to 17.3, 23.7 to 24.1, and 28.8 to 29.2 degrees. In some versions, the crystal form of piperazine-1,4-diylbis((6-(1H-benzo[d]imidazo-2-yl)pyridine-2-yl)methanone) has a peak within a 2θ value range of 10.1 to 10.5 degrees. In some versions, the crystal form of piperazine-1,4-diylbis((6-(1H-benzo[d]imidazo-2-yl)pyridine-2-yl)methanone) has a peak within a 2θ value range of 16.9 to 17.3 degrees. In some versions, the crystal form of piperazine-1,4-diylbis((6-(1H-benzo[d]imidazo-2-yl)pyridine-2-yl)methanone) has a peak within a 2θ value range of 23.7 to 24.1 degrees. In some versions, the crystal form of piperazine-1,4-diylbis((6-(1H-benzo[d]imidazo-2-yl)pyridine-2-yl)methanone) has a peak within a 2θ value range of 28.8 to 29.2 degrees. In some versions, the crystal form of piperazine-1,4-diylbis((6-(1H-benzo[d]imidazo-2-yl)pyridine-2-yl)methanone) has a peak within at least one, at least two, or each 2θ value range(s) selected from 13.8 to 14.2, 24.3 to 24.7, and 27.7 to 28.1 degrees. An exemplary crystal form of piperazine-1,4-diylbis((6-(1H-benzo[d]imidazo-2-yl)pyridine-2-yl)methanone) having these characteristics is provided herein as Form 3.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to any pattern provided in any one of FIGS. 21A, 21B, 21C, and 21D. An exemplary crystal form of piperazine-1,4-diylbis((6-(1H-benzo[d]imidazo-2-yl)pyridine-2-yl)methanone) having these characteristics is provided herein as Form 3.

An aspect of the invention is directed to a crystal form of piperazine-1,4-diylbis((6-(1H-benzo[d]imidazo-2-yl)pyridine-2-yl)methanone) with the unit cell dimensions a=9.30 Å, α=71.15°, b=11.78 Å, β=106.99°, c=10.20 Å, γ=108.35°. An exemplary crystal form of piperazine-1,4-diylbis((6-(1H-benzo[d]imidazo-2-yl)pyridine-2-yl)methanone) having these characteristics is provided herein as Form 3.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 7. An exemplary crystal form of piperazine-1,4-diylbis((6-(1H-benzo[d]imidazo-2-yl)pyridine-2-yl)methanone) having these characteristics is provided herein as Form 3.

An aspect of the invention is directed to a crystal form of piperazine-1,4-diylbis((6-(1H-benzo[d]imidazo-2-yl)pyridine-2-yl)methanone) having a peak within at least one, at least two, at least three, at least four, at least five, at least six, or each 2θ value range(s) selected from 5.7 to 6.1, 9.6 to 10.0, 14.0 to 14.4, 19.4 to 19.8, 23.0 to 23.4, 24.1 to 24.5, and 27.9 to 28.3 degrees in an X-ray powder diffraction pattern obtained using Cu K alpha radiation. In some versions, the crystal form of piperazine-1,4-diylbis((6-(1H-benzo[d]imidazo-2-yl)pyridine-2-yl)methanone) has a peak within a 2θ value range of 5.7 to 6.1. An exemplary crystal form of piperazine-1,4-diylbis((6-(1H-benzo[d]imidazo-2-yl)pyridine-2-yl)methanone) having these characteristics is provided herein as Form 1.

Figure 4A:
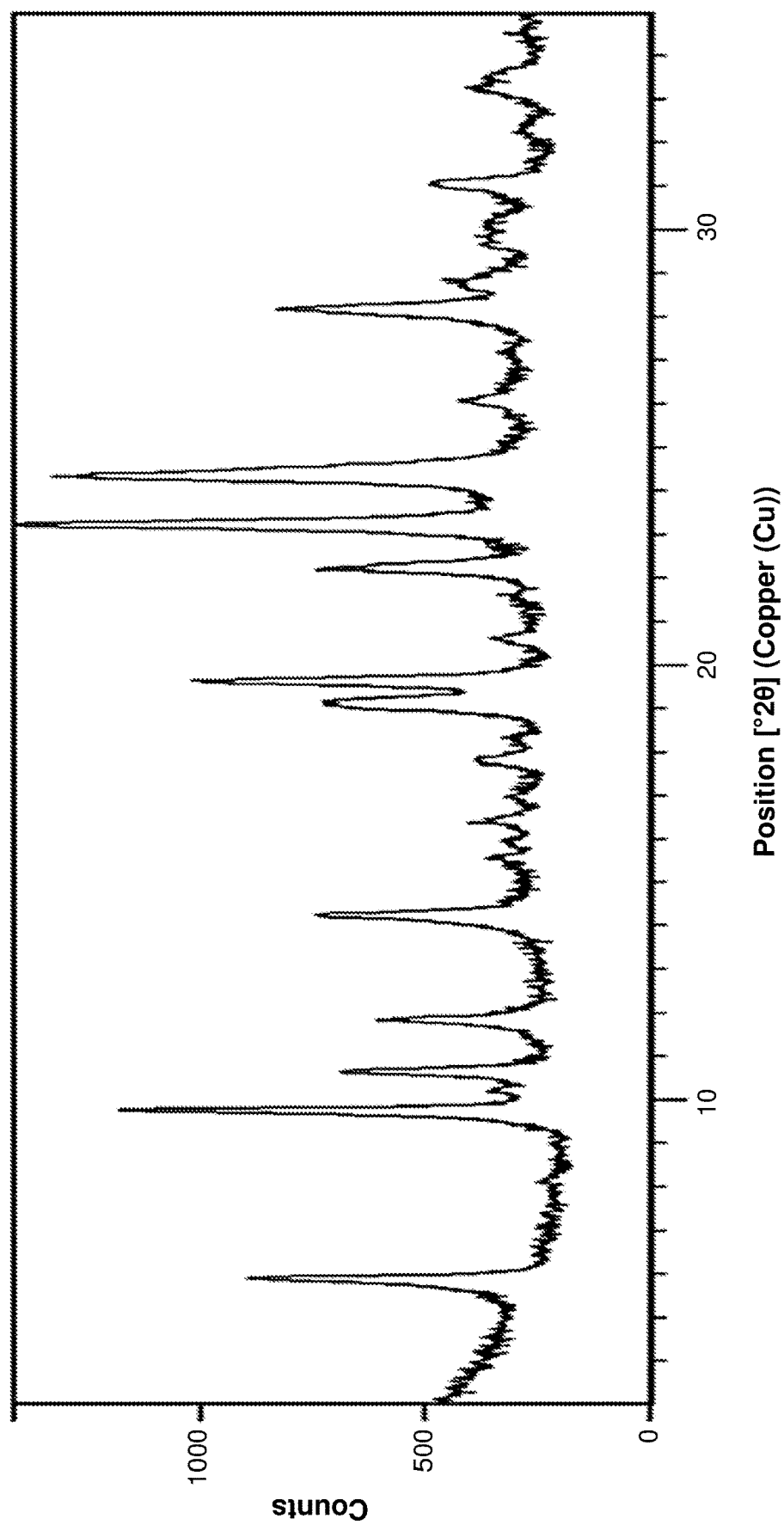
FIGS. 4A and 4B. XRPD 2θ diffractograms displaying BT-11 dihydrochloride Form 1 made by Method A (FIG. 4A) and Method B (FIG. 4B).
Figure 4B:
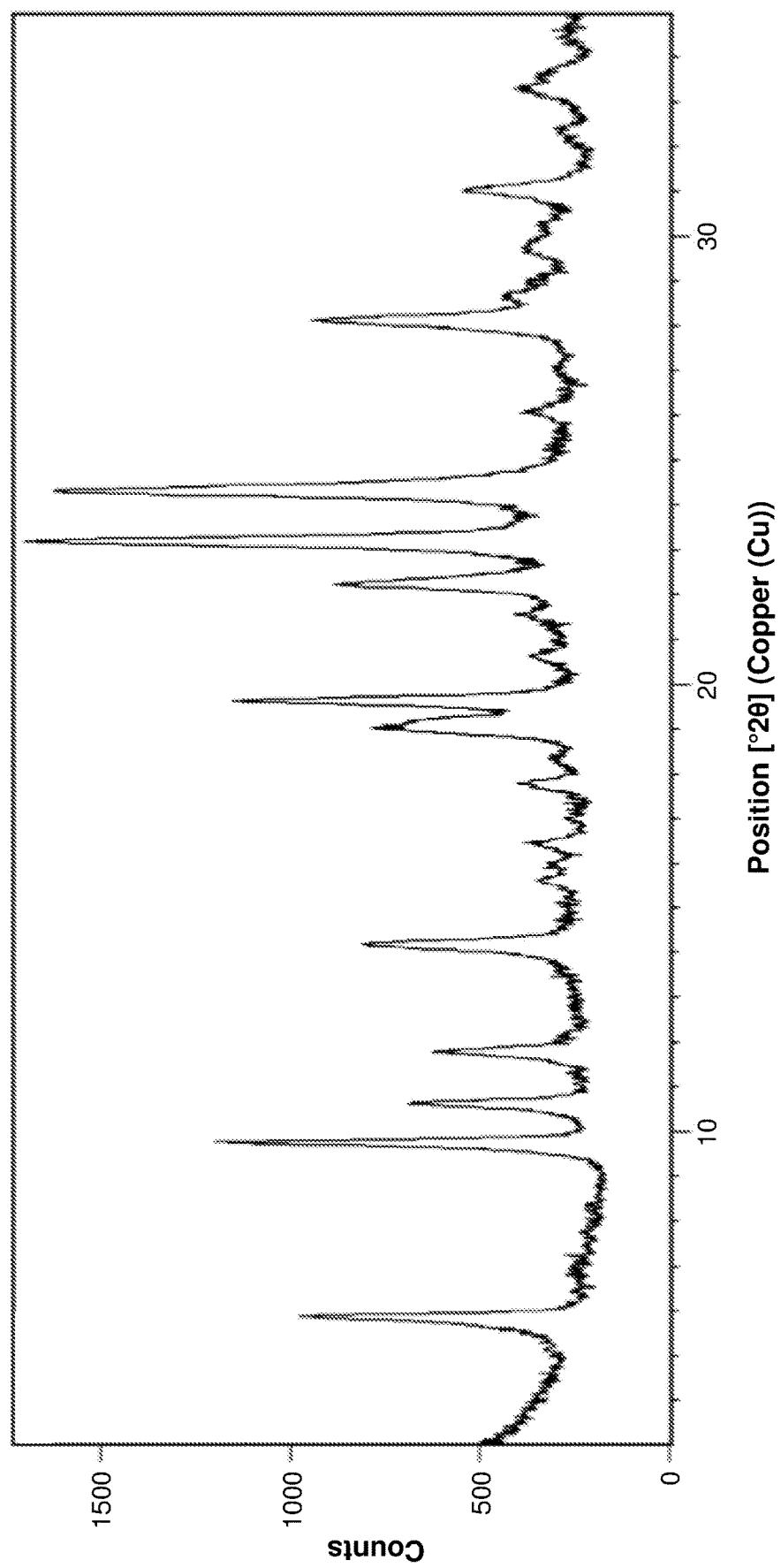

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to any pattern provided in any one of FIGS. 4A and 4B. An exemplary crystal form of piperazine-1,4-diylbis((6-(1H-benzo[d]imidazo-2-yl)pyridine-2-yl)methanone) having these characteristics is provided herein as Form 1.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 3. An exemplary crystal form of piperazine-1,4-diylbis((6-(1H-benzo[d]imidazo-2-yl)pyridine-2-yl)methanone) having these characteristics is provided herein as Form 1.

An aspect of the invention is directed to a crystal form of piperazine-1,4-diylbis((6-(1H-benzo[d]imidazo-2-yl)pyridine-2-yl)methanone) with the unit cell dimensions a=6.97 Å, α=98.26°, b=15.17 Å, β=101.74°, c=9.31 Å, γ=89.23°. An exemplary crystal form of piperazine-1,4-diylbis((6-(1H-benzo[d]imidazo-2-yl)pyridine-2-yl)methanone) having these characteristics is provided herein as Form 1.

An aspect of the invention is directed to a crystal form of piperazine-1,4-diylbis((6-(1H-benzo[d]imidazo-2-yl)pyridine-2-yl)methanone) having a peak within at least one, at least two, at least three, at least four, at least five, or each 2θ value range(s) selected from 12.0 to 12.4, 15.0 to 15.4, 15.3 to 15.7, 21.9 to 22.3, 22.2 to 22.6, and 28.0 to 28.4 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 0.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 1. An exemplary crystal form of piperazine-1,4-diylbis((6-(1H-benzo[d]imidazo-2-yl)pyridine-2-yl)methanone) having these characteristics is provided herein as Form 0.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 1. An exemplary crystal form of piperazine-1,4-diylbis((6-(1H-benzo[d]imidazo-2-yl)pyridine-2-yl)methanone) having these characteristics is provided herein as Form 0.

An aspect of the invention is directed to a crystal form of piperazine-1,4-diylbis((6-(1H-benzo[d]imidazo-2-yl)pyridine-2-yl)methanone) having a peak within at least one, at least two, at least three, or each 2θ value range(s) selected from 6.9 to 7.3, 12.9 to 13.3, 23.4 to 23.8, and 27.3 to 27.7 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 4.

Figure 25:
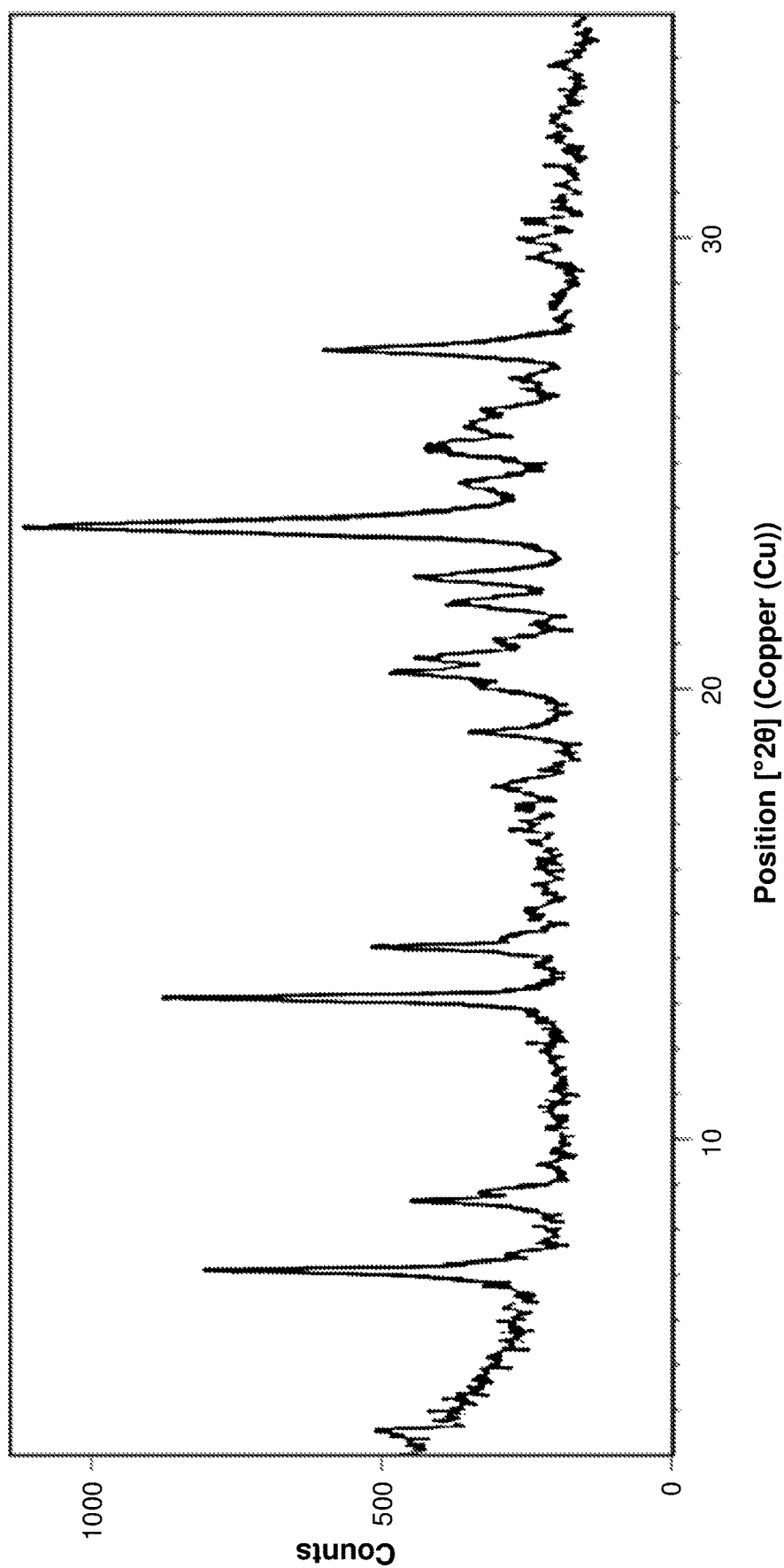
FIG. 25. XRPD 2θ diffractogram of BT-11 dihydrochloride Form 4 produced from acetic acid.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 25. An exemplary crystal form of piperazine-1,4-diylbis((6-(1H-benzo[d]imidazo-2-yl)pyridine-2-yl)methanone) having these characteristics is provided herein as Form 4.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 9. An exemplary crystal form of piperazine-1,4-diylbis((6-(1H-benzo[d]imidazo-2-yl)pyridine-2-yl)methanone) having these characteristics is provided herein as Form 4.

An aspect of the invention is directed to a crystal form of piperazine-1,4-diylbis((6-(1H-benzo[d]imidazo-2-yl)pyridine-2-yl)methanone) having a peak within at least one, at least two, at least three, or each 2θ value range(s) selected from 3.5 to 3.9, 7.2 to 7.6, 14.6 to 15.0, and 24.5 to 24.9 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 5.

Figure 26:
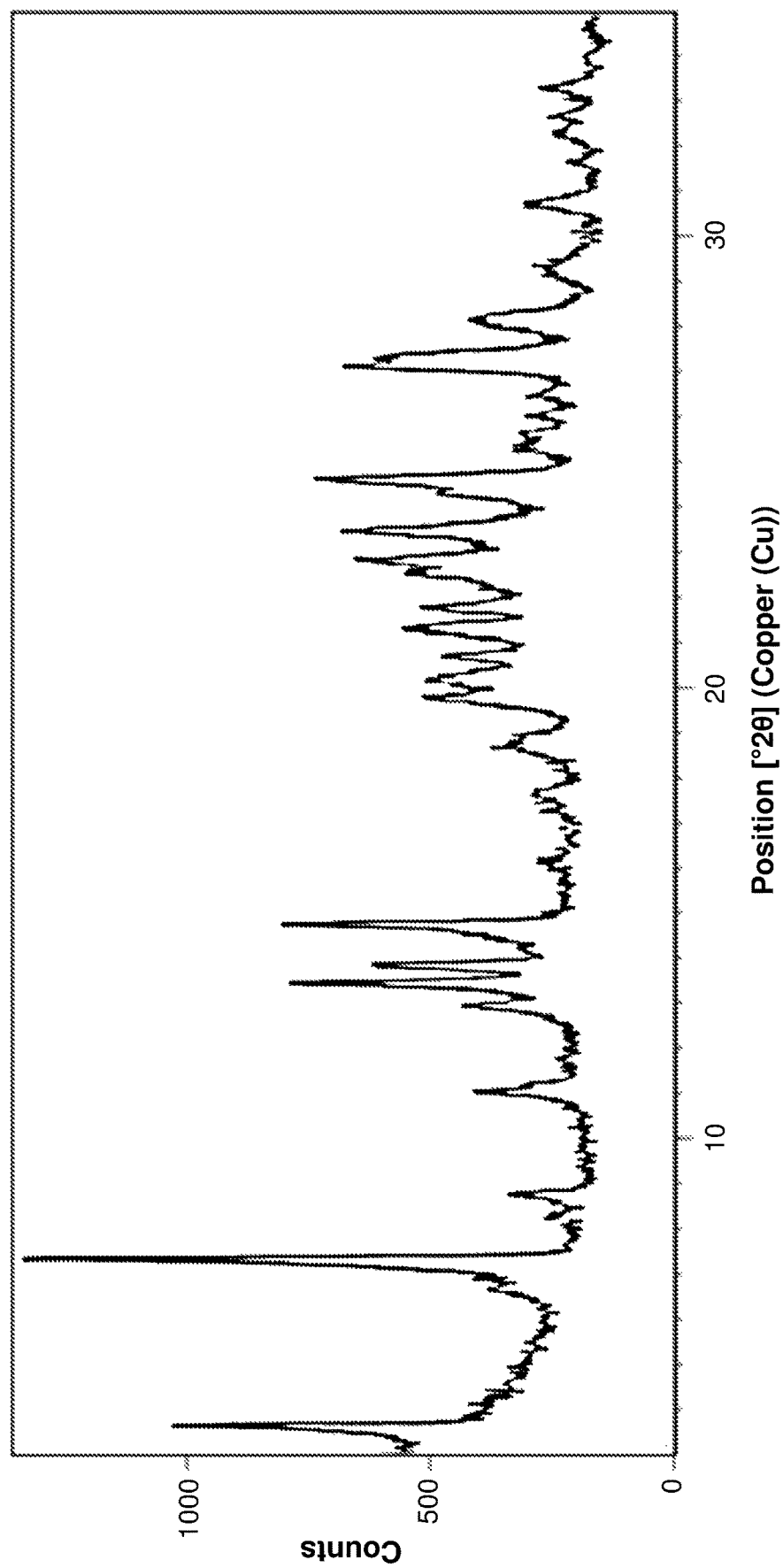
FIG. 26. XRPD 2θ diffractogram of BT-11 dihydrochloride Form 5 produced from acetonitrile.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 26. An exemplary crystal form of piperazine-1,4-diylbis((6-(1H-benzo[d]imidazo-2-yl)pyridine-2-yl)methanone) having these characteristics is provided herein as Form 5.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 10. An exemplary crystal form of piperazine-1,4-diylbis((6-(1H-benzo[d]imidazo-2-yl)pyridine-2-yl)methanone) having these characteristics is provided herein as Form 5.

An aspect of the invention is directed to a crystal form of piperazine-1,4-diylbis((6-(1H-benzo[d]imidazo-2-yl)pyridine-2-yl)methanone) having a peak within at least one, at least two, or each 2θ value range(s) selected from 9.2 to 9.6, 26.6 to 27.0, and 27.6 to 28.0 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 6.

Figure 28:
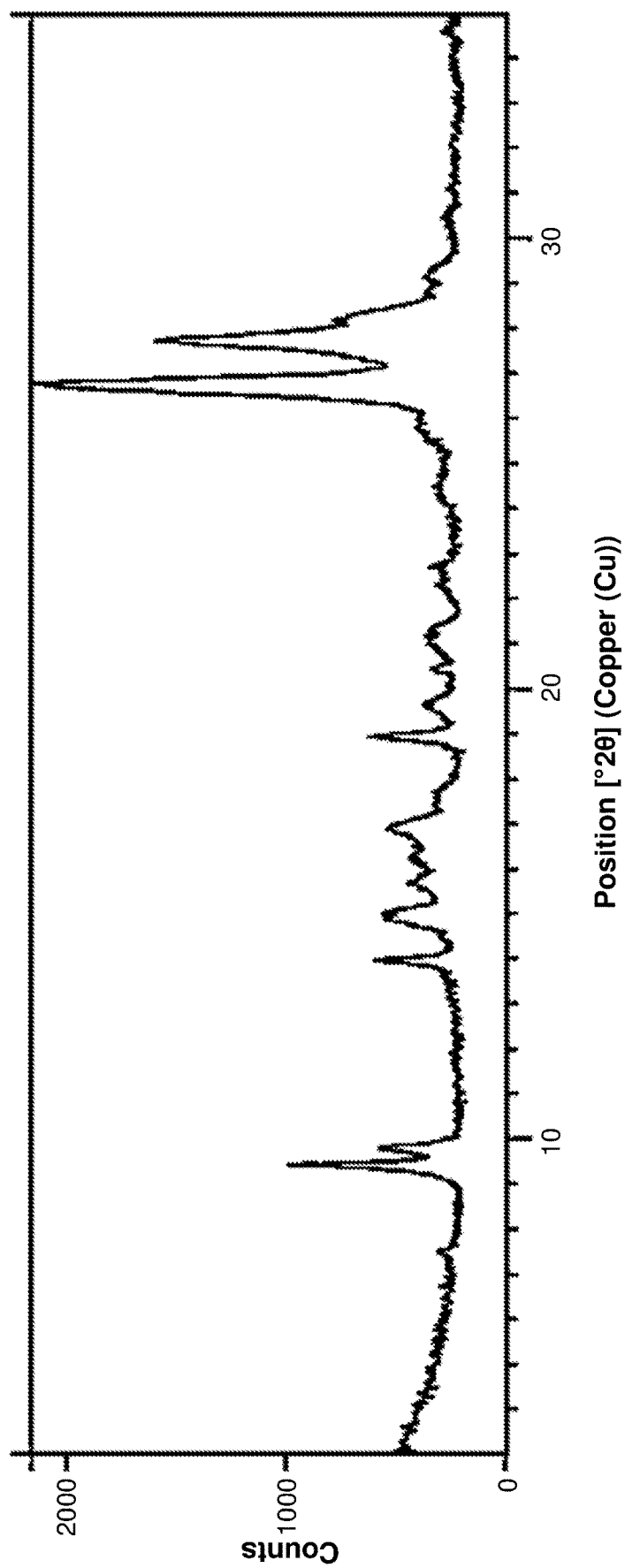
FIG. 28. XRPD 2θ diffractograms of BT-11 dihydrochloride Form 6 produced from water.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 28. An exemplary crystal form of piperazine-1,4-diylbis((6-(1H-benzo[d]imidazo-2-yl)pyridine-2-yl)methanone) having these characteristics is provided herein as Form 6.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 11. An exemplary crystal form of piperazine-1,4-diylbis((6-(1H-benzo[d]imidazo-2-yl)pyridine-2-yl)methanone) having these characteristics is provided herein as Form 6.

An aspect of the invention is directed to a crystal form of piperazine-1,4-diylbis((6-(1H-benzo[d]imidazo-2-yl)pyridine-2-yl)methanone) having a peak within at least one, at least two, at least three, at least four, or each 2θ value range(s) selected from 9.9 to 10.3, 12.1 to 12.5, 20.5 to 20.9, 25.7 to 26.1, and 26.9 to 27.3 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 7.

Figure 30:
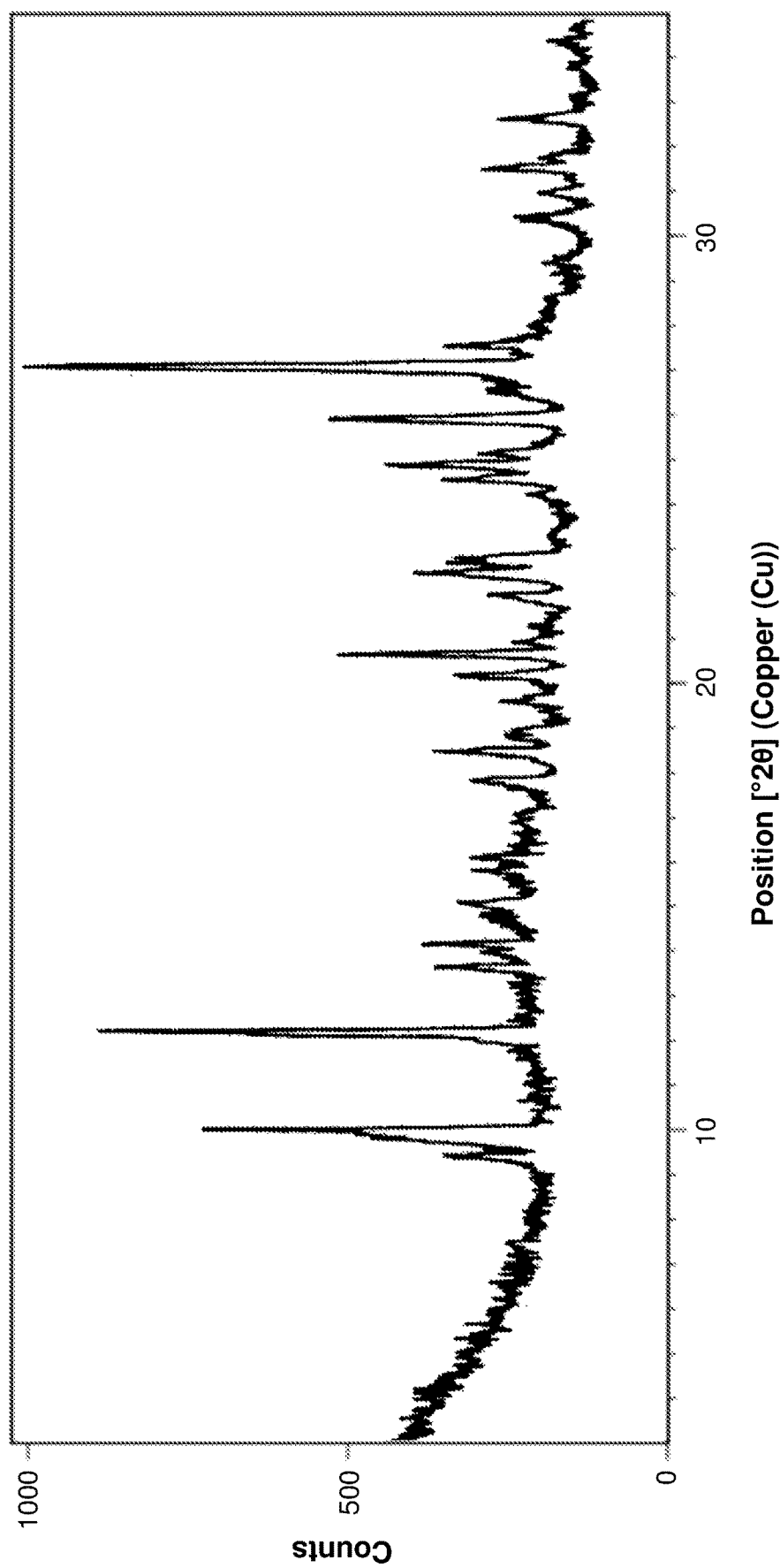
FIG. 30. XRPD 2θ diffractogram of BT-11 dihydrochloride Form 7 produced upon evaporation of MeOH/water (80:20% v/v).

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 30. An exemplary crystal form of piperazine-1,4-diylbis((6-(1H-benzo[d]imidazo-2-yl)pyridine-2-yl)methanone) having these characteristics is provided herein as Form 7.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 13. An exemplary crystal form of piperazine-1,4-diylbis((6-(1H-benzo[d]imidazo-2-yl)pyridine-2-yl)methanone) having these characteristics is provided herein as Form 7.

An aspect of the invention is directed to a crystal form of piperazine-1,4-diylbis((6-(1H-benzo[d]imidazo-2-yl)pyridine-2-yl)methanone) having a peak within at least one, at least two, at least three, at least four, or each 2θ value range(s) selected from 7.4 to 7.8, 13.1 to 13.5, 22.1 to 22.5, 23.9 to 24.3, and 25.1 to 25.5 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 8.

Figure 31:
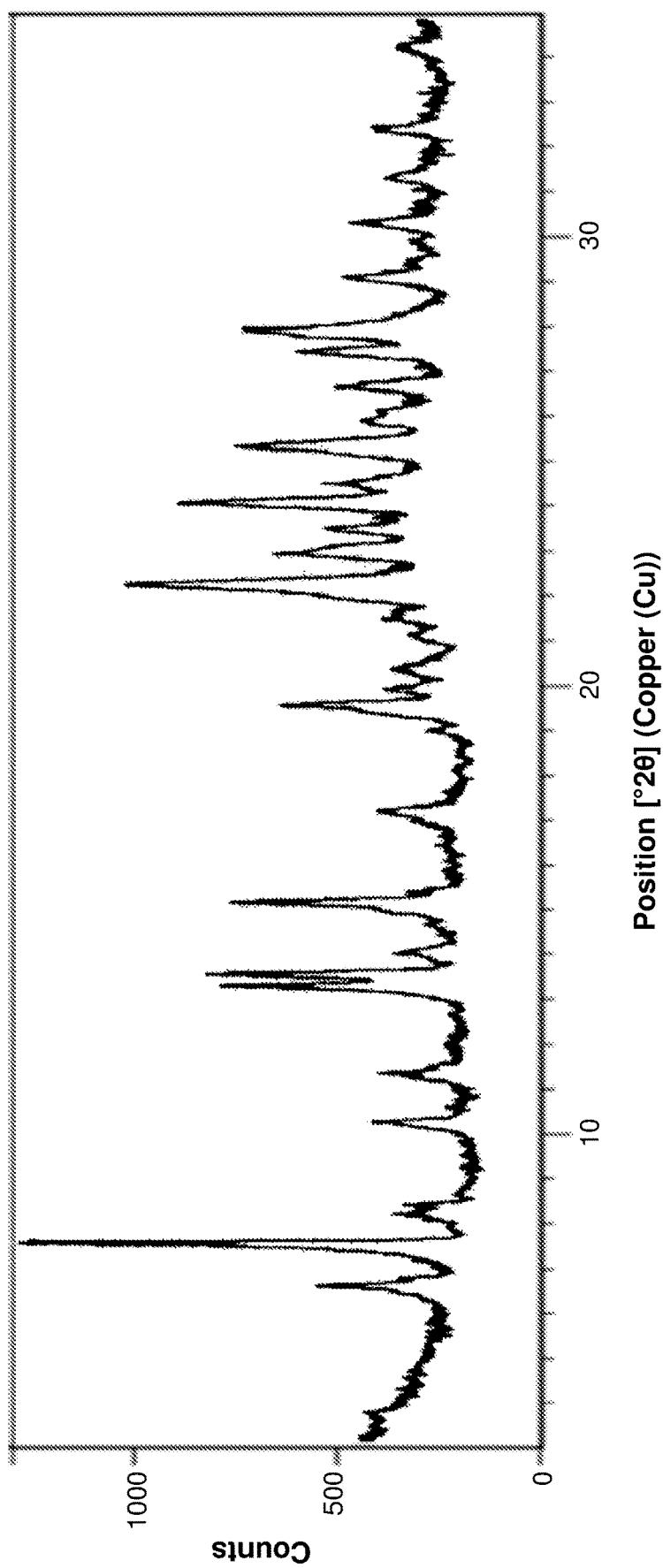
FIG. 31. XRPD 2θ diffractograms of BT-11 dihydrochloride Form 8 produced from 2-propanol.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 31. An exemplary crystal form of piperazine-1,4-diylbis((6-(1H-benzo[d]imidazo-2-yl)pyridine-2-yl)methanone) having these characteristics is provided herein as Form 8.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 15. An exemplary crystal form of piperazine-1,4-diylbis((6-(1H-benzo[d]imidazo-2-yl)pyridine-2-yl)methanone) having these characteristics is provided herein as Form 8.

An aspect of the invention is directed to a crystal form of piperazine-1,4-diylbis((6-(1H-benzo[d]imidazo-2-yl)pyridine-2-yl)methanone) having a peak within at least one, at least two, at least three, or each 2θ value range(s) selected from 9.9 to 10.3, 12.1 to 12.5, 25.8 to 26.2, and 26.9 to 27.3 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 9.

Figure 33:
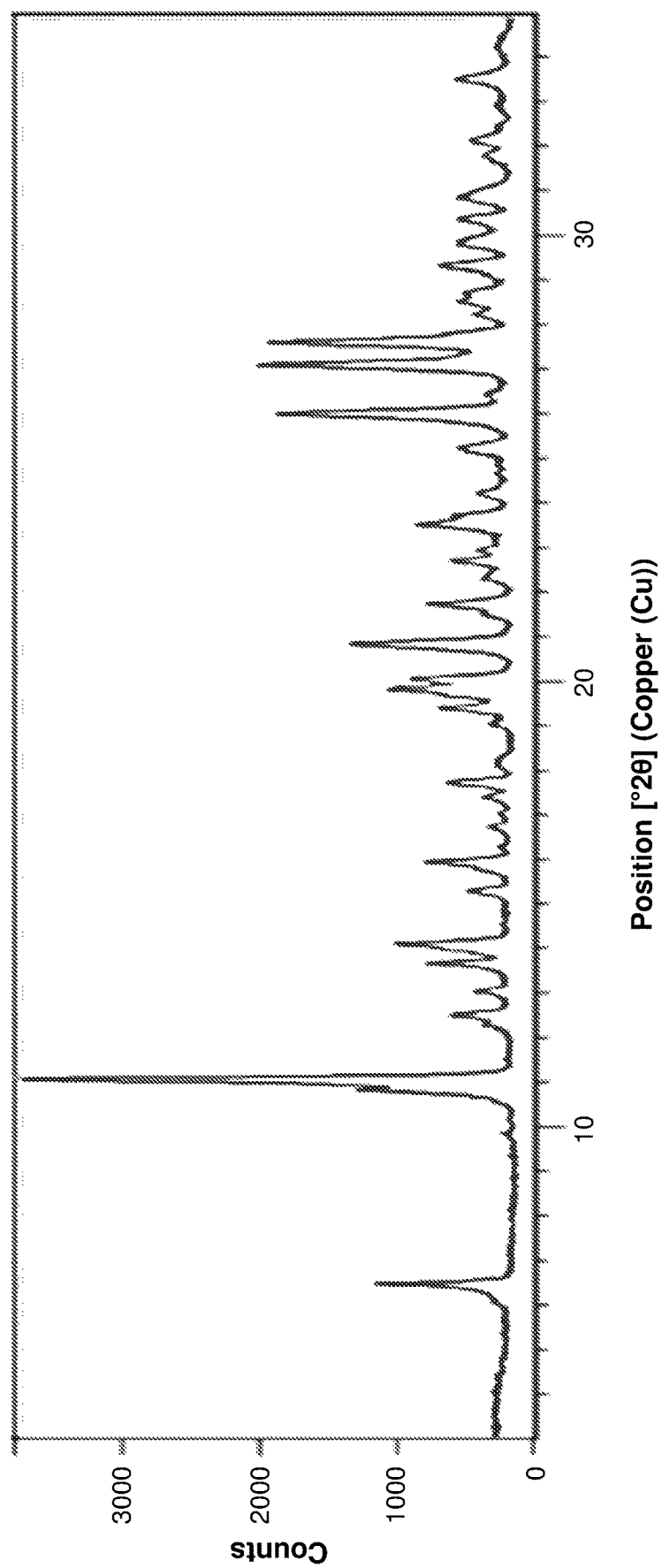
FIG. 33. XRPD 2θ diffractograms of BT-11 dihydrochloride Form 9 produced from ethanol.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 33. An exemplary crystal form of piperazine-1,4-diylbis((6-(1H-benzo[d]imidazo-2-yl)pyridine-2-yl)methanone) having these characteristics is provided herein as Form 9.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 16. An exemplary crystal form of piperazine-1,4-diylbis((6-(1H-benzo[d]imidazo-2-yl)pyridine-2-yl)methanone) having these characteristics is provided herein as Form 9.

An aspect of the invention is directed to a crystal form of piperazine-1,4-diylbis((6-(1H-benzo[d]imidazo-2-yl)pyridine-2-yl)methanone) having a peak within at least one, at least two, at least three, at least four, at least five, or each 2θ value range(s) selected from 8.8 to 9.2, 9.4 to 9.8, 19.1 to 19.5, 23.0 to 23.4, 26.0 to 26.4, and 27.3 to 27.7 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 10.

Figure 35:
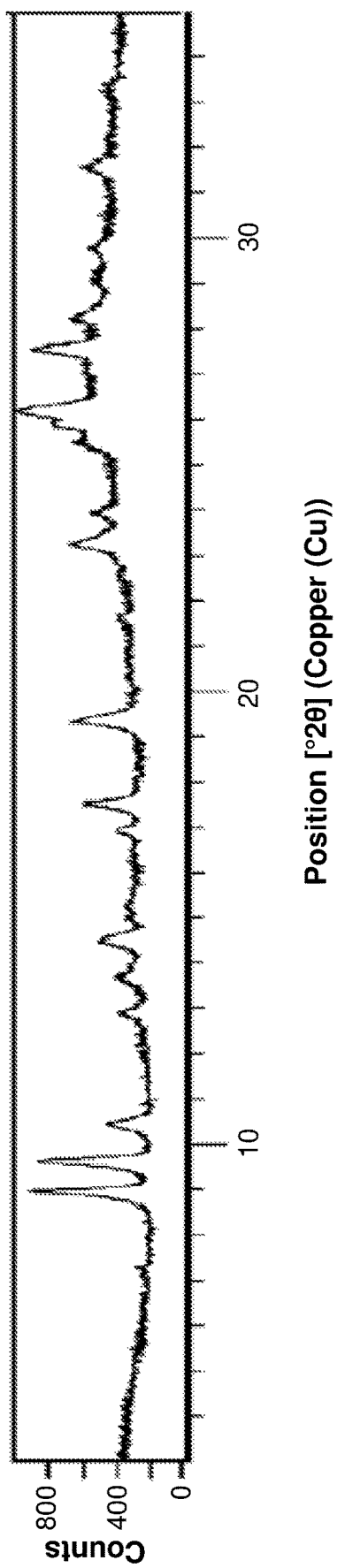
FIG. 35. XRPD 2θ diffractogram of BT-11 dihydrochloride Form 10 produced upon slurrying Form 3 in pH 1.2 buffer.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 35. An exemplary crystal form of piperazine-1,4-diylbis((6-(1H-benzo[d]imidazo-2-yl)pyridine-2-yl)methanone) having these characteristics is provided herein as Form 10.

An aspect of the invention is directed to a crystal form of piperazine-1,4-diylbis((6-(1H-benzo[d]imidazo-2-yl)pyridine-2-yl)methanone) having an X-ray powder diffraction peak at about any one or more 2θ values provided in Table 18. An exemplary crystal form of piperazine-1,4-diylbis((6-(1H-benzo[d]imidazo-2-yl)pyridine-2-yl)methanone) having these characteristics is provided herein as Form 10.

An aspect of the invention is directed to a crystal form of piperazine-1,4-diylbis((6-(1H-benzo[d]imidazo-2-yl)pyridine-2-yl)methanone) having a peak within at least one, at least two, at least three, at least four, or each 2θ value range(s) selected from 15.6 to 16.0, 19.4 to 19.8, 21.4 to 21.8, 23.3 to 23.7, and 27.1 to 27.5 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 11.

Figure 36:
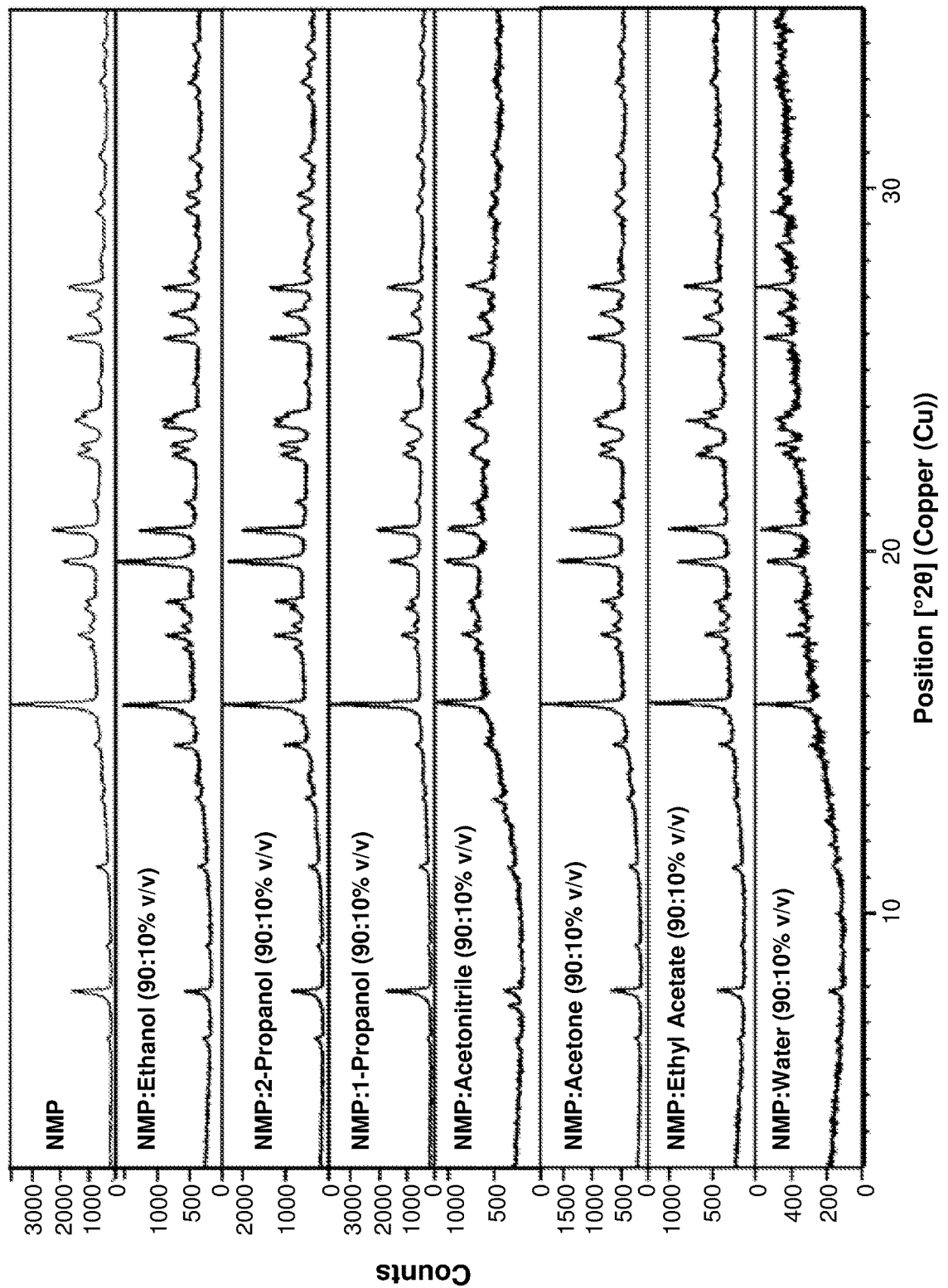
FIG. 36. XRPD 2θ diffractogram of BT-11 dihydrochloride Form 11 produced upon slurrying BT-11 free base in eight buffers.

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to any pattern provided in FIG. 36. An exemplary crystal form of piperazine-1,4-diylbis((6-(1H-benzo[d]imidazo-2-yl)pyridine-2-yl)methanone) having these characteristics is provided herein as Form 11.

An aspect of the invention is directed to a crystal form of piperazine-1,4-diylbis((6-(1H-benzo[d]imidazo-2-yl)pyridine-2-yl)methanone) having a peak within at least one, at least two, at least three, or each 2θ value range(s) selected from 11.6 to 12.0, 18.3 to 18.7, 27.1 to 27.5, 28.0 to 28.4 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 12.

Figure 37:
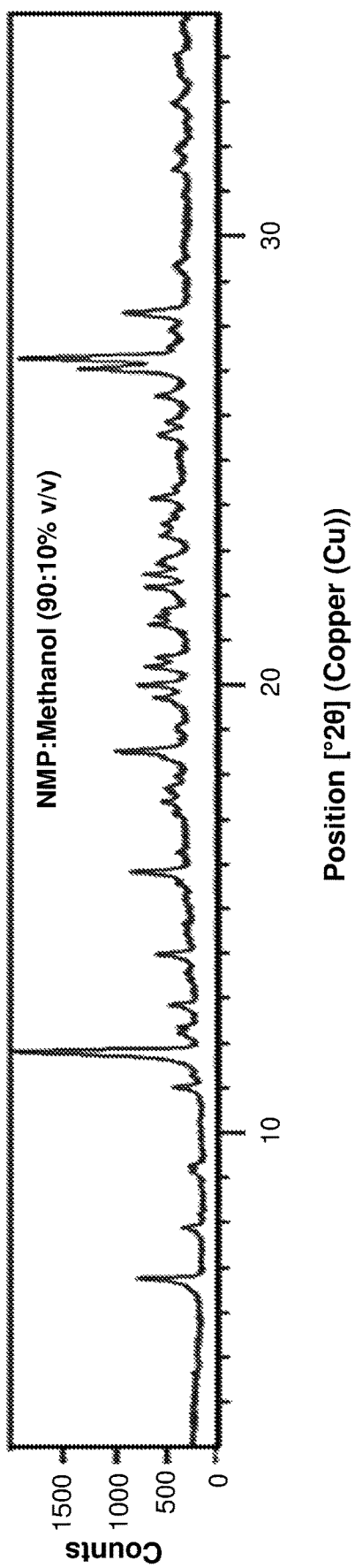
FIG. 37. XRPD 2θ diffractogram of BT-11 dihydrochloride Form 12 produced upon slurrying BT-11 free base in NMP:methanol (90:10).

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 37. An exemplary crystal form of piperazine-1,4-diylbis((6-(1H-benzo[d]imidazo-2-yl)pyridine-2-yl)methanone) having these characteristics is provided herein as Form 12.

An aspect of the invention is directed to a crystal form of piperazine-1,4-diylbis((6-(1H-benzo[d]imidazo-2-yl)pyridine-2-yl)methanone) having a peak within at least one, at least two, or each 2θ value range(s) selected from 9.4 to 9.8, 17.0 to 17.4, and 24.5 to 24.9 degrees in an X-ray powder diffraction pattern obtained using Cu K alpha radiation. An exemplary crystal form of piperazine-1,4-diylbis((6-(1H-benzo[d]imidazo-2-yl)pyridine-2-yl)methanone) having these characteristics is provided herein as Form 13.

Figure 38:
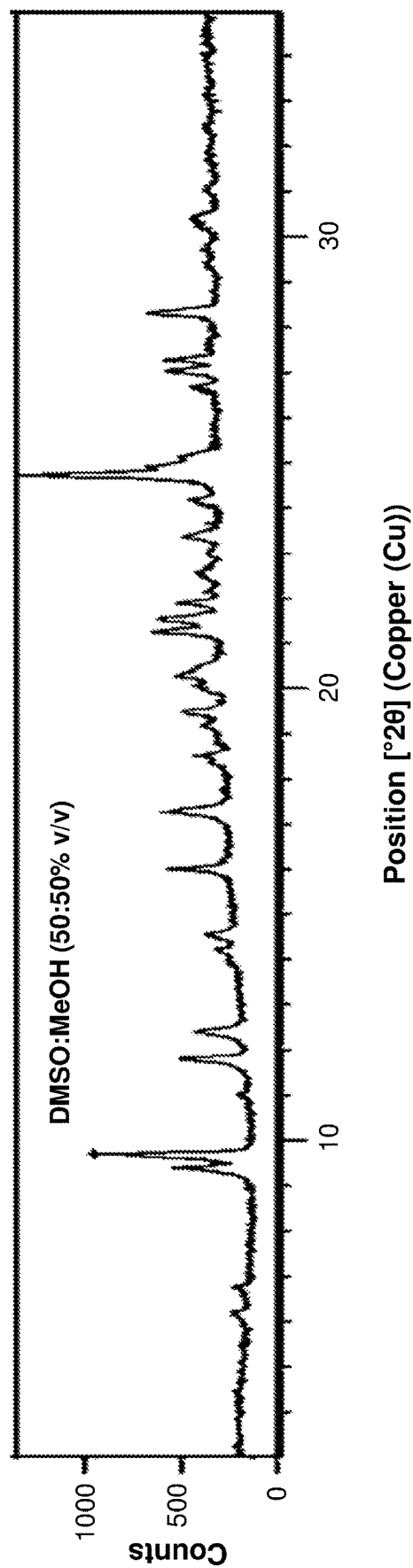
FIG. 38. XRPD 2θ diffractogram of BT-11 dihydrochloride Form 13 produced upon slurrying BT-11 free base in dimethylsulfoxide (DMSO):methanol (50:50).

An aspect of the invention is directed to a crystal form of piperazine-1,4-diylbis((6-(1H-benzo[d]imidazo-2-yl)pyridine-2-yl)methanone) having an X-ray powder diffraction pattern obtained using Cu K alpha radiation substantially similar to the pattern provided in FIG. 38. An exemplary crystal form of piperazine-1,4-diylbis((6-(1H-benzo[d]imidazo-2-yl)pyridine-2-yl)methanone) having these characteristics is provided herein as Form 13.

The invention further provides processes for preparing crystal forms of piperazine-1,4-diylbis((6-(1H-benzo[d]imidazo-2-yl)pyridine-2-yl)methanone). The methods generally comprise mixing piperazine-1,4-diylbis((6-(1H-benzo[d]imidazo-2-yl)pyridine-2-yl)methanone) in a solvent to form a slurry. The methods can further comprise isolating crystallized material from the slurry to obtain isolated material. The methods can further comprise washing the isolated material with a solvent to obtain washed material. The methods can further comprise drying either the isolated material or the washed material to obtain dried material comprising the crystal form of piperazine-1,4-diylbis((6-(1H-benzo[d]imidazo-2-yl)pyridine-2-yl)methanone).

For the preparation of Form 2, the solvent can comprise at least one of methanol, 2-ethoxyethanol, methyl isobutyl ketone, N-methylpyrrolidone, and dimethylsulfoxide. In some versions, the solvent is a mixture of dimethylsulfoxide, methanol, and water. In some versions, the mixture of dimethylsulfoxide, methanol, and water is in a ratio of 45-55:35-45:5-15 (dimethylsulfoxide:methanol:water), such as 50:40:10. In some versions, the solvent is N-methylpyrrolidone or a mixture of N-methylpyrrolidone and one or more of methanol, ethanol, 2-propanol, 1-propanol, acetonitrile, acetone, ethyl acetate, and water. In some versions, the solvent is selected from the group consisting of 2-ethoxyethanol, methyl isobutyl ketone, or a mixture of methanol and water. Some versions comprise isolating crystallized material from the slurry to obtain isolated material; washing the isolated material with a solvent comprising methanol or N-methylpyrrolidone to obtain washed material; and drying the washed material to obtain dried material comprising the crystal form of piperazine-1,4-diylbis((6-(1H-benzo[d]imidazo-2-yl)pyridine-2-yl)methanone). Some versions further comprise seeding the slurry with piperazine-1,4-diylbis((6-

(1H-benzo[d]imidazo-2-yl)pyridine-2-yl)methanone) Form 2. Some versions further comprise cyclically heating and cooling the slurry.

In some versions, the preparation of Form 2 comprises adding piperazine-1,4-diylbis((6-(1H-benzo[d]imidazo-2-yl)pyridine-2-yl)methanone) to DMSO:methanol:water to form a slurry. In some versions, the DMSO:methanol:water is in a ratio of 45-55:35-45:5-15 (dimethylsulfoxide:methanol:water), or about 50:40:10. In some versions, the piperazine-1,4-diylbis((6-(1H-benzo[d]imidazo-2-yl)pyridine-2-yl)methanone) is added to the DMSO:methanol:water in a 1:15-1:50 (w/v) ratio, such as a 1:33 (w/v) ratio, to form the slurry. In some versions, the mixture of the piperazine-1,4-diylbis((6-(1H-benzo[d]imidazo-2-yl)pyridine-2-yl)methanone) in the DMSO:methanol:water is stirred stirring at 25-35° C. for a time period to form the slurry. In some versions, the time period is approximately 5-15 minutes, such as approximately 10 minutes. In some versions, the temperature of the slurry is then raised. In some versions, the temperature of the slurry is raised to 50-75° C., such as 60-65° C. In some versions, approximately 2 to 3 equivalents of HCl is then added to the slurry over a time period. In some versions, the added HCl is in DMSO:methanol:water, such as in a ratio of 45-55:35-45:5-15 (dimethylsulfoxide:methanol:water), or about 50:40:10. In some versions, the time period in which the HCl is added is about 1.5-2.5 hours. In some versions, the reaction is then filtered to form a filtrate. In some versions, the filtering occurs at a temperature 60-65° C. In some versions, Form 2 of piperazine-1,4-diylbis((6-(1H-benzo[d]imidazo-2-yl)pyridine-2-yl)methanone) is added to the filtrate to form a second slurry. The Form 2 can be added in an amount of about 1 to 2 percent weight of the filtrate. In some versions, the second slurry is stirred for a time period. In some versions, the time period is about 6-8 hours. In some versions, the stirring occurs at 60-65° C. In some versions, the second slurry is then cooled. In some versions, the second slurry is cooled to about 20-30° C. In some versions, the second slurry is cooled at a rate of approximately 8° C./hour. In some versions, the second slurry is then stirred at 20 to 30° C. for 1 to 2 hours. In some versions, the second slurry is then further cooled. In some versions, the further cooling is to a temperature of 0 to 5° C. at a rate of approximately 6° C./hour. In some versions, the second slurry is then stirred at 0 to 5° C. for 12 to 14 hours. In some versions, solid material is then filtered, and wet material is slurried in methanol:water. The wet material can be slurried for 5 to 96 hours at 25 to 55° C. In some versions, the wet slurried material is filtered to obtain a filtrate. In some versions, the filtrate is dried. In some versions, the filtrate is dried under vacuum at 25 to 55° C.

For the preparation of Form 3, the solvent can comprise at least one of tetrahydrofuran, 1,4-dioxane, 1-butanol, 1-propanol, 2-methyl THF, butyl acetate, dichloromethane, ethyl acetate, isopropyl alcohol, methanol, methyl ethyl ketone, and tert-butyl methyl ether.

The invention also provides compositions comprising any one or more of the crystal forms of piperazine-1,4-diylbis((6-(1H-benzo[d]imidazo-2-yl)pyridine-2-yl)methanone) of the invention. In some versions, the compositions comprise piperazine-1,4-diylbis((6-(1H-benzo[d]imidazo-2-yl)pyridine-2-yl)methanone) in any one or more crystal forms of as characterized anywhere herein in amount of at least 5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 81% w/w, 82% w/w, 83% w/w, 84% w/w, 85% w/w, 86% w/w, 87% w/w, 88% w/w, 89% w/w, 90% w/w, 91% w/w, 92% w/w, 93% w/w, 94% w/w, 95% w/w, 96% w/w, 97% w/w, 98% w/w, 99% w/w, or 100% w/w of the total amount of piperazine-1,4-diylbis((6-(1H-benzo[d]imidazo-2-yl)pyridine-2-yl)methanone) present in the composition. In some versions, the compositions comprise piperazine-1,4-diylbis((6-(1H-benzo[d]imidazo-2-yl)pyridine-2-yl)methanone) in any one or more crystal forms of as characterized anywhere herein in amount of at least 5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 81% w/w, 82% w/w, 83% w/w, 84% w/w, 85% w/w, 86% w/w, 87% w/w, 88% w/w, 89% w/w, 90% w/w, 91% w/w, 92% w/w, 93% w/w, 94% w/w, 95% w/w, 96% w/w, 97% w/w, 98% w/w, 99% w/w, or 100% w/w of the total amount of the crystalized piperazine-1,4-diylbis((6-(1H-benzo[d]imidazo-2-yl)pyridine-2-yl)methanone) present in the composition. "Crystalized piperazine-1,4-diylbis((6-(1H-benzo[d]imidazo-2-yl)pyridine-2-yl)methanone)" in this context refers to the piperazine-1,4-diylbis((6-(1H-benzo[d]imidazo-2-yl)pyridine-2-yl)methanone) that is not in an amorphous form.

Methods of determining the relative weight percentage of a particular crystalline form may include comparative analysis of a sample of a piperazine-1,4-diylbis((6-(1H-benzo[d]imidazo-2-yl)pyridine-2-yl)methanone) relative to a standard curve by x-ray powder diffraction. Samples of known ratios may be created by isolating purified crystalline forms and blending in ratios of 1:9, 3:7, 1:1, 7:3, and 9:1. Samples of known ratios would then be analyzed by XRPD to determine relative peak heights or peak areas at characteristic positions for each crystalline form. The peak height or peak area would linearly or nonlinearly correspond to the relative weight proportion of a given crystalline form in the overall sample.

In some versions the composition is a pharmaceutical composition. The pharmaceutical compositions may comprise any one or more of the crystal forms of piperazine-1,4-diylbis((6-(1H-benzo[d]imidazo-2-yl)pyridine-2-yl)methanone) of the invention in combination or association with a pharmaceutically acceptable carrier. Such compositions can be used to deliver pharmaceutically effective amounts of one or more of the piperazine-1,4-diylbis((6-(1H-benzo[d]imidazo-2-yl)pyridine-2-yl)methanone) crystal forms of the invention.

The carrier can comprise any and all solvents, diluents, or other liquid vehicle, dispersion or suspension aids, surface active agents, isotonic agents, thickening or emulsifying agents, preservatives, solid binders, lubricants, and the like, as suited to the particular dosage form desired. Remington's Pharmaceutical Sciences, Sixteenth Edition, E, W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials that can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose, starches such as corn starch and potato starch, cellulose and its derivatives such as sodium carboxymethyl cellulose, ethyl cellulose and cellulose acetate, powdered tragacanth, malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, buffering agents such as magnesium hydroxide and aluminum hydroxide, alginic acid, pyrogen-free water, isotonic saline, Ringer's solution, ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives, and antioxidants. Additional carriers include those described in U.S. Pat. No. 9,556,146 to Bassaganya-Riera et al.; U.S. Pat. No. 9,839,635 to Bassaganya-Riera et al.; U.S. Pat. No. 10,028,950 to Bassaganya-Riera et al.; U.S. Pat. No. 10,201,538 to Bassaganya-Riera et al.; U.S. Pat. No. 10,493,072 to Bassaganya-Riera et al.; U.S. Pat. No. 10,682,349 to Bassaganya-Riera et al.; U.S. Pat. No. 10,849,895 to Bassaganya-Riera et al; and US 2019/0160100 A1 to Bassaganya-Riera et al.

The pharmaceutical compositions can be used to deliver pharmaceutically effective amounts of one or more of the piperazine-1,4-diylbis((6-(1H-benzo[d]imidazo-2-yl)pyridine-2-yl)methanone) crystal forms of the invention to a subject. The subject can be a subject suffering from a chronic inflammatory, immune-mediated, or autoimmune disease. The crystal form of piperazine-1,4-diylbis((6-(1H-benzo[d]imidazo-2-yl)pyridine-2-yl)methanone) can be administered in an amount effective to treat the disease. The disease can comprise any disease or condition described in U.S. Pat. No. 9,556,146 to Bassaganya-Riera et al.; U.S. Pat. No. 9,839,635 to Bassaganya-Riera et al.; U.S. Pat. No. 10,028,950 to Bassaganya-Riera et al.; U.S. Pat. No. 10,201,538 to Bassaganya-Riera et al.; U.S. Pat. No. 10,493,072 to Bassaganya-Riera et al.; U.S. Pat. No. 10,682,349 to Bassaganya-Riera et al.; U.S. Pat. No. 10,849,895 to Bassaganya-Riera et al; and US 2019/0160100 A1 to Bassaganya-Riera et al. Examples include inflammatory bowel disease, such as ulcerative colitis and Crohn's disease. The route of administration can comprise any route described in U.S. Pat. No. 9,556,146 to Bassaganya-Riera et al.; U.S. Pat. No. 9,839,635 to Bassaganya-Riera et al.; U.S. Pat. No. 10,028,950 to Bassaganya-Riera et al.; U.S. Pat. No. 10,201,538 to Bassaganya-Riera et al.; U.S. Pat. No. 10,493,072 to Bassaganya-Riera et al.; U.S. Pat. No. 10,682,349 to Bassaganya-Riera et al.; U.S. Pat. No. 10,849,895 to Bassaganya-Riera et al; and US 2019/0160100 A1 to Bassaganya-Riera et al. The disease can also or alternatively comprise an inflammatory, immune-mediated, or autoimmune condition of a surface tissue such as the skin or mucosa (e.g., oral mucosa). Exemplary diseases include psoriasis, cutaneous lupus erythematosus, dermatomyositis, pemphigoid, pemphigus, scleroderma, vasculitis, epidermolysis bullosa acquisita, vitiligo, lichen planus, scleritis, dermatitis or eczema, erythema nodosum, pyoderma gangrenosum, skin fissures, acne, enterocutaneous fistula, skin tags, canker sores, acrodermatitis enteropathica, pyoderma vegetans, leukocytoclastic vasculitis, anal fissures, Sweet's syndrome, rosacea, alopecia, keratoderma blennorrhagica, rosacea, cold sores, urticaria, actinic keratosis, carbuncle, cellulitis, ichthyosis vulgaris, skin infection, malar rash, photosensitivity, livedo reticularis, livedo reticularis, oral and nasal ulcers, purpura, mucositis, hemorrhoids, burn, and sunburn. Administration in such cases can comprise topically administering the composition to a subject.

Form 2 of piperazine-1,4-diylbis((6-(1H-benzo[d]imidazo-2-yl)pyridine-2-yl)methanone) has a characteristic of having an increased confinement to the gastrointestinal tract after oral administration. Form 2 is therefore a preferred form for orally administering to a subject for the treatment of a disease of the gastrointestinal tract, such as a chronic inflammatory, immune-mediated, or autoimmune disease of the gastrointestinal tract. Exemplary chronic inflammatory, immune-mediated, or autoimmune disease of the gastrointestinal tract include inflammatory bowel disease, such as ulcerative colitis and Crohn's disease, and eosinophilic disorders of the gastrointestinal tract, such as eosinophilic esophagitis. The pharmaceutical composition comprising Form 2 can be administered in an amount effective to treat the disease of the gastrointestinal tract.

The terms "crystal form" and "crystalline form" are used interchangeably herein.

"$2\theta$ value" and grammatical variants thereof refer to values that would correspond to position $2\theta$ values as provided herein.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Characterization Methods
X-Ray Powder Diffraction (XRPD)

XRPD analysis was carried out, scanning the samples between 3 and 35° $2\theta$. The material was gently ground to release any agglomerates and loaded onto a multi-well plate with polymer film to support the sample. The multi-well plate was then placed into the diffractometer and analyzed using Cu K radiation ($\alpha 1$ $\lambda$=1.54060 Å; $\alpha 2$=1.54443 Å;

β=1.39225 Å; α1:α2 ratio=0.5) running in transmission mode (step size 0.0130° 2θ, step time 18.87 s) using 40 kV/40 mA generator settings. Data were visualized and analyzed.

Polarized Light Microscopy (PLM)

The presence of crystallinity (birefringence) was determined using a polarizing microscope, equipped with a camera and image capture software. All images were recorded using at 200× magnification using a 20× objective, unless otherwise stated.

Thermogravimetric Analysis (TGA)

Approximately, 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 350° C. during which time the change in sample weight was recorded along with any differential thermal events (DTA). Nitrogen was used as the purge gas, at a flow rate of 300 cm$^3$/min.

Differential Scanning Calorimetry (DSC)

Approximately, 5 mg of material was weighed into an aluminum DSC pan and sealed non-hermetically with a pierced aluminum lid. The sample pan was then loaded into a calorimeter, cooled, and held at 20° C. Once a stable heat-flow response was obtained, the sample and reference were heated to melting (if possible) at a scan rate of 10° C./min and the resulting heat flow response monitored. Nitrogen was used as the purge gas, at a flow rate of 50 cm$^3$/min.

Dynamic Vapor Sorption (DVS)

Approximately, 10 mg of sample was placed into a mesh vapor sorption balance pan and loaded into a DVS-1/DVS Intrinsic/DVS Advantage dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 min, maximum step length 500 min) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Gravimetric Vapor Sorption (GVS)

Approximately 10-20 mg of sample was placed into a mesh vapor sorption balance pan and loaded into a sorption analyzer balance. The sample was subjected to a ramping profile from 40-90% relative humidity (RH) at 10% increments, maintaining the sample at each step until a stable weight had been achieved (98% step completion, minimum step length 30 minutes, maximum step length 60 minutes) at 25° C. After completion of the sorption cycle, the sample was dried using the same procedure to 0% RH, and finally taken back to the starting point of 40% RH. Two cycles were performed. The weight change during the sorption/desorption cycles were plotted, allowing for the hygroscopic nature of the sample to be determined.

Variable Temperature X-Ray Powder Diffraction (VT-XRPD)

VT-XRPD analysis was carried out on a diffractometer equipped with a temperature chamber. The samples were scanned between 4 and 35 °2θ using Cu K radiation (α$_1$λ=1.54060 Å; α$_2$=1.54443 Å; β=1.39225 Å; α$_1$:α$_2$ ratio=0.5) running in Bragg-Brentano geometry (step size 0.008 °2θ) using 40 kV/40 mA generator settings.

Particle Size Distribution

Particle size distribution analysis was carried out using a particle size analyzer with a dispersion cell. Approximately 50 mg of sample was weighed into a 20 mL scintillation vial and 10 mL of dispersant was added. The sample was sonicated for 30 seconds, aspirated with a glass pipette, and then added to the dispersion unit. The sample was circulated for 30 seconds to allow the dispersion to stabilize.

Example 1. Crystal Form 0 of BT-11

Form 0 Preparation Methods

BT-11 free base was made as described in U.S. Pat. No. 10,028,950. A solution of 6-(1H-Benzimidazol-2-yl)pyridine-2-carboxylic acid (12 g) in DMF (100 mL) was cooled to 0° C., and then sequentially added EDC.HCl (1.5 eq), HOBt (1.5 eq) and DIPEA (1.2 eq, taken in volumes with density presumed). The mixture was stirred for 10 min at 0° C. Piperazine (0.5 eq) was added and the reaction mixture was allowed to warm to RT gradually and stirred for 16 h. After completion of the reaction (monitored by TLC, eluent: 10% MeOH in DCM), the reaction mixture was poured into ice-cold water (~300 mL), the precipitated solid was filtered, washed with ice-cold water and dried to get BT-11 (10 g, 75%) as pale brown solid. $^1$H NMR (400 MHz, DMSO-d$_6$), δ 13.0 (s, 1H), 12.8 (s, 1H), 8.38 (dd, 2H), 8.13 (dt, 2H), 7.73 (dd, 2H), 7.67 (d, 2H), 7.57 (dd, 2H), 7.25 (m, 4H), 3.90 (bs, 2H), 3.80 (bdd, 2H), 3.65 (bdd, 2H), 3.56 (bs, 2H). LCMS-ES 529.44 [M+H]$^+$, 265.46 [(M+2H)/2]$^{++}$.

Characterization

BT-11 free base was characterized via XRPD (FIG. 1). The free base was found to be crystalline. This was designated as Form 0 of BT-11. Indexing of Form 0 found the most probable space group to be P2$_1$/c monoclinic. Diffraction peaks are presented in Table 1. Reduced cell parameters are presented in Table 2.

TABLE 1

Diffraction peaks observed for Form 0 of BT-11.

| No. | Pos. [°2θ] | d-spacing [Å] | Height [cts] | Area [cts * °2θ] | Rel. Int [%] | h | k | l | Position Calc. [°2θ] |
|---|---|---|---|---|---|---|---|---|---|
| 1 | 9.4457 | 9.36336 | 329 | 24.91 | 10.43 | 0 | 2 | 0 | 9.0246 |
| 2 | 9.8533 | 8.97689 | 382.36 | 38.6 | 12.12 | 1 | 1 | −1 | 9.869 |
| 3 | 12.1867 | 7.26278 | 2204.02 | 250.31 | 69.84 | 2 | 0 | 0 | 12.4464 |
| 4 | 13.273 | 6.67074 | 495.74 | 43.79 | 15.71 | 2 | 1 | 0 | 13.244 |
| 5 | 14.3626 | 6.16704 | 458.7 | 40.52 | 14.54 | 2 | 1 | −1 | 14.0268 |
| 6 | 15.1595 | 5.84461 | 1339.35 | 135.21 | 42.44 | 1 | 0 | −2 | 15.072 |
| 7 | 15.5525 | 5.69779 | 3155.58 | 318.55 | 100 | 0 | 1 | 2 | 15.5991 |
| 8 | 16.0682 | 5.51606 | 355.8 | 44.9 | 11.28 | 2 | 2 | −1 | 16.0754 |
| 9 | 18.0954 | 4.9024 | 372.9 | 47.05 | 11.82 | 0 | 4 | 0 | 18.1059 |

TABLE 1-continued

Diffraction peaks observed for Form 0 of BT-11.

| No. | Pos. [°2θ] | d-spacing [Å] | Height [cts] | Area [cts * °2θ] | Rel. Int [%] | h | k | l | Position Calc. [°2θ] |
|---|---|---|---|---|---|---|---|---|---|
| 10 | 18.661 | 4.75509 | 430.41 | 48.88 | 13.64 | 3 | 0 | 0 | 18.7161 |
| 11 | 20.0651 | 4.4254 | 1003.62 | 126.64 | 31.8 | 1 | 4 | −1 | 20.1522 |
| 12 | 22.0855 | 4.02491 | 1317.64 | 166.27 | 41.76 | 2 | 4 | 0 | 22.0309 |
| 13 | 22.3527 | 3.9774 | 2340.55 | 295.35 | 74.17 | 2 | 3 | −2 | 22.2811 |
| 14 | 22.6134 | 3.93214 | 940.82 | 71.23 | 29.81 | 1 | 1 | −3 | 22.6404 |
| 15 | 23.1978 | 3.83437 | 329.57 | 41.59 | 10.44 | 3 | 3 | 0 | 23.1808 |
| 16 | 25.2815 | 3.52287 | 725.39 | 45.77 | 22.99 | 2 | 3 | 2 | 25.2468 |
| 17 | 25.9299 | 3.43624 | 269.83 | 47.67 | 8.55 | 2 | 5 | 0 | 25.9562 |
| 18 | 26.3756 | 3.37918 | 298.59 | 30.14 | 9.46 | 2 | 5 | −1 | 26.3747 |
| 19 | 28.1953 | 3.16509 | 1136.22 | 143.38 | 36.01 | 3 | 4 | 1 | 28.1945 |
| 20 | 31.0896 | 2.87672 | 766.25 | 87.02 | 24.28 | 4 | 4 | 0 | 31.0769 |

TABLE 2

Reduced cell parameters of Form 0 of BT-11

| Cell Parameters | Value |
|---|---|
| a sigma [Å] | 14.46 |
| b sigma [Å] | 19.58 |
| c sigma [Å] | 12.073 |
| alpha (sigma) [°] | 90.00 |
| beta (sigma) [°] | 100.67 |
| gamma (sigma) [°] | 90.00 |

Figure 2:
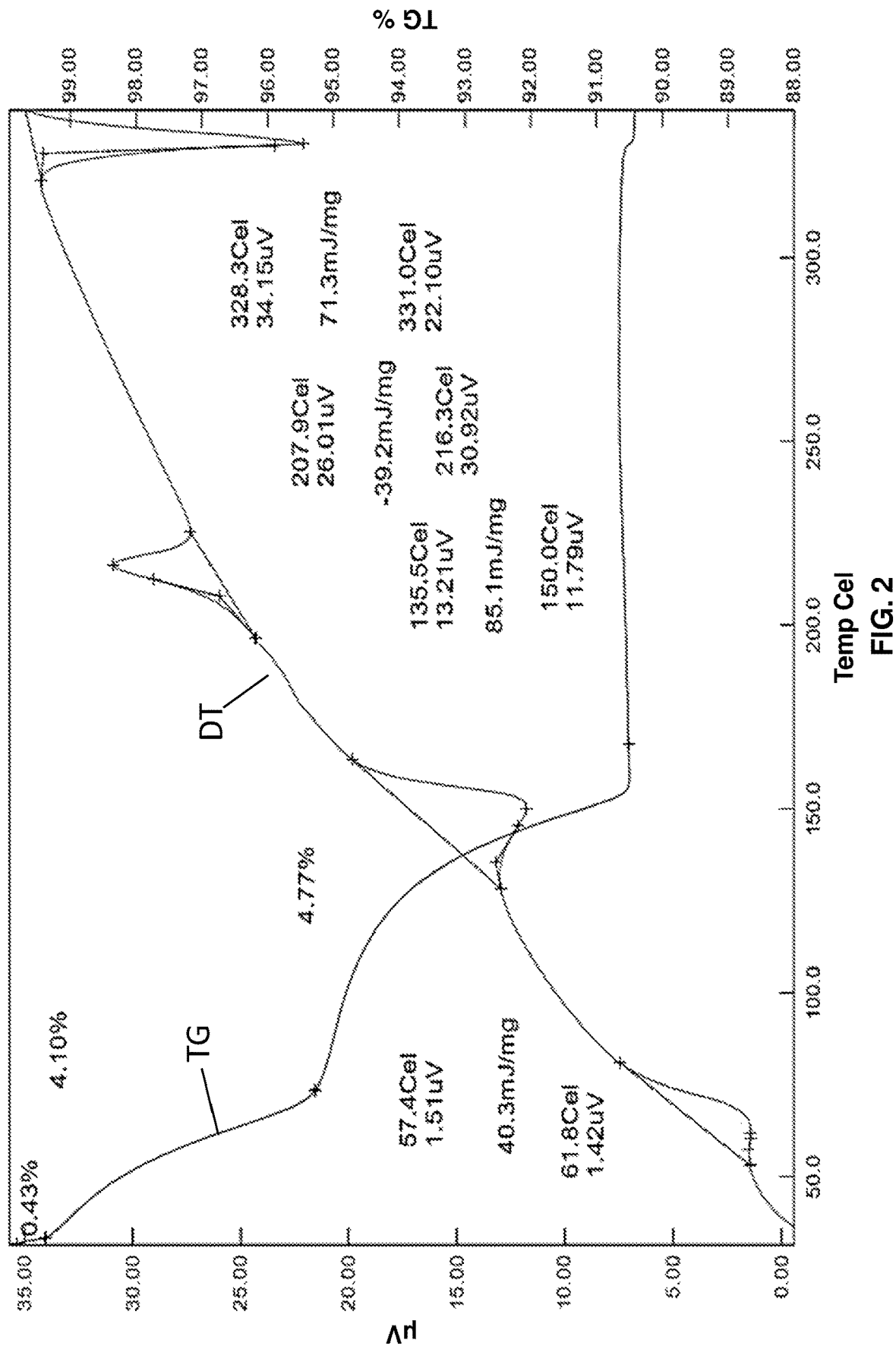
FIG. 2. Thermogravimetry/differential thermal analysis (TG/DTA) thermogram of BT-11 free base Form 0. The thermal gravimetric trace (TG) trace and differential thermal (DT) trace are indicated.

Form 0 of BT-11 was characterized via thermogravimetric analysis (FIG. 2). The thermal gravimetric trace (TG) showed consecutive losses in mass from the outset of heating up to ~160° C. Additionally, there was a 4.1% mass loss of approximately 1.3 equiv. of water (broad endothermic event (onset 57° C.) associated with this loss in mass. There was a 4.8% mass loss above 60° C., which may be a result of dehydration (1.5 equiv. of water). This is indicative of a broad endothermic event (onset 136° C.) associated with this second loss in mass. An exothermic event (onset 208° C.) followed by a sharp endothermic event (onset 328° C.) occurred. PSD analysis (FIG. 3) showed that Form 0 had a $d_{90}$ of 19.8 μm, $d_{50}$ of 6.3 μm and $d_{10}$ of 0.2 μm.

Example 2. Crystal Form 1 of BT-11

Form 1 Preparation Methods

Method A. BT-11 dihydrochloride was made as described in U.S. Pat. No. 10,028,950. A suspension of BT-11 free base (1.0 eq) in minimal amount of MeOH (5 mL) was cooled to 0° C., was added 4 M methanolic HCl (excess, 15 mL/1 g) dropwise over a period of 15-20 min. The mixture was allowed gradually to warm to RT for 3 h. After completion of the reaction (monitored by TLC, eluent: 10% MeOH in $CH_2Cl_2$), the volatiles were evaporated under reduced pressure. The crude material was washed with 10% MeOH in $CH_2Cl_2$ and lyophilized to get an off-white solid (850 mg, 75%). $^1$H NMR (400 MHz, DMSO-$d_6$), δ 8.58 (dd, 2H), 8.29 (dt, 2H), 7.83 (m, 6H), 7.44 (bd, 4H), 3.91 (bs, 2H), 3.81 (bm, 2H), 3.64 (bm, 2H), 3.55 (bs, 2H). LCMS-ES 529.56 [M+H]$^+$.

Method B. A suspension of BT-11 free base in minimal ethylacetate was cooled to −5 to 0 C. 4M HCl in ethylacetate was added over a period of 25 to 30 minutes. Reaction mass was maintained at −5 to 5 C for 4 to 5 hours. After completion of the reaction, the wet material was washed with ethylacetate and dried under vacuum. $^1$H NMR (400 MHz, DMSO-$d_6$), δ 8.58 (dd, 2H), 8.29 (dt, 2H), 7.83 (m, 6H), 7.44 (bd, 4H), 3.91 (bs, 2H), 3.81 (bm, 2H), 3.64 (bm, 2H), 3.55 (bs, 2H). LCMS-ES 529.56 [M+H]$^+$.

Characterization

The BT-11 dihydrochloride preparations were characterized via XRPD (FIGS. 4A and 4B). The material was found to be crystalline and designated as Form 1. Diffraction peaks are presented in Table 3. Reduced cell parameters are presented in Table 4.

TABLE 3

Diffraction peaks observed for Form 1 of BT-11 dihydrochloride.

| No. | Pos. [°2θ] | d-spacing [Å] | Height [cts] | Area [cts * °2θ] | Rel. Int [%] | h | k | l | Position Calc. [°2θ] |
|---|---|---|---|---|---|---|---|---|---|
| 1 | 5.8988 | 14.98305 | 685.76 | 77.88 | 46.89 | 0 | 1 | 0 | 5.8829 |
| 2 | 9.7766 | 9.04711 | 980.73 | 111.38 | 67.06 | 0 | 0 | 1 | 9.796 |
| 3 | 10.6542 | 8.30379 | 478.95 | 48.35 | 32.75 | 0 | 1 | −1 | 10.6804 |
| 4 | 11.7931 | 7.5043 | 434.36 | 38.37 | 29.7 | 0 | 2 | 0 | 11.7814 |
| 5 | 14.1862 | 6.24333 | 628.01 | 63.4 | 42.94 | 1 | −1 | 0 | 14.1623 |
| 6 | 15.6073 | 5.67788 | 148.17 | 29.92 | 10.13 | 1 | 1 | −1 | 15.2801 |
| 7 | 16.4538 | 5.38765 | 173.48 | 21.89 | 11.86 | 0 | 2 | 1 | 16.4013 |
| 8 | 17.763 | 4.99338 | 174.9 | 35.31 | 11.96 | 1 | 0 | 1 | 17.8131 |
| 9 | 18.9757 | 4.67692 | 537.95 | 81.46 | 36.78 | 0 | 3 | −1 | 18.9875 |
| 10 | 19.6112 | 4.52678 | 962.24 | 85 | 65.79 | 0 | 0 | 2 | 19.6645 |
| 11 | 20.6095 | 4.30971 | 153.99 | 31.09 | 10.53 | 1 | −2 | 1 | 20.4799 |
| 12 | 21.5298 | 4.12752 | 170.69 | 25.85 | 11.67 | 0 | 3 | 1 | 21.4947 |
| 13 | 22.2248 | 4 | 687.43 | 69.4 | 47 | 1 | 3 | 0 | 22.1861 |
| 14 | 23.1555 | 3.84129 | 1462.49 | 129.18 | 100 | 1 | 2 | −2 | 23.0512 |
| 15 | 24.3124 | 3.66105 | 1438.67 | 127.08 | 98.37 | 0 | 4 | −1 | 24.3218 |

TABLE 3-continued

Diffraction peaks observed for Form 1 of BT-11 dihydrochloride.

| No. | Pos. [°2θ] | d-spacing [Å] | Height [cts] | Area [cts * °2θ] | Rel. Int [%] | h | k | l | Position Calc. [°2θ] |
|---|---|---|---|---|---|---|---|---|---|
| 16 | 26.0833 | 3.41638 | 151.74 | 38.29 | 10.38 | 2 | 0 | 0 | 26.1062 |
| 17 | 28.1209 | 3.17329 | 728.59 | 165.49 | 49.82 | 2 | 2 | −1 | 28.1666 |
| 18 | 28.6645 | 3.11433 | 211.91 | 32.09 | 14.49 | 0 | 4 | −2 | 28.646 |
| 19 | 31.0084 | 2.88407 | 306.81 | 46.46 | 20.98 | 2 | 3 | −1 | 31.0171 |
| 20 | 33.2962 | 2.69095 | 146.15 | 36.88 | 9.99 | 0 | 5 | −2 | 33.3586 |

TABLE 4

Reduced cell parameters of Form 1 of BT-11 dihydrochloride.

| Cell Parameters | Value |
|---|---|
| a sigma [Å] | 6.97 |
| b sigma [Å] | 15.17 |
| c sigma [Å] | 9.31 |
| alpha (sigma) [°] | 98.26 |
| beta (sigma) [°] | 101.74 |
| gamma (sigma) [°] | 89.23 |

BT-11 Form 1 was characterized via PLM. The PLM images showed that the material consisted of aggregated particles with no clear morphology. Additionally, the material appeared birefringent under polarized light, indicative of a crystalline material.

Figure 5:
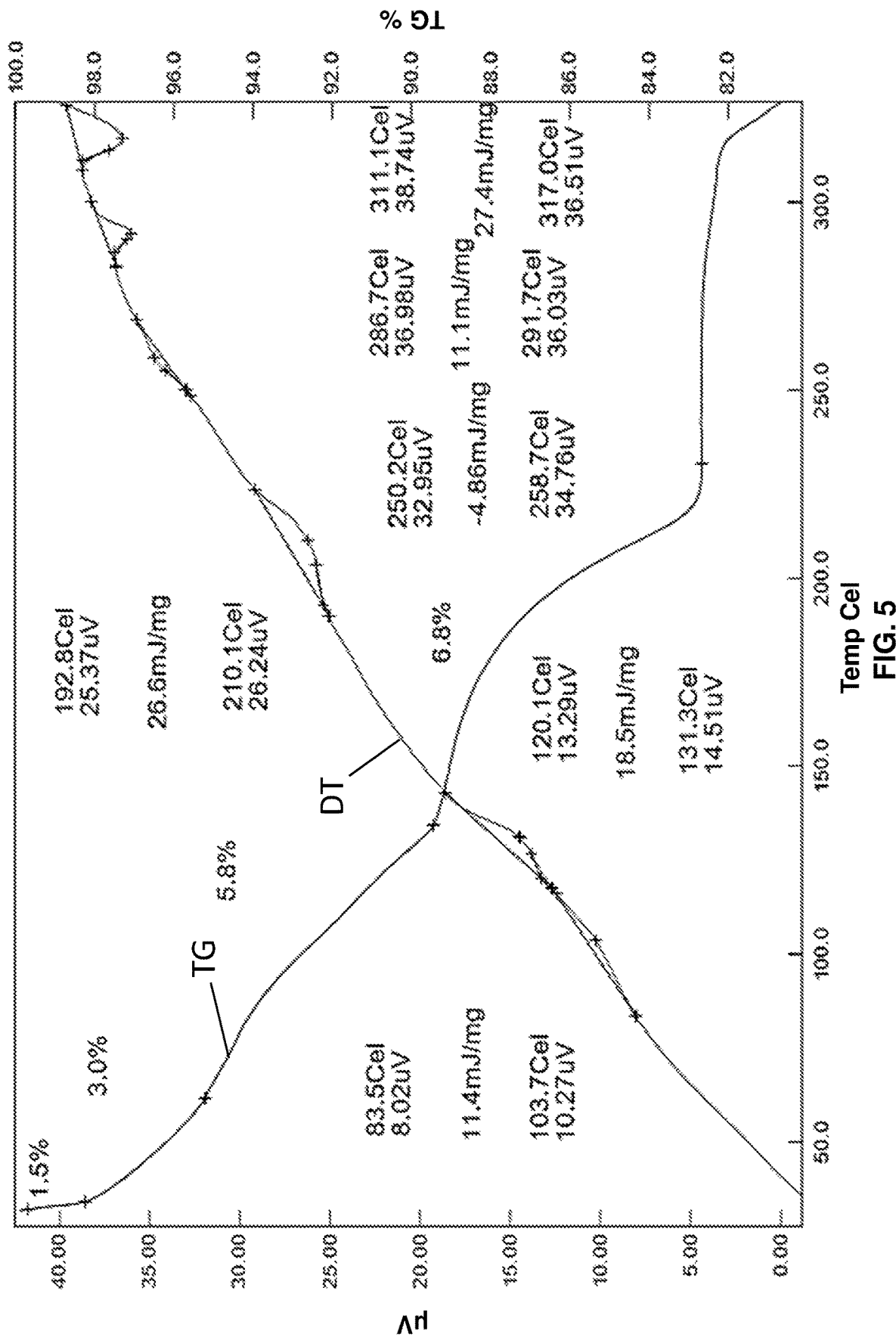
FIG. 5. TG/DTA thermogram of BT-11 dihydrochloride Form 1. The thermal gravimetric trace (TG) trace and differential thermal (DT) trace are indicated.

BT-11 Form 1 was characterized via thermal gravimetric trace (FIG. 5). The thermal gravimetric trace showed consecutive losses in mass observed from the outset of heating up to ~220° C. Weak endothermic events were observed (onsets of ~84 and 120° C., respectively) around these initial mass losses. The differential thermogram (TG) showed a weak exothermic event (onset 250° C.) followed by two endothermic events (onsets of 287 and 311° C.). No further loss in mass until second endothermic event.

Figure 6A:
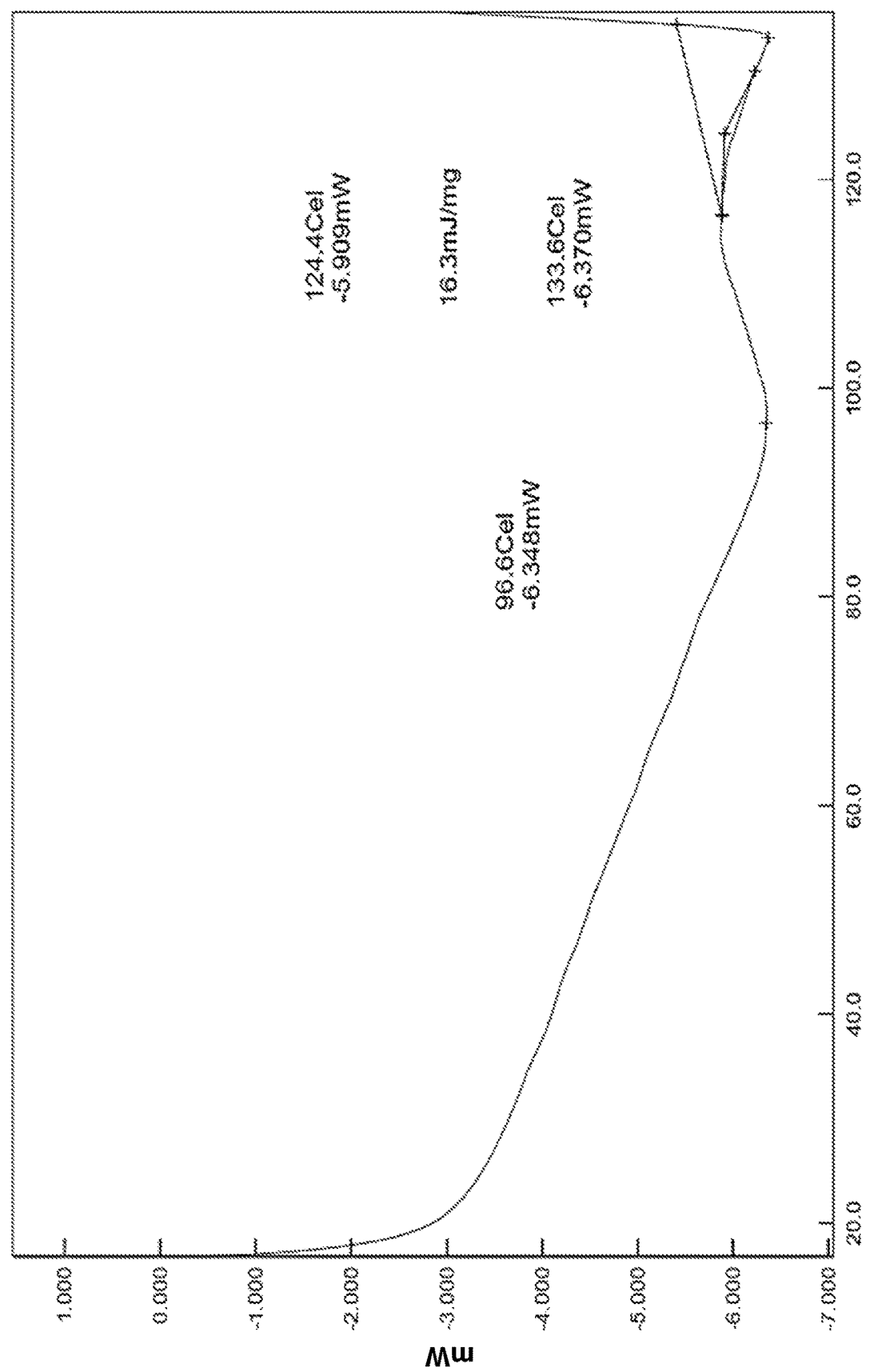
FIGS. 6A-6C. Differential scanning calorimetry (DSC) thermograms of BT-11 dihydrochloride Form 1 at a first heating step (FIG. 6A), cooling step (FIG. 6B), and second heating step (FIG. 6C).
Figure 6B:
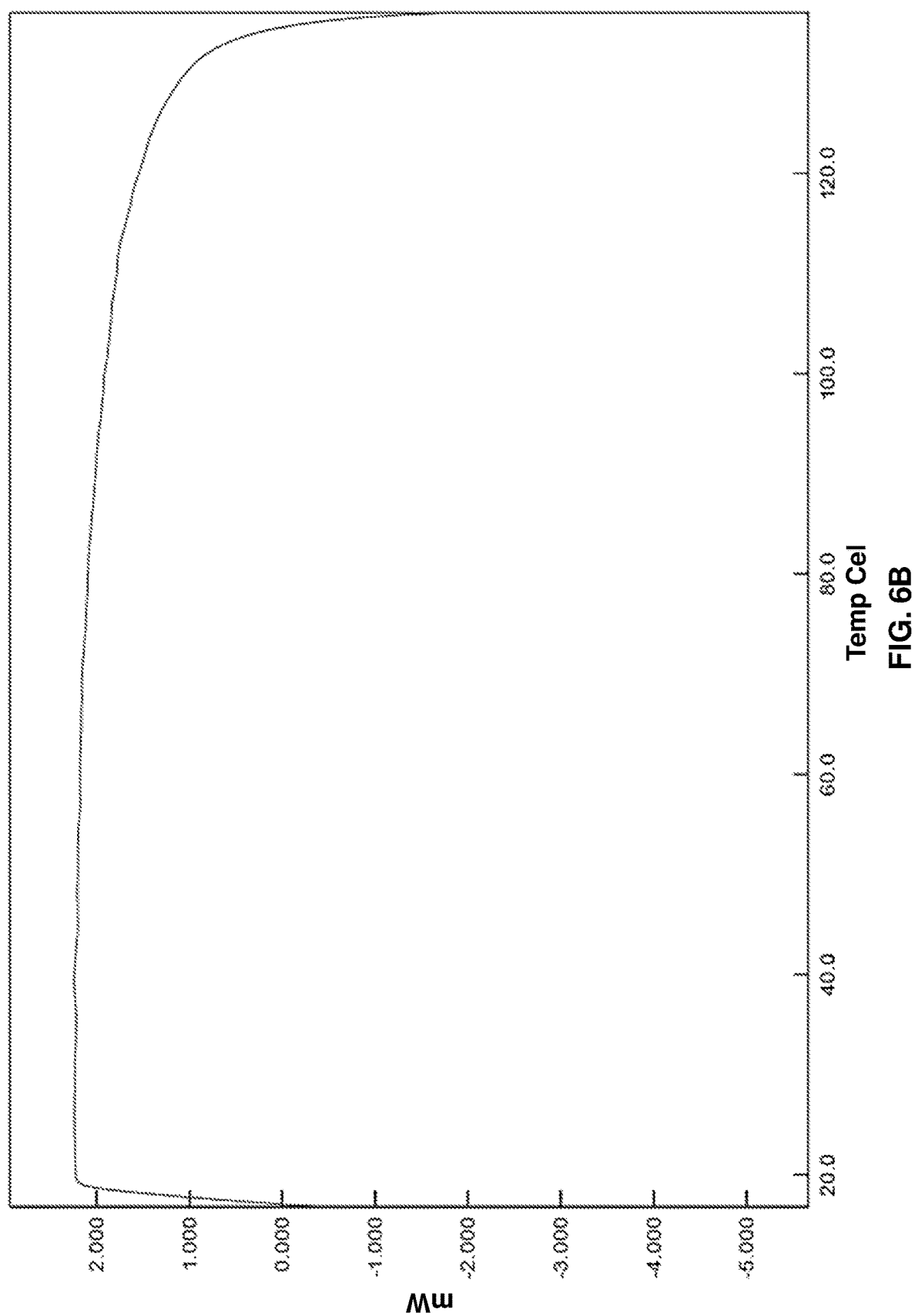
Figure 6C:
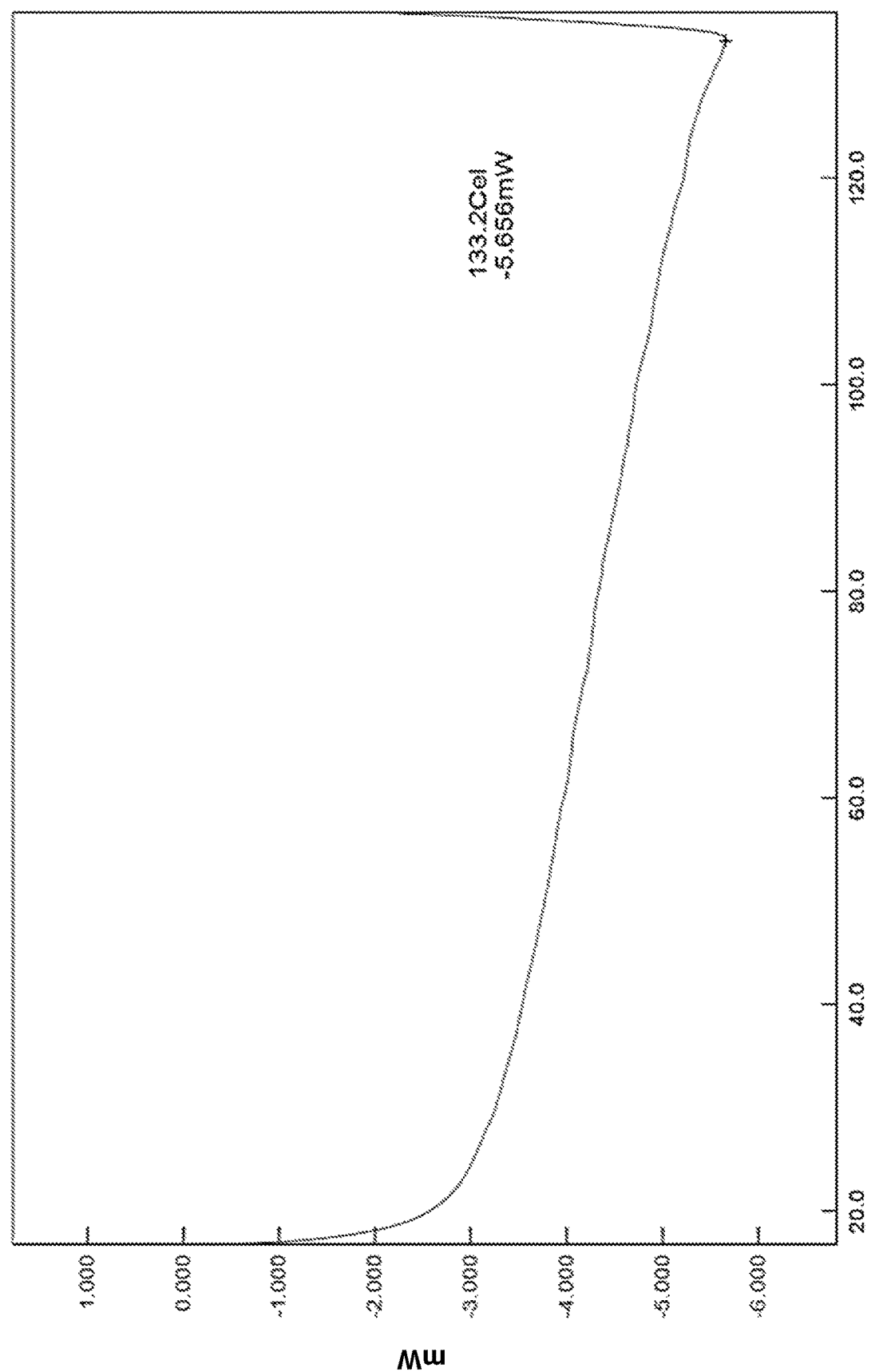

BT-11 Form 1 was characterized via DSC (FIGS. 6A-6C). The material was heated in the DSC to around 130° C. The material was then cooled and re-heated to check for recrystallization. In FIG. 6A at the first heat (20-130° C.), two broad endothermic events observed (around ~97° C. and an onset of ~124° C., respectively) which correlated with the two weak endothermic events observed in the TG/DTA. In FIG. 6B at the cooling step (130-20° C.), no thermal events were observed on cooling. In FIG. 6C at the second heat (20-130° C.), no thermal events were observed on re-heating.

Figure 7A:
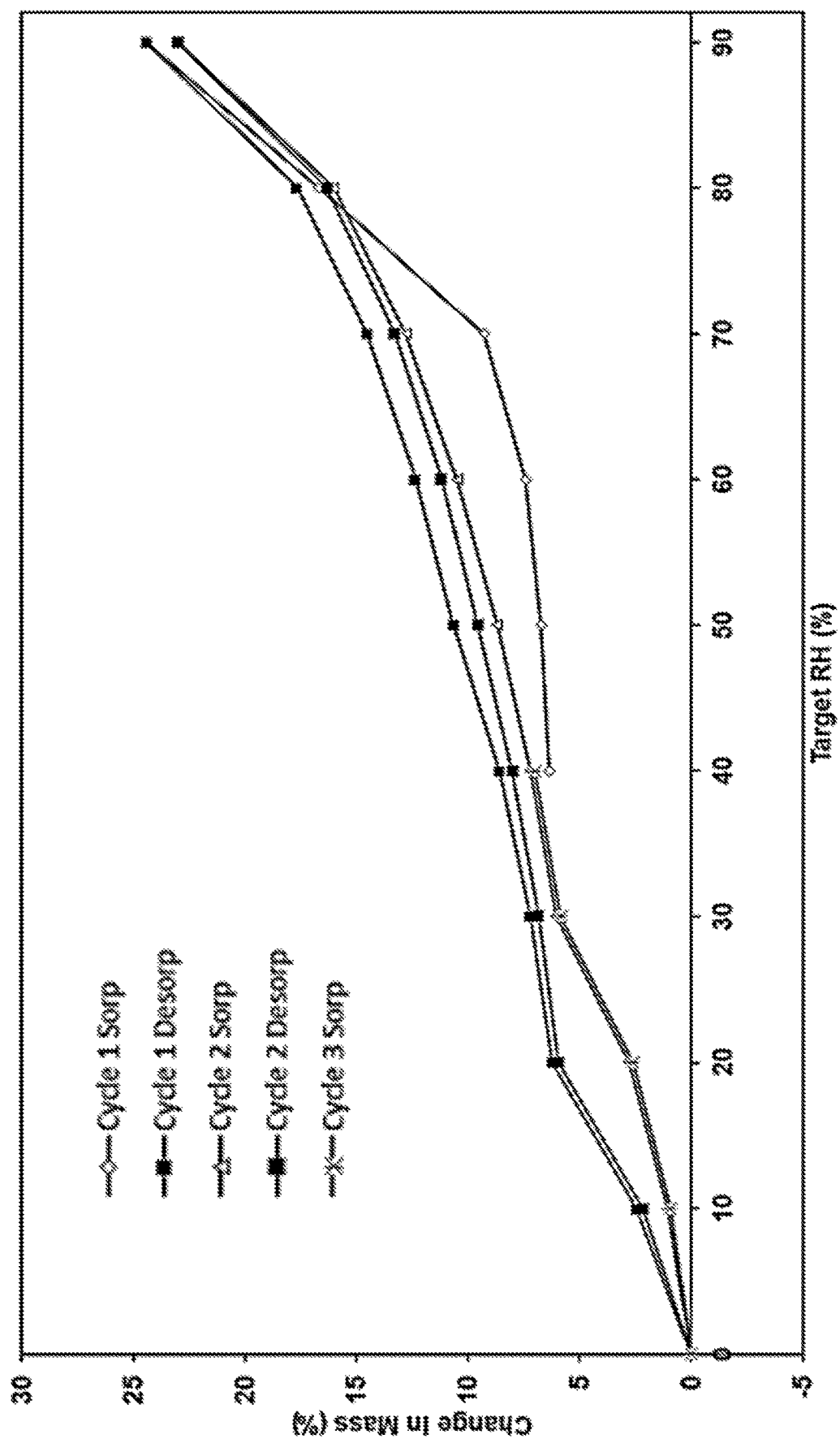
FIGS. 7A and 7B. Dynamic vapor sorption (DVS) isotherm (double cycle) (FIG. 7A) and DVS kinetic plot (FIG. 7B) for the analysis of BT-11 dihydrochloride Form 1.
Figure 7B:
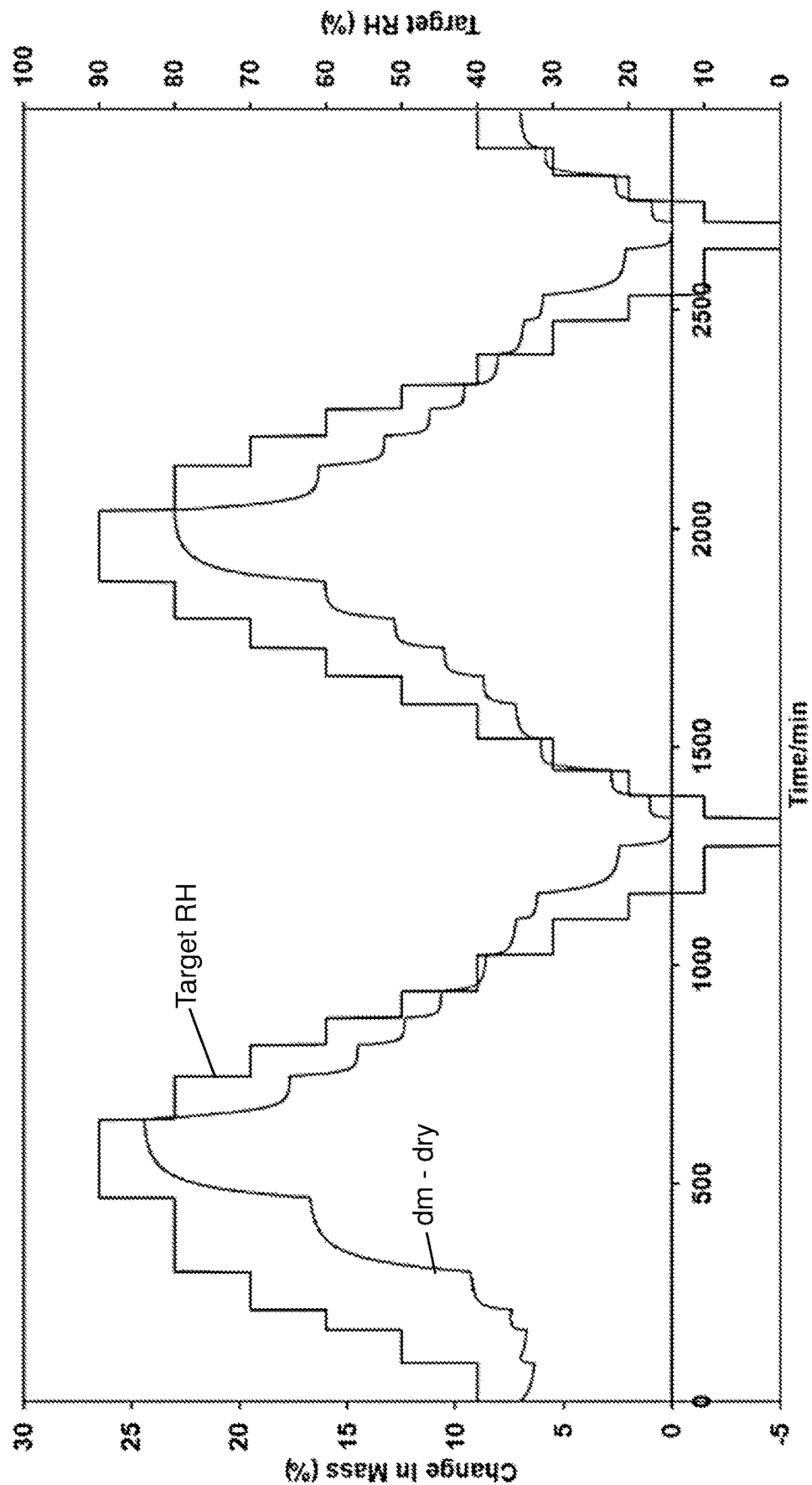

BT-11 Form 1 was characterized via DVS (FIG. 7A and FIG. 7B). In FIG. 7A, DVS analysis showed a total 24% mass increase up to 90% RH. The material was hygroscopic, 6.0% of total mass was lost below 20% RH. Rehydration appeared slower than dehydration. In FIG. 7B, no evidence of re-crystallization or form change occurring during the DVS experiment. Dehydration and re-hydration steps were not very pronounced.

Figure 8:
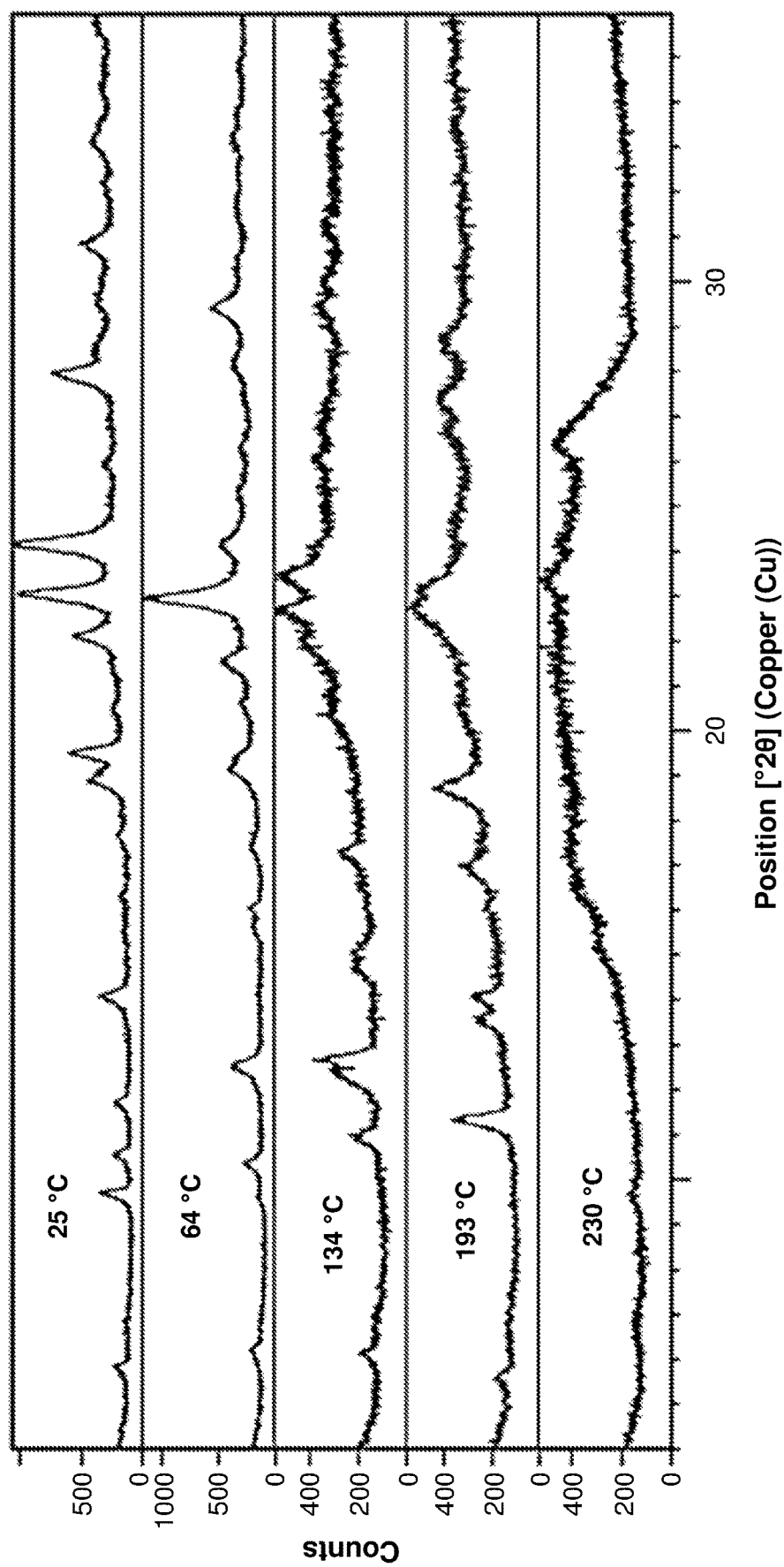
FIG. 8. Variable temperature X-ray powder diffraction (VT-XRPD) of BT-11 dihydrochloride Form 1.
Figure 9:
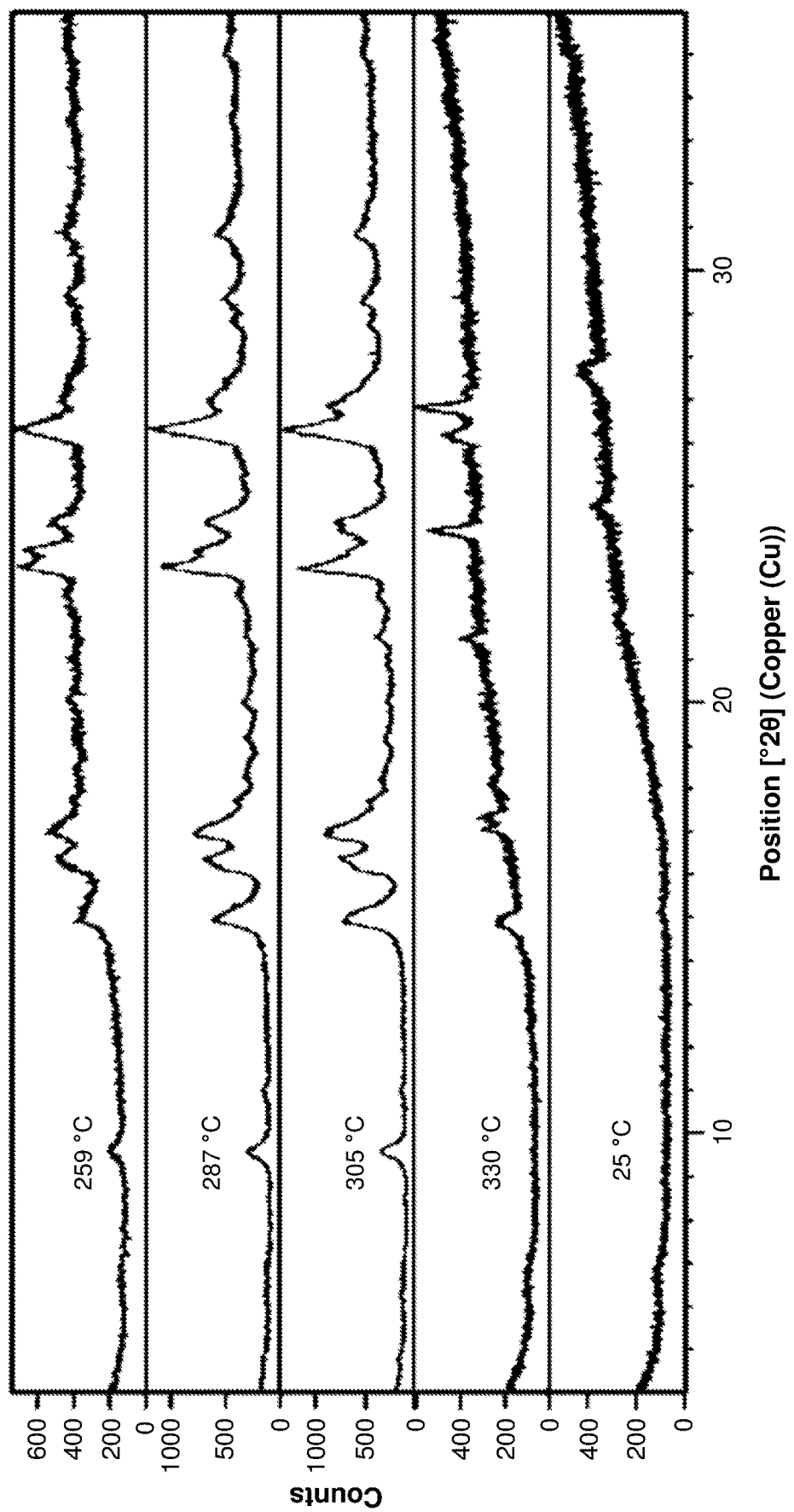
FIG. 9. VT-XRPD of BT-11 dihydrochloride Form 1.

BT-11 Form 1 was characterized by VT-XRPD analysis (FIG. 8 and FIG. 9). In FIG. 8, several new patterns were observed during the VT-XRPD experiment (each represented by a different color). After each mass loss or at each thermal event observed in the TG/DTA, a new (poorly crystalline) pattern was produced. The material appeared amorphous after the possible salt disproportionation.

In FIG. 9, a new pattern was produced, above 250° C., where the material had potentially fully disproportionated and an exothermic event was noted. Post-degradation, a poorly crystalline pattern was observed but was found to be predominantly amorphous when cooled back to 25° C.

BT-11 Form 1 was characterized by PSD. PSD analysis (FIG. 10) showed that the received material had a $d_{90}$ of 40.8 μm, $d_{50}$ of 0.5 μm and $d_{10}$ of 0.1 μm.

Form 1 was also obtained from dried material from a toluene slurry. Toluene was added to BT-11 dihydrochloride in a 100:1 (v/w) ratio to form a slurry. Slurry was thermally cycled with agitation for 72 hours between ambient temperature for 4 hours followed by 40° C. for 4 hours. Solid material was isolated by filtration and dried at 40° C. for 2 hours.

Example 3. Crystal Form 2 of BT-11

Form 2 Preparation Methods

Method I. Methanol:water (80:20) was added to BT-11 dihydrochloride in a 40:1 (v/w) ratio to form a slurry. Slurry was then thermally cycled with agitation for 72 hours between ambient temperature for 4 hours followed by 40° C. for 4 hours. Solid material was isolated by filtration and dried at 40° C. for 2 hours. Dried material was analyzed by XRPD to have a unique crystalline form, designated to be Form 2.

Method II. 2-ethoxyethanol was added to BT-11 dihydrochloride in a 100:1 (v/w) ratio to form a slurry. Slurry was then thermally cycled with agitation for 72 hours between ambient temperature for 4 hours followed by 40° C. for 4 hours. Solid material was isolated by filtration and dried at 40° C. for 2 hours. Dried material was analyzed by XRPD to have a unique crystalline form, designated to be Form 2.

Method III. Methyl isobutyl ketone was added to BT-11 dihydrochloride in a 100:1 (v/w) ratio to form a slurry. Slurry was then thermally cycled with agitation for 72 hours between ambient temperature for 4 hours followed by 40° C. for 4 hours. Solid material was isolated by filtration and dried at 40° C. for 2 hours. Dried material was analyzed by XRPD to have a unique crystalline form, designated to be Form 2.

Method IV. BT-11 dihydrochloride was added to methanol:water (80:20) in a 1:40 (w/v) or 1:16 (w/v) ratio to form slurries under stirring at 20° C. Slurries were temperature cycled between 20° C. and 50° C. for 48 hours, at a rate of 0.1° C./min with a hold of 4 hours at each temperature. Solid material was isolated by filtration and dried at 40° C. under vacuum for 65 hours. Dried material was analyzed by XRPD to have a unique crystalline form, designated to be Form 2.

Method V. Methanol:water (80:20) was added to BT-11 dihydrochloride in a 1:20 (w/v) ratio to form slurries under stirring at 22° C. Slurries were temperature cycled between 30° C. and 50° C. for 48 hours, at a rate of 0.1° C./min with a hold of 4 hours at each temperature. Solid material was isolated by filtration and dried at 40° C. under vacuum for 20 hours. Dried material was analyzed by XRPD to have a unique crystalline form, designated to be Form 2.

Method VI. N-methylpyrrolidone (NMP) or a 90:10 (v/v) mixture of NMP:methanol were added to BT-11 free base in 24:1 or 32:1 (v/w) ratios, respectively, to form slurries by stirring for 1 hour at 50° C. The temperature was decreased to 40° C., over approximately 10 minutes. BT-11 dihydrochloride Form 2 was seeded into the mixture (6% weight). 0.55 equivalents of HCl were added dropwise. After approximately 5 minutes, an additional 2% weight of BT-11 dihydrochloride Form 2 was added. The slurries were stirred at 40° C. for approximately 10 minutes. 1.65 equivalents of HCl were added dropwise. The slurries were stirred at 40° C. for ca. 1 hour prior to cooling to 5° C. at a rate of 0.1° C./min and holding at 5° C. for approximately 18 hours. Solid materials were filtered and dried under vacuum at approximately 40° C. for approximately 21 hours. Isolated materials were slurried in methanol:water (80:20) in a 1:16 (w/v) ratio. The slurries were temperature cycled between 20° C. and 50° C. for ca. 48 hours at a rate of 0.1° C./min, with a hold of 4 hours at each temperature for 3 cycles. Solid materials were filtered and dried under vacuum at approximately 40° C. for approximately 20 hours. Isolated material analyzed by XRPD to have a unique crystalline form, designated to be Form 2.

Method VII. N-methylpyrrolidone:methanol:water (51:40:9) was added to BT-11 free base in a 53:1 (v/w) ratio to form a slurry by stirring for 1 hour at 50° C. BT-11 dihydrochloride Form 2 was seeded into the mixture (approximately 4% weight). Approximately 2.2 equivalents of HCl were added dropwise. An additional approximate 4% weight of BT-11 dihydrochloride Form 2 was added. The slurry was stirred at 50° C. for approximately 18 hours prior to cooling to 5° C. at a rate of 0.1° C./min and holding at 5° C. for approximately 18 hours. Solid materials were filtered. Isolated material analyzed by XRPD to have a unique crystalline form, designated to be Form 2.

Method VIII. N-methylpyrrolidone:methanol:water (51:40:9) or NMP:ethyl acetate (81:19) were added to BT-11 free base in 53:1 and 63:1 (v/w) ratios, respectively, to form slurries by stirring for 1 hour at 50° C. BT-11 dihydrochloride Form 2 was seeded into the mixture (approximately 4% weight). Approximately 2.2 equivalents of HCl were added dropwise. An additional approximate 4% weight of BT-11 dihydrochloride Form 2 was added. The slurry was stirred at 50° C. for approximately 18 hours prior to cooling to 5° C. at a rate of 0.1° C./min and holding at 5° C. for approximately 18 hours. Solid materials were filtered. Isolated materials were slurried in methanol:water (80:20) in approximately equal volume to the original solvent system and stirred at 50° C. for approximately 2 hours. The slurries were then cooled from 50° C. to 5° C. at a rate of 0.26° C./min. Solid materials were filtered and washed twice with 10 volumes of methanol:water (80:20). Isolated material was dried under vacuum at approximately 40° C. for approximately 64 hours. Isolated material analyzed by XRPD to have a unique crystalline form, designated to be Form 2.

Method IX. N-methylpyrrolidone:methanol (75:25) was added to BT-11 free base in a 42:1 (v/w) ratio to form a slurry by stirring for 1 hour at 50° C. BT-11 dihydrochloride Form 2 was seeded into the mixture (approximately 4% weight). Approximately 2.2 equivalents of HCl were added dropwise. An additional approximate 4% weight of BT-11 dihydrochloride Form 2 was added. The slurry was stirred at 50° C. for approximately 18 hours prior to cooling to 5° C. at a rate of 0.1° C./min and holding at 5° C. for approximately 18 hours. Solid materials were filtered. Isolated materials were slurried in methanol:water (80:20) in approximately equal volume to the original solvent system and stirred at 50° C. for approximately 2 hours. The slurry was cooled from 50° C. to 5° C. at a rate of 0.26° C./min. Solid materials were filtered and washed twice with 10 volumes of methanol:water (80:20). Isolated material was dried under vacuum at approximately 40° C. for approximately 64 hours. Isolated material was slurried in methanol:water (80:20) in a 1:16 (w/v) ratio. The slurry was temperature cycled between 20° C. and 50° C. for ca. 48 hours at a rate of 0.1° C./min with a hold of 4 hours at each temperature for 3 cycles. Solid material was filtered and analyzed by XRPD to have a unique crystalline form, designated to be Form 2.

Method X. N-methylpyrrolidone, NMP:water (90:10), NMP:methanol:water (51:40:9), or DMSO:methanol:water (50:40:10) were added to BT-11 free base in 23:1, 20:1, 40:1, or 37:1 (v/w) ratios to form slurries by stirring for 1 hour at 55° C. BT-11 dihydrochloride Form 2 was seeded into the mixture (approximately 0% to 10% weight). Approximately 2.2 equivalents of HCl were added dropwise. An additional approximate 0% to 5% weight of BT-11 dihydrochloride Form 2 was added. The slurry was stirred at 55° C. for approximately 5 hours prior to cooling to 5° C. at a rate of 0.1° C./min and holding at 5° C. for approximately 20 hours. Solid materials were filtered. Isolated materials from NMP were washed in NMP. Isolated materials from the other solvent systems were washed once with methanol. Isolated material was dried under vacuum at approximately 40° C. for approximately 38 hours and analyzed by XRPD to have a unique crystalline form, designated to be Form 2.

Method XI. N-methylpyrrolidone:water (90:10) was added to BT-11 free base in a 17:1 (v/w) ratio to form a slurry by stirring for 1 hour at 60° C. Approximately 2.2 equivalents of HCl were added dropwise in three aliquots. After each aliquot, 1% to 5% weight of BT-11 dihydrochloride Form 2 was added as seed. The slurry was stirred at 60° C. for approximately 21 hours prior to cooling to 5° C. at a rate of 0.25° C./min and holding at 5° C. for approximately 5 hours. Solid materials were filtered. Isolated materials were washed once with methanol. Isolated material was dried under vacuum at approximately 40° C. for approximately 64 hours and analyzed by XRPD to have a unique crystalline form, designated to be Form 2.

Method XII. DMSO:water (90:10) was added to BT-11 free base in a 17:1 (v/w) ratio to form a slurry by stirring for 1 hour at 60° C. Approximately 2.2 equivalents of HCl were added dropwise in a single aliquot. Approximately 6% weight of BT-11 dihydrochloride Form 2 was added as seed. The slurry was stirred at 60° C. for approximately 21 hours prior to cooling to 5° C. at a rate of 0.25° C./min and holding at 5° C. for approximately 5 hours. Solid materials were filtered. Isolated materials were washed once with methanol. Isolated material was dried under vacuum at approximately 40° C. for approximately 64 hours and analyzed by XRPD to have a unique crystalline form, designated to be Form 2.

Method XIII. N-methylpyrrolidone:water (90:10) was added to BT-11 free base in a 17:1 (v/w) ratio to form a slurry by stirring for 1 hour at 60° C. Approximately 2.2 equivalents of HCl were added dropwise in three aliquots. After each aliquot, 0.4% to 1% weight of BT-11 dihydrochloride Form 2 was added as seed. The slurry was stirred at 60° C. for approximately 21 hours prior to cooling to 5° C. at a rate of 0.25° C./min and holding at 5° C. for approximately 4 hours. Solid materials were filtered. Isolated materials were washed twice with methanol. Isolated material was dried under vacuum at approximately 40° C. for approximately 64 hours and analyzed by XRPD to have a unique crystalline form, designated to be Form 2.

Method XIV. DMSO:water (90:10) was added to BT-11 free base in a 34:1 (v/w) ratio to form a slurry by stirring for 1 hour at 60° C. Approximately 2.2 equivalents of HCl were added dropwise in a single aliquot. Approximately 3.4% weight of BT-11 dihydrochloride Form 2 was added as seed in two aliquots. The slurry was stirred at 60° C. for approximately 21 hours prior to cooling to 5° C. at a rate of 0.25° C./min and holding at 5° C. for approximately 5 hours. Solid materials were filtered. Isolated materials were washed twice with methanol. Isolated material was dried under vacuum at approximately 40° C. for approximately 64 hours and analyzed by XRPD to have a unique crystalline form, designated to be Form 2.

Method XV. NMP:water (90:10) was added to BT-11 free base in a 15:1 (v/w) ratio to form a slurry by stirring at 65° C. for approximately 45 minutes. Slurry was cooled to 60° C. over approximately 5 minutes. Approximately 1.1 equivalents of HCl was added to the slurry at a rate of 0.9 volumes/hour. 2% weight of BT-11 dihydrochloride Form 2 was added. After 1 hour, approximately 1.1 equivalents of HCl was added in 4 aliquots at a rate of 0.46 volumes/hour, pausing the acid addition between each aliquot for approximately 20 minutes. The slurry was stirred at 60° C. for approximately 18 hours. The experiment was cooled to 5° C. at a rate of 0.1° C./min and held at 5° C. for 20 hours. Solid material was filtered and washed with 2 volumes of methanol. Wet solid was dried under vacuum at 40° C. for approximately 82 hours. Isolated material was analyzed by XRPD to have a unique crystalline form, designated to be Form 2.

Method XVI. DMSO:methanol:water (50:40:10) was added to BT-11 free base in a 34:1 (v/w) ratio to form a slurry by stirring at 65° C. for approximately 45 minutes. Approximately 2.2 equivalents of HCl was added to the slurry at a rate of 4.6 volumes/hour. Slurry was cooled to 60° C. over approximately 5 minutes. 2% weight of BT-11 dihydrochloride Form 2 was added. The slurry was stirred at 60° C. for approximately 18 hours. The experiment was cooled to 5° C. at a rate of 0.1° C./min and held at 5° C. for 18 hours. Solid material was filtered and washed with 2 volumes of methanol. Wet solid was dried under vacuum at 40° C. for approximately 82 hours. Isolated material was analyzed by XRPD to have a unique crystalline form, designated to be Form 2.

Method XVII. DMSO:methanol:water (50:40:10) was added to BT-11 free base in a 40:1 (v/w) ratio to form a slurry by stirring at 65° C. for approximately 1 hour. Approximately 2.63 equivalents of HCl was added to the slurry dropwise over 20 minutes. Slurry was cooled to 60° C. over approximately 5 minutes. 2% weight of BT-11 dihydrochloride Form 2 was added. The slurry was stirred at 60° C. for approximately 8 hours. The experiment was cooled to 20° C. at a rate of 0.1° C./min and held at 20° C. for 10 hours. The slurry was heated to 50° C. at a rate of 0.5° C./min and held at 50° C. for 4 hours. The slurry was cooled to 5° C. at 0.1° C./min and held at 5° C. for 3 hours. Solid material was filtered and washed with 2 volumes of methanol. Wet solid was dried under vacuum at 40° C. for approximately 82 hours. Isolated material was analyzed by XRPD to have a unique crystalline form, designated to be Form 2.

Method XVIII. DMSO:methanol:water (50:40:10) was added to BT-11 free base in a 40:1 (v/w) ratio to form a slurry by stirring at 65° C. for approximately 1 hour. Approximately 2.63 equivalents of HCl was added to the slurry dropwise over 20 minutes. Slurry was cooled to 60° C. over approximately 5 minutes. 2% weight of BT-11 dihydrochloride Form 2 was added. The slurry was stirred at 60° C. for approximately 3 hours. Water was added at a rate of 2 volumes/hour at 60° C. to reach a solvent system of 34:27:39 and the slurry was stirred for an additional 1.5 hours. The slurry was cooled to 5° C. at 0.1° C./min and held at 5° C. for 8 hours. Solid material was filtered and washed with 2 volumes of methanol. Wet solid was dried under vacuum at 40° C. for approximately 86 hours. Isolated material was analyzed by XRPD to have a unique crystalline form, designated to be Form 2.

Method XIX. DMSO:methanol:water (50:40:10) was added to BT-11 free base in a 40:1 (v/w) ratio to form a slurry by stirring at 65° C. for approximately 45 minutes. Approximately 2.63 equivalents of HCl was added to the slurry at a rate of 2 volumes/hour. Slurry was stirred at 65° C. for approximately 45 minutes. A hot polish filtration was conducted. The filtrate was heated to 60° C. 2% weight of BT-11 dihydrochloride Form 2 was added. The slurry was stirred at 60° C. for approximately 7 hours. The slurry was cooled to 5° C. at 0.1° C./min and held at 5° C. for 9 hours. The slurry was cooled to 0° C. at a rate of 0.1° C./min and stirred at 0° C. for 16 hours. Solid material was filtered and washed with 1 volume of methanol. Wet solid was dried under vacuum at 40° C. for approximately 96 hours. Isolated material was analyzed by XRPD to have a unique crystalline form, designated to be Form 2.

Method XX. DMSO:methanol:water (50:40:10) was added to BT-11 free base in a 33:1 (v/w) ratio to form a slurry by stirring at 65° C. for approximately 45 minutes. Approximately 2.1 equivalents of HCl was added to the slurry at a rate of 2 volumes/hour. Slurry was stirred at 65° C. for approximately 30 minutes. A hot polish filtration was conducted. The filtrate was heated to 60° C. 1% weight of BT-11 dihydrochloride Form 2 was added. The slurry was stirred at 60° C. for approximately 8 hours. The slurry was cooled to 0° C. at a rate of 0.1° C./min and stirred at 0° C. for 25 hours. Solid material was filtered and washed with 1 volume of methanol. Wet solid was dried under vacuum at 40° C. for approximately 90 hours. Isolated material was analyzed by XRPD to have a unique crystalline form, designated to be Form 2.

Method XXI. DMSO:methanol:water (50:40:10) was added to BT-11 free base in a 33:1 (v/w) ratio to form a slurry by stirring at 65° C. for approximately 1 hour.

Approximately 2.6 equivalents of HCl was added to the slurry at a rate of 2 volumes/hour. The slurry was cooled to 60° C. 1% weight of BT-11 dihydrochloride Form 2 was added. The slurry was stirred at 60° C. for approximately 8 hours. The slurry was cooled to 0° C. at a rate of 0.1° C./min and stirred at 0° C. for 4 hours. Solid material was filtered and washed with 1 volume of methanol. Wet solid was dried under vacuum at 40° C. for approximately 68 hours. Isolated material was analyzed by XRPD to have a unique crystalline form, designated to be Form 2.

Method XXI. DMSO:methanol:water (50:40:10) was added to BT-11 free base in a 33:1 (v/w) ratio to form a slurry by stirring at 65° C. for approximately 1 hour. under vacuum at 25 to 55° C. Isolated material was analyzed by XRPD to have a unique crystalline form, designated to be Form 2.

Characterization

BT-11 Form 2 was characterized via XRPD (FIGS. 11, 12, 13, and 14). Methods I, II, and III are captured in FIG. 11. Methods IV and V are captured by FIG. 12. Method VIII is captured in FIG. 13. Methods XV, XVI, XVII, XVIII, XIX, XX, XXI and XXII are captured in FIGS. 14A-14B. No major differences in pattern were identified for methods VI, VII, IX, X, XI, XII, XIII or XIV. Representative diffraction peaks are presented in Table 5. Representative reduced cell parameters are presented in Table 6.

TABLE 5

Diffraction peaks observed for Form 2 of BT-11 dihydrochloride.

| No. | Pos. [°2θ] | d-spacing [Å] | Height [cts] | Area [cts * °2θ] | Rel. Int [%] | h | k | l | Position Calc. [°2θ] |
|---|---|---|---|---|---|---|---|---|---|
| 1 | 7.1488 | 12.36575 | 623.69 | 47.22 | 24.84 | 1 | 0 | 0 | 7.1443 |
| 2 | 10.0477 | 8.80367 | 774.17 | 68.38 | 30.83 | 1 | 1 | 0 | 10.0306 |
| 3 | 11.9621 | 7.39867 | 489.53 | 37.06 | 19.49 | 0 | 1 | −1 | 11.9588 |
| 4 | 12.564 | 7.04553 | 952.4 | 84.13 | 37.93 | 1 | 1 | −1 | 12.5639 |
| 5 | 14.322 | 6.18441 | 723.14 | 54.75 | 28.8 | 2 | 0 | 0 | 14.3165 |
| 6 | 15.2001 | 5.82907 | 332.76 | 25.19 | 13.25 | 1 | 1 | 1 | 15.201 |
| 7 | 16.607 | 5.33829 | 673.37 | 50.98 | 26.81 | 2 | 1 | −1 | 16.6079 |
| 8 | 17.1144 | 5.18115 | 966.5 | 97.57 | 38.49 | 0 | 2 | −1 | 17.1117 |
| 9 | 19.3787 | 4.58057 | 689.28 | 60.88 | 27.45 | 0 | 0 | 2 | 19.3915 |
| 10 | 20.6609 | 4.2991 | 1607.15 | 162.24 | 64 | 2 | 2 | −1 | 20.6553 |
| 11 | 21.5528 | 4.12316 | 278.52 | 21.09 | 11.09 | 3 | 0 | 0 | 21.5457 |
| 12 | 22.3362 | 3.977 | 1114.59 | 139.1 | 44.38 | 3 | 1 | −1 | 22.3339 |
| 13 | 23.3545 | 3.80586 | 2511.24 | 417.87 | 100 | 0 | 3 | 1 | 23.3463 |
| 14 | 23.9761 | 3.70857 | 466.24 | 48.49 | 18.57 | 2 | 2 | 1 | 23.9873 |
| 15 | 25.5263 | 3.48675 | 656.09 | 122.82 | 26.13 | 3 | 2 | −1 | 25.5218 |
| 16 | 28.4062 | 3.13947 | 2488.5 | 414.09 | 99.09 | 0 | 4 | 0 | 28.3986 |
| 17 | 28.863 | 3.09081 | 332.59 | 96.85 | 13.24 | 4 | 0 | 0 | 28.8628 |
| 18 | 29.3245 | 3.04321 | 568.51 | 70.95 | 22.64 | 1 | 4 | 0 | 29.3203 |
| 19 | 29.8776 | 2.98812 | 391.79 | 48.89 | 15.6 | 2 | 1 | −3 | 29.8983 |
| 20 | 34.6459 | 2.58701 | 450.07 | 56.17 | 17.92 | 2 | 3 | 2 | 34.6701 |

Approximately 2.2 equivalents of HCl was added to the slurry at a rate of 2 volumes/hour. The slurry was cooled to 60° C. 1% weight of BT-11 dihydrochloride Form 2 was added. The slurry was stirred at 60° C. for approximately 8 hours. The slurry was cooled to 0° C. at a rate of 0.1° C./min and stirred at 0° C. for 24 hours. Solid material was filtered and washed with 1 volume of methanol. Wet solid was dried under vacuum at 40° C. for approximately 68 hours. Isolated material was analyzed by XRPD to have a unique crystalline form, designated to be Form 2.

Method XXIII. BT-11 free base was added to DMSO:methanol:water (50:40:10) in a 1:33 (w/v) ratio to form a slurry by stirring at 25-35° C. for approximately 10 minutes. The temperature of the reaction mass was raised to 60-65° C. Approximately 2 to 3 equivalents of HCl, prepared in DMSO:methanol:water (50:40:10), were added over 1.5 to 2.5 hours. The reaction mass was filtered at 60-65° C. Approximately 1 to 2 percent weight of BT-11 dihydrochloride Form 2 was added. The slurry was stirred at 60-65° C. for approximately 6 to 8 hours. The slurry was cooled to 20-30° C. at a rate of approximately 8° C./hour and stirred at 20 to 30° C. for 1 to 2 hours. The slurry was cooled to 0 to 5° C. at a rate of approximately 6° C./hour and stirred at 0 to 5° C. for 12 to 14 hours. Solid material was filtered. Wet material was slurried in methanol:water for 5 to 96 hours at 25 to 55° C. Wet solid was filtered and dried

TABLE 6

Reduced Cell Parameters of Form 2 of BT-11 dihydrochloride.

| Cell Parameters | Value |
|---|---|
| a sigma [Å] | 12.81 |
| b sigma [Å] | 12.56 |
| c sigma [Å] | 9.48 |
| alpha (sigma) [°] | 90 |
| beta (sigma) [°] | 105.25 |
| gamma (sigma) [°] | 90 |

Figure 15:
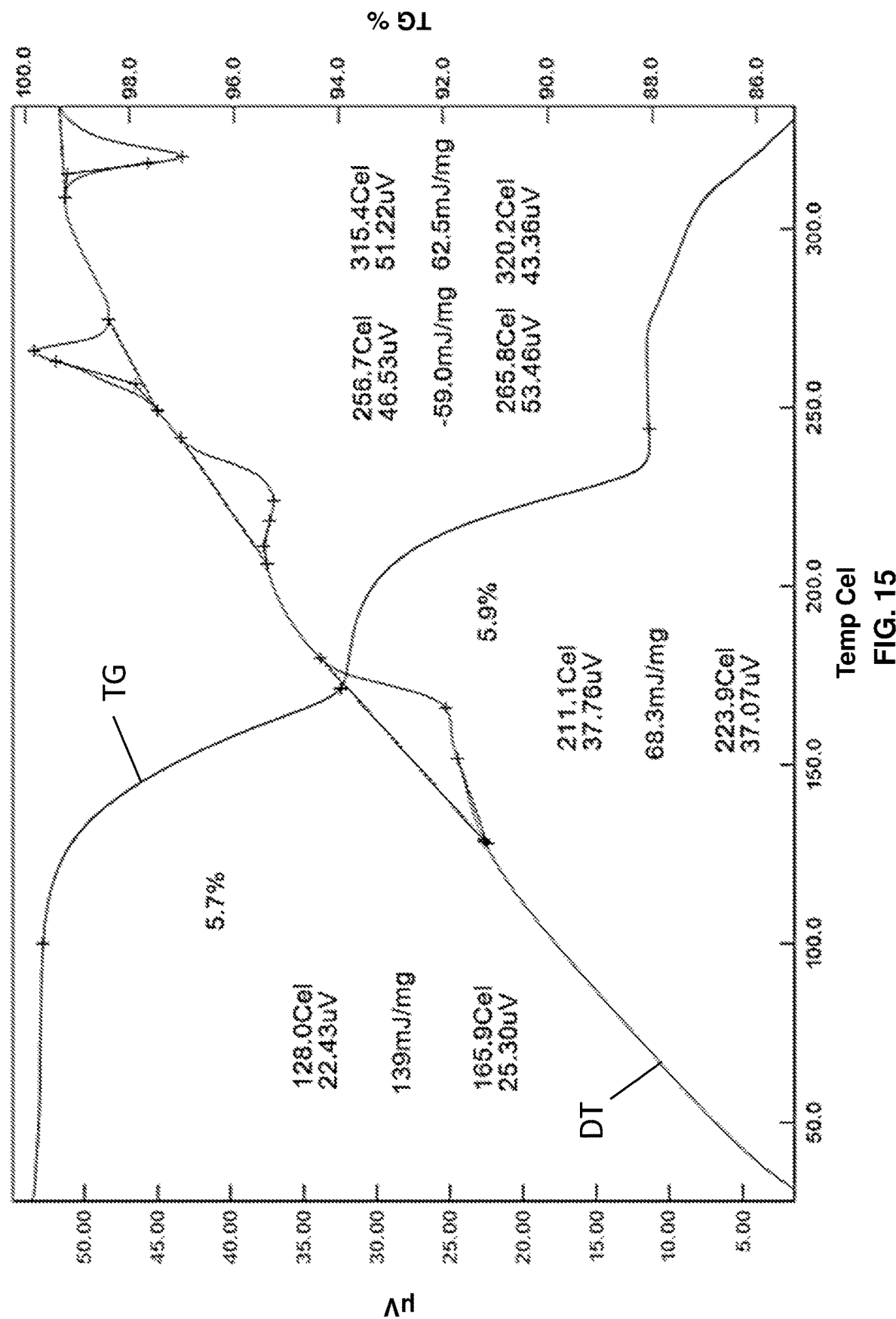
FIG. 15. TG/DTA thermogram of BT-11 dihydrochloride Form 2. The thermal gravimetric trace (TG) trace and differential thermal (DT) trace are indicated.
Figure 16:
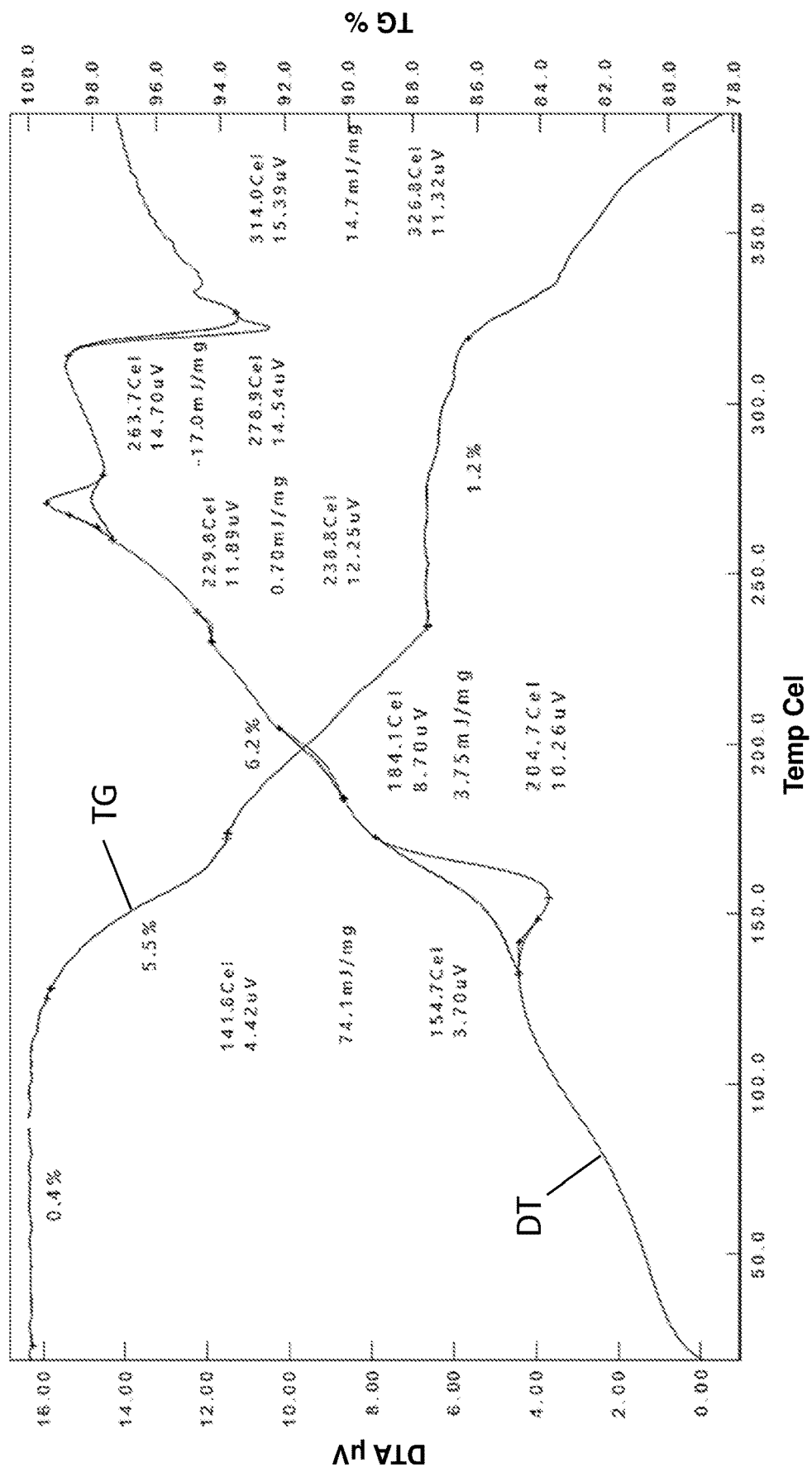
FIG. 16. TG/DTA thermogram for BT-11 dihydrochloride Form 2 produced from Methods XV and XIX.
Figure 17:
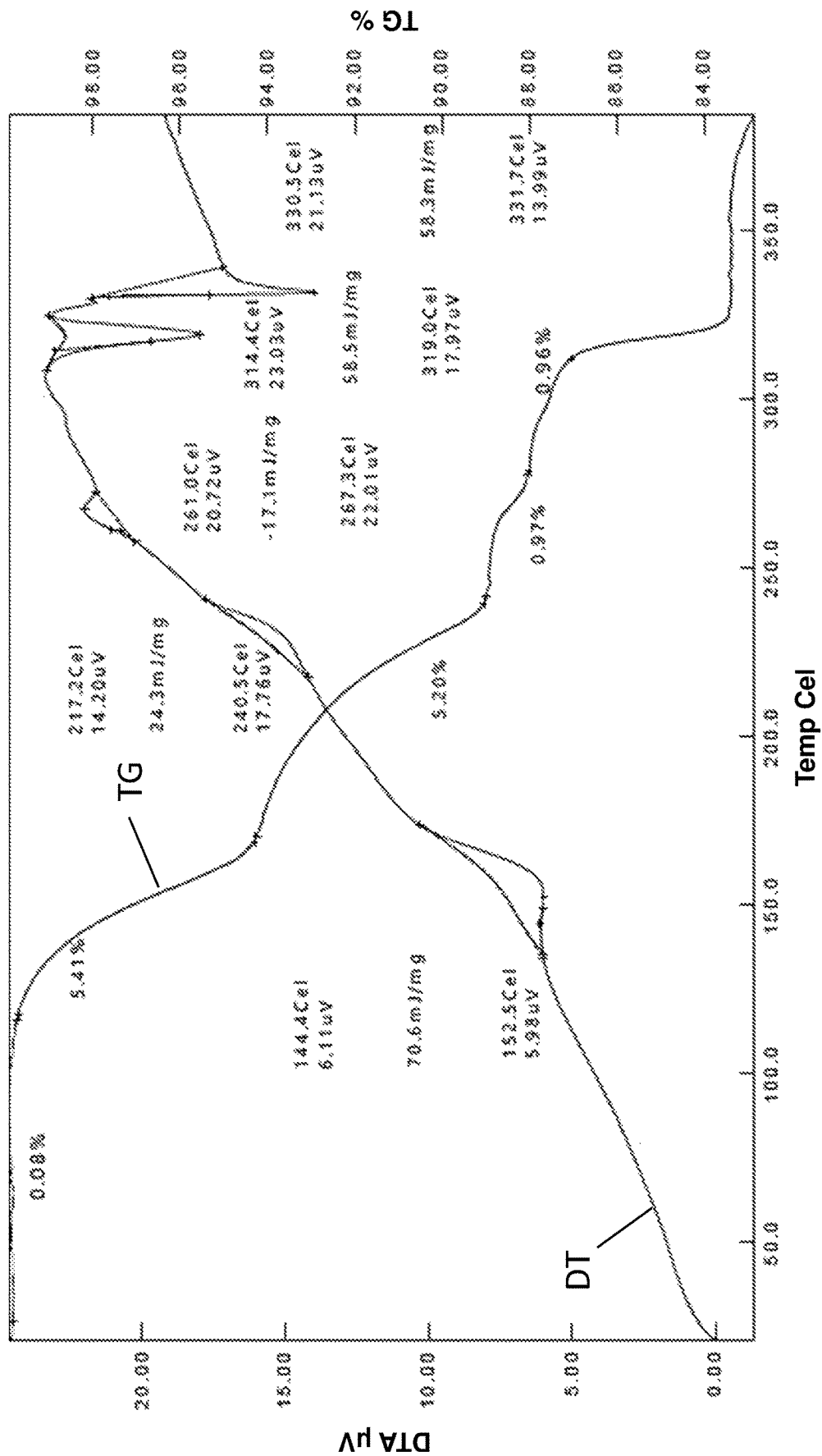
FIG. 17. TG/DTA thermogram for BT-11 dihydrochloride Form 2 produced from Methods XVI, XVII, XVIII, XX, XXI, and XXII.

BT-11 Form 2 was characterized via thermal gravimetric trace (FIG. 15). The thermal gravimetric trace (TG) showed no loss in mass below 100° C. Consecutive mass losses of 5.7 and 5.9% were observed. Two broad endothermic events associated with these losses were noted with onsets of ~128 and 211° C., respectively. An exothermic event was observed post-salt disproportionation with onset ~257° C. Post-recrystallization, an endothermic event with onset ~315° C. was noted. A representative TG/DTA for Methods XV and XIX is depicted in FIG. 16 and a representative TG/DTA for Methods XVI, XVII, XVIII, XX, XXI and XXII is depicted in FIG. 17. In FIG. 17, the material showed consecutive mass losses from the outset to ca. 35° C. An initial mass loss of 0.1% was observed, with further mass losses of 5.4% and 5.2% between 140-250° C. The larger mass losses were associated with broad endothermic events, with degradation of the material observed above 250° C.

BT-11 Form 2 was characterized via PLM. The PLM images showed some block-like particles with aggregation visible. The material appeared birefringent under polarized light, indicative of a crystalline material. PLM analysis of the dried material showed birefringent material with a mixture of small and large, plate-like morphology, with some aggregation observed.

Figure 18:
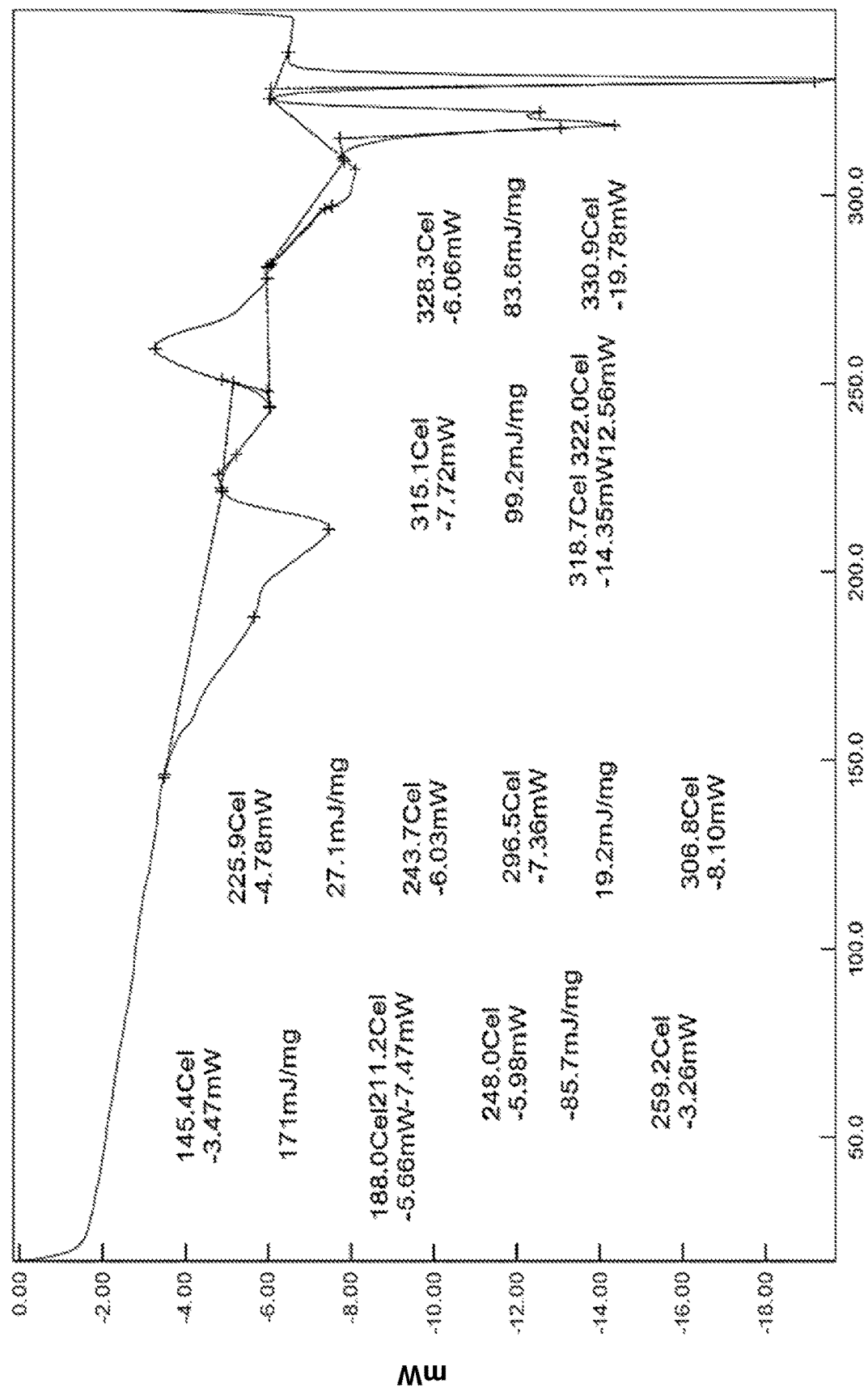
FIG. 18. DSC thermogram of BT-11 dihydrochloride Form 2.

BT-11 Form 2 was characterized via DSC (FIG. 18). The DSC thermogram showed a broad endothermic event (onset at 145° C.) observed which was immediately followed by a second broad endothermic event (onset at 226° C.). An exothermic event post-disproportionation was observed (onset at 248° C.). There were 2 sharp endothermic events were observed (onsets at 315 and 328° C., respectively).

Figure 19A:
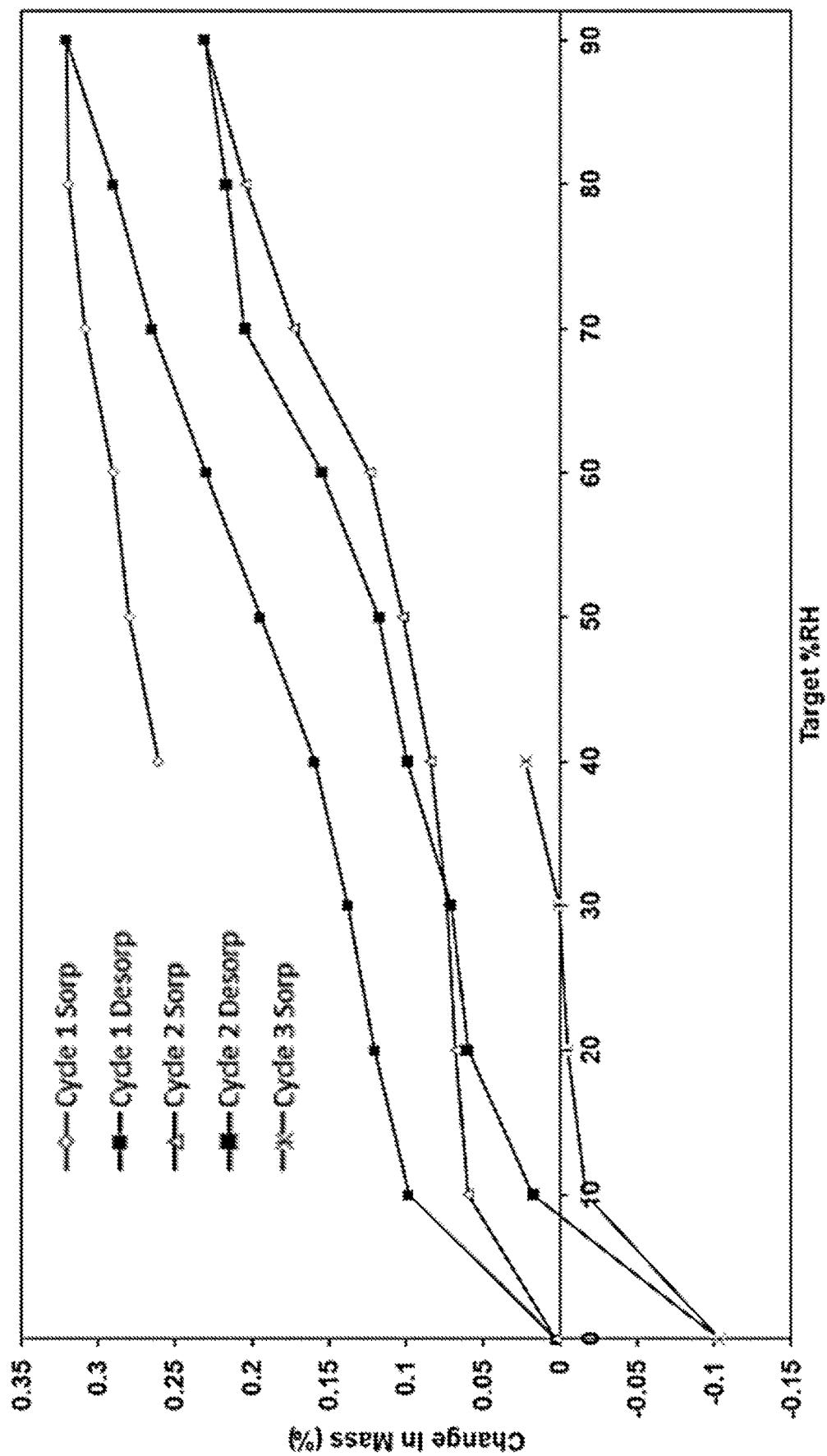
FIG. 19A and FIG. 19B. DVS isotherm (double cycle) (FIG. 19A) and DVS kinetic plot (FIG. 19B) for the analysis of BT-11 dihydrochloride Form 2.
Figure 19B:
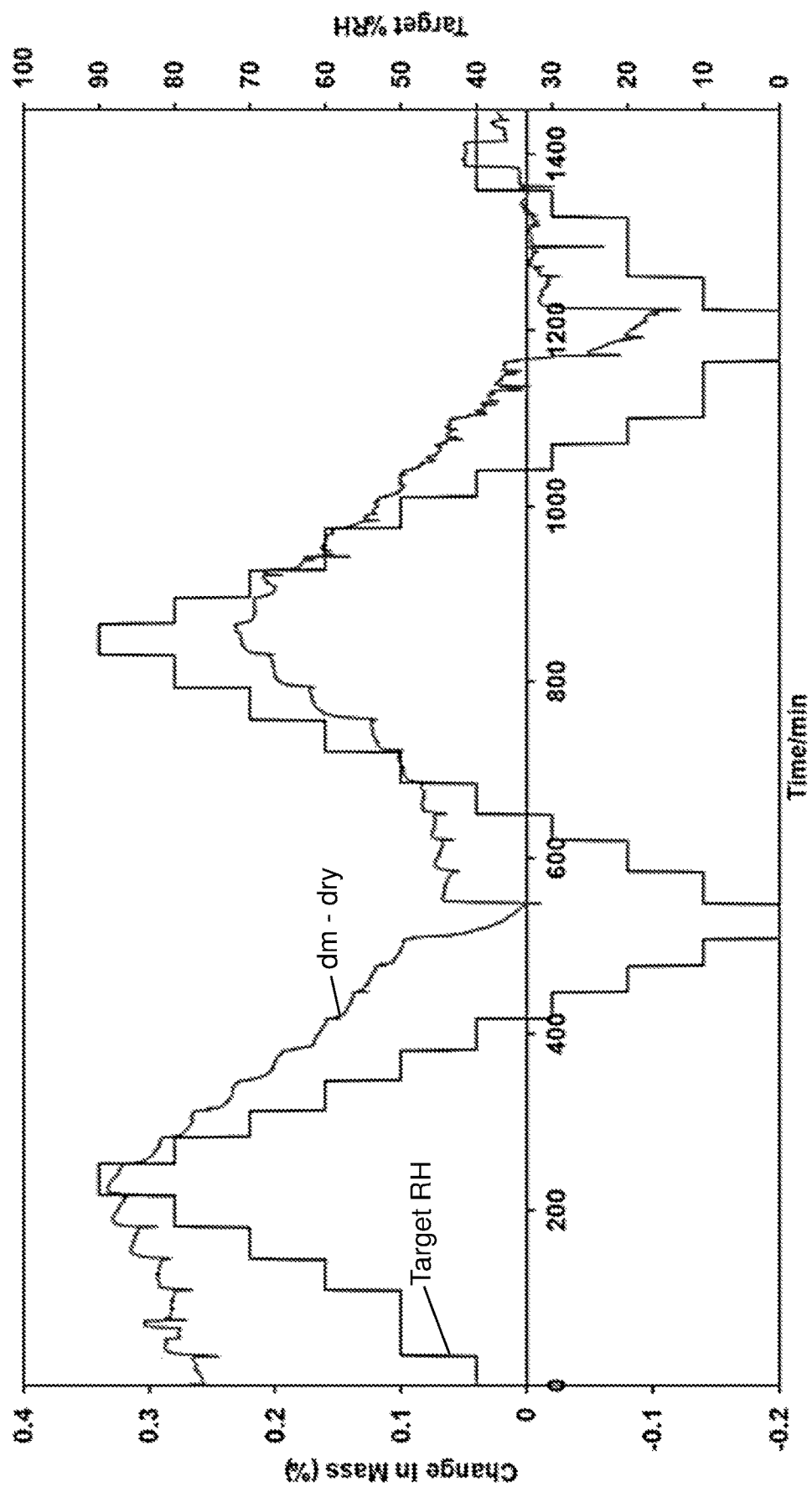

BT-11 Form 2 was characterized via DVS (FIGS. 19A-19B). DVS analysis showed a total 0.32% mass increase up to 90% RH. There was a 0.23% mass uptake on 2nd cycle and the material was slightly hygroscopic (FIG. 19A). Analysis of the DVS kinetic plot showed no evidence of re-crystallization or form change occurring during the DVS experiment (FIG. 19B).

BT-11 Form 2 was characterized by PSD. PSD analysis (FIG. 20) of the dried material showed that the material had a $d_{90}$ of 83.9 μm, $d_{50}$ of 31.9 μm and $d_{10}$ of 18.2 μm.

Example 4. Crystal Form 3 of BT-11

Form 3 Preparation Methods

Methanol, 1,4-dioxane, 1-butanol, 1-propanol, 2-methyl tetrahydrofuran, butyl acetate, dichloromethane, ethyl acetate, isopropyl alcohol, methyl ethyl ketone, tert-butyl methyl ether, or tetrahydrofuran were independently added to BT-11 dihydrochloride in a 100:1 (v/w) ratio to form slurries. Slurries were thermally cycled with agitation for 72 hours between ambient temperature for 4 hours followed by 40° C. for 4 hours. Solid material was isolated by filtration and dried at 40° C. for 2 hours. Dried material was analyzed by XRPD to have a unique crystalline form, designated to be Form 3.

Alternatively, lyophilized BT-11 dihydrochloride was added to ethyl acetate in a 1:50 (w/v) ratio to form a slurry. Slurry was thermally cycled with agitation for 24 hours between ambient temperature for 4 hours followed by 40° C. for 4 hours. Solid material was isolated by filtration and dried at ambient temperature under vacuum for 3 hours.

Characterization

BT-11 Form 3 was characterized via XRPD (FIGS. 21A, 21, 21C, and 21D). Crystallinity varied slightly between samples. Amorphous forms were observed from 1,4-dioxane, 1-butanol, 1-propanol, isopropyl alcohol, tert-butyl methyl ether and tetrahydrofuran solvents prior to drying. Minor additional peaks were noted in patterns produced from methanol, ethyl acetate, isopropyl acetate and MEK. Replacement of the listed solvents with acetone or chloroform resulted in mixtures of Forms 2 and 3 and Forms 1 and 3, respectively. Diffraction peaks for Form 3 are presented in Table 7. Reduced cell parameters for Form 3 are presented in Table 8.

TABLE 7

Diffraction peaks observed for Form 3 of BT-11 dihydrochloride.

| No. | Pos. [°2θ] | d-spacing [Å] | Height [cts] | Area [cts * °2θ] | Rel. Int [%] | h | k | l | Position Calc. [°2θ] |
| --- | --- | --- | --- | --- | --- | --- | --- | --- | --- |
| 1 | 8.1744 | 10.81637 | 465.03 | 93.89 | 46.13 | 0 | 1 | 1 | 8.1694 |
| 2 | 10.263 | 8.61943 | 1008.11 | 127.21 | 100 | 0 | 0 | 1 | 10.2418 |
| 3 | 11.4594 | 7.72206 | 351.81 | 39.95 | 34.9 | 0 | 1 | 0 | 11.4459 |
| 4 | 14.0108 | 6.32108 | 526.47 | 93.01 | 52.22 | 1 | 2 | 0 | 13.9276 |
| 5 | 14.5785 | 6.07617 | 186.6 | 37.67 | 18.51 | 0 | 1 | 2 | 14.5966 |
| 6 | 15.3272 | 5.78102 | 314.07 | 71.34 | 31.15 | 1 | 1 | -2 | 15.3002 |
| 7 | 17.1351 | 5.17494 | 746.56 | 113.05 | 74.06 | 0 | 2 | 1 | 17.0862 |
| 8 | 17.9941 | 4.92979 | 144.46 | 36.46 | 14.33 | 2 | 1 | -2 | 18.0093 |
| 9 | 20.5635 | 4.31924 | 298.21 | 60.21 | 29.58 | 0 | 0 | 2 | 20.5666 |
| 10 | 21.387 | 4.15475 | 149.78 | 45.36 | 14.86 | 0 | 2 | 3 | 21.3951 |
| 11 | 22.4595 | 3.95873 | 333.25 | 67.28 | 33.06 | 1 | 3 | 0 | 22.4057 |
| 12 | 23.036 | 3.86094 | 444.07 | 56.04 | 44.05 | 0 | 2 | 0 | 23.008 |
| 13 | 23.9527 | 3.71522 | 569.78 | 86.28 | 56.52 | 2 | 1 | -4 | 23.9508 |
| 14 | 24.4536 | 3.64025 | 773.76 | 273.39 | 76.75 | 1 | 1 | -3 | 24.4152 |
| 15 | 25.0495 | 3.55498 | 603.51 | 152.31 | 59.87 | 2 | -1 | -4 | 25.0544 |
| 16 | 27.9172 | 3.19598 | 845 | 191.93 | 83.82 | 1 | 3 | -1 | 28.0041 |
| 17 | 29.0479 | 3.0741 | 687.16 | 138.74 | 68.16 | 0 | 3 | 4 | 29.0549 |
| 18 | 30.4717 | 2.9312 | 354.82 | 42.58 | 35.2 | 1 | 1 | 2 | 30.4797 |
| 19 | 31.4541 | 2.84421 | 405.58 | 163.77 | 40.23 | 0 | 2 | -1 | 31.4419 |
| 20 | 34.1203 | 2.62782 | 476.15 | 72.1 | 47.23 | 0 | 1 | 4 | 34.1199 |

TABLE 8

Reduced Cell Parameters of Form 3 of BT-11 dihydrochloride.

| Cell Parameters | Value |
| --- | --- |
| a sigma [Å] | 9.30 |
| b sigma [Å] | 11.78 |
| c sigma [Å] | 10.20 |
| alpha (sigma) [°] | 71.15 |
| beta (sigma) [°] | 106.99 |
| gamma (sigma) [°] | 108.35 |

Figure 22:
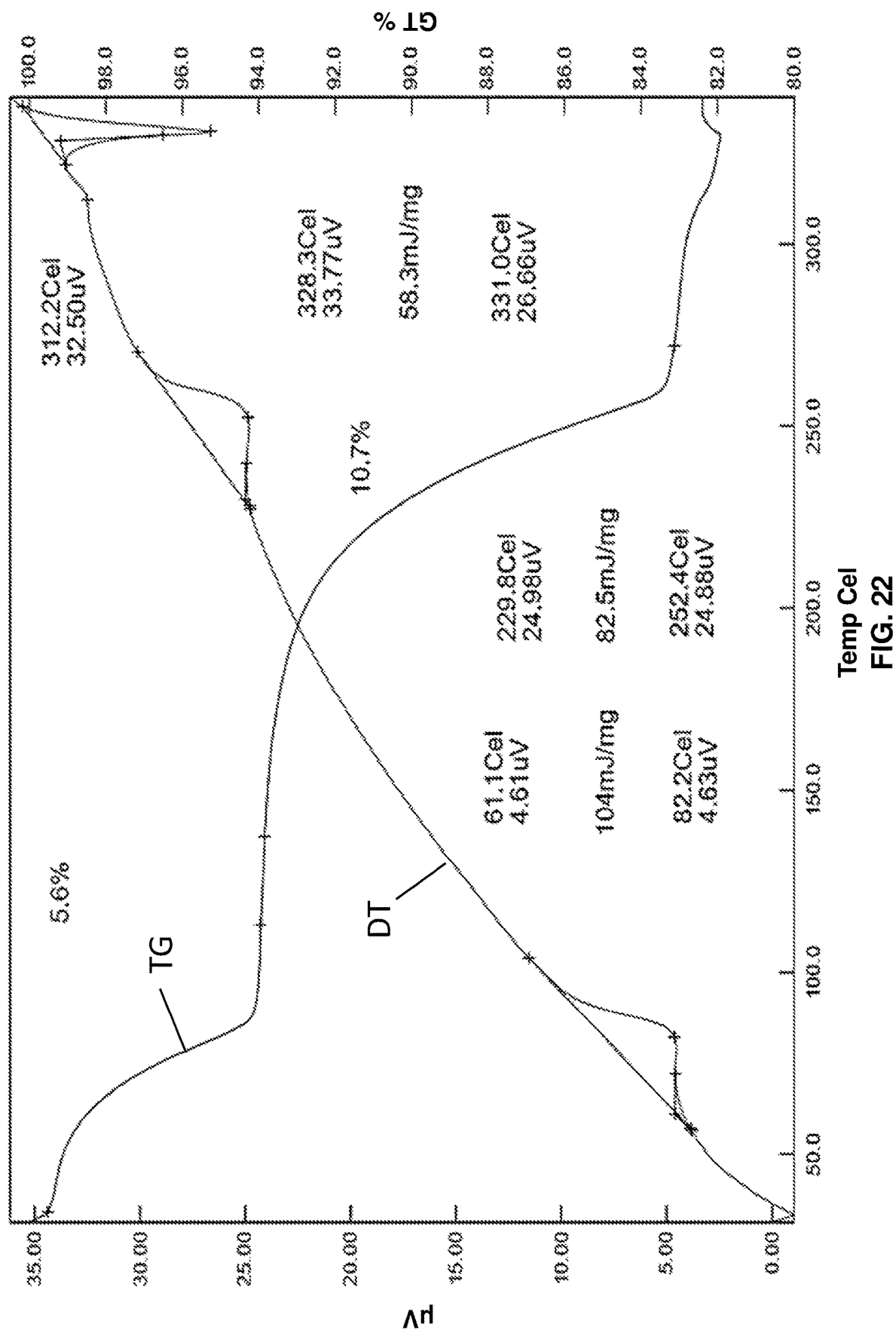
FIG. 22. TG/DTA thermogram of BT-11 dihydrochloride Form 3. The thermal gravimetric trace (TG) trace and differential thermal (DT) trace are indicated.

BT-11 Form 3 was characterized via thermal gravimetric trace (FIG. 22). The thermal gravimetric trace (TG) showed a 5.6% loss in mass below 100° C. A broad endothermic event (onset ~61° C.) was associated with this step. A mass loss of ~10.7% was observed around 140° C. to just above 260° C. A broad endothermic event was observed (onset ~230° C.). A sharp endothermic event (onset ~312° C.) was observed.

In PLM, the PLM images showed that the material consisted of no clear morphology and aggregation was visible. The material appeared birefringent under polarized light, indicative of a crystalline material.

Figure 23:
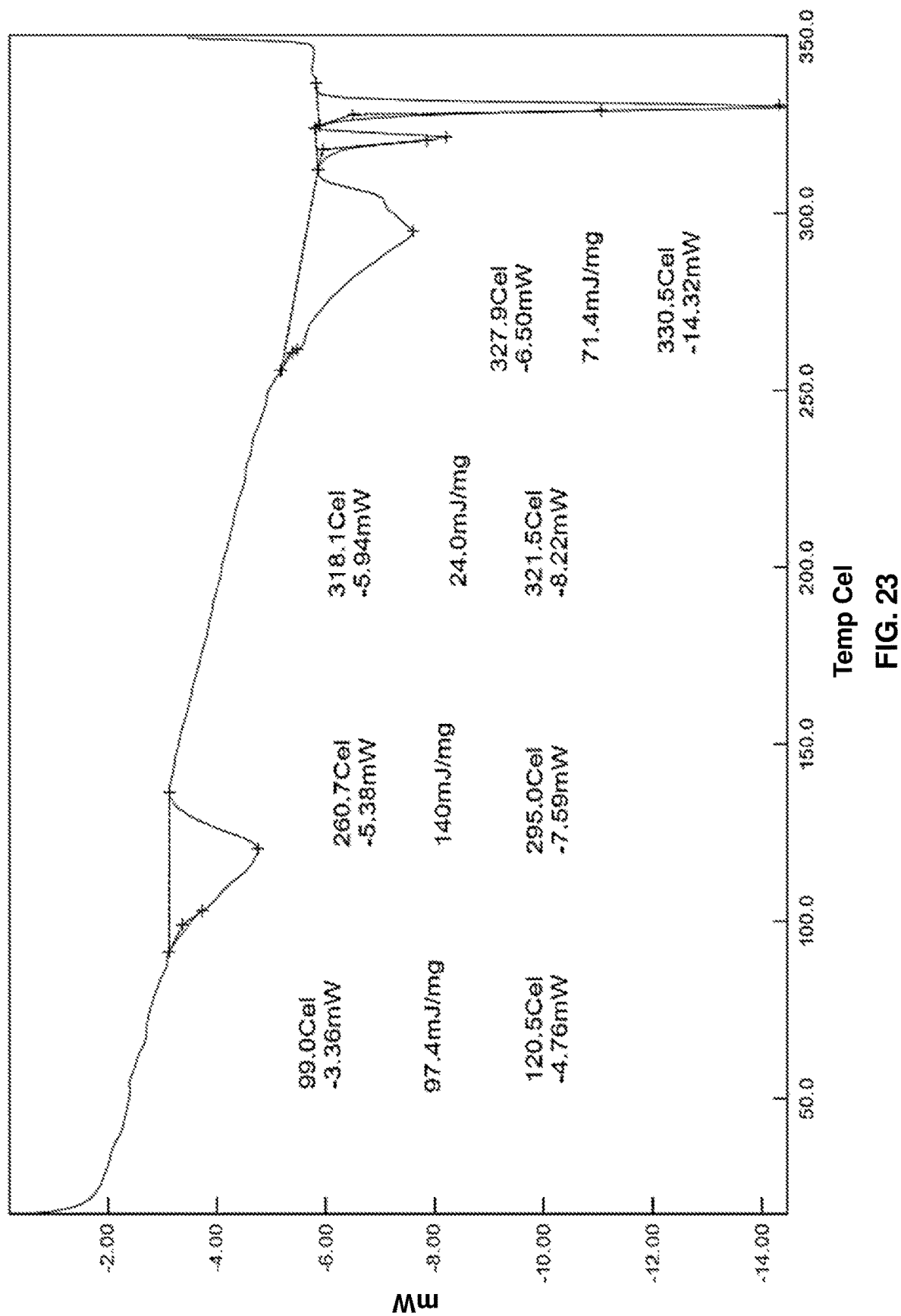
FIG. 23. DSC thermogram of BT-11 dihydrochloride Form 3.

BT-11 Form 3 was characterized via differential scanning calorimetry (FIG. 23). The DSC thermogram showed a broad endothermic event (onset at 99° C.). A second broad endothermic event was also noted (onset ~261° C.). Two sharp endothermic events were observed post-disproportionation (onsets at 318 and 328° C., respectively).

Figure 24A:
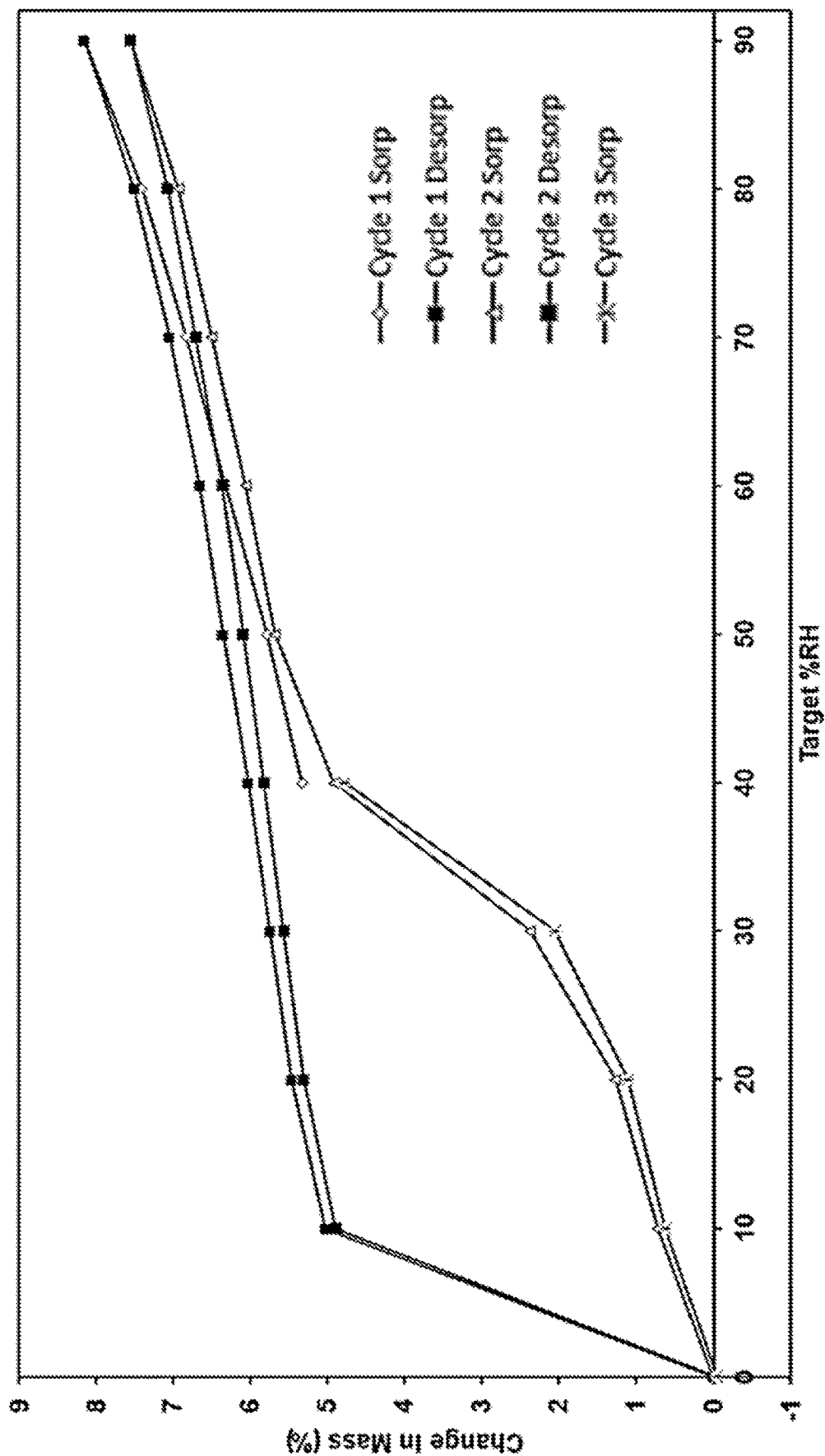
FIGS. 24A and 24B. DVS isotherm (double cycle) (FIG. 24A) and DVS kinetic plot (FIG. 24B) for the analysis of BT-11 dihydrochloride Form 3.
Figure 24B:
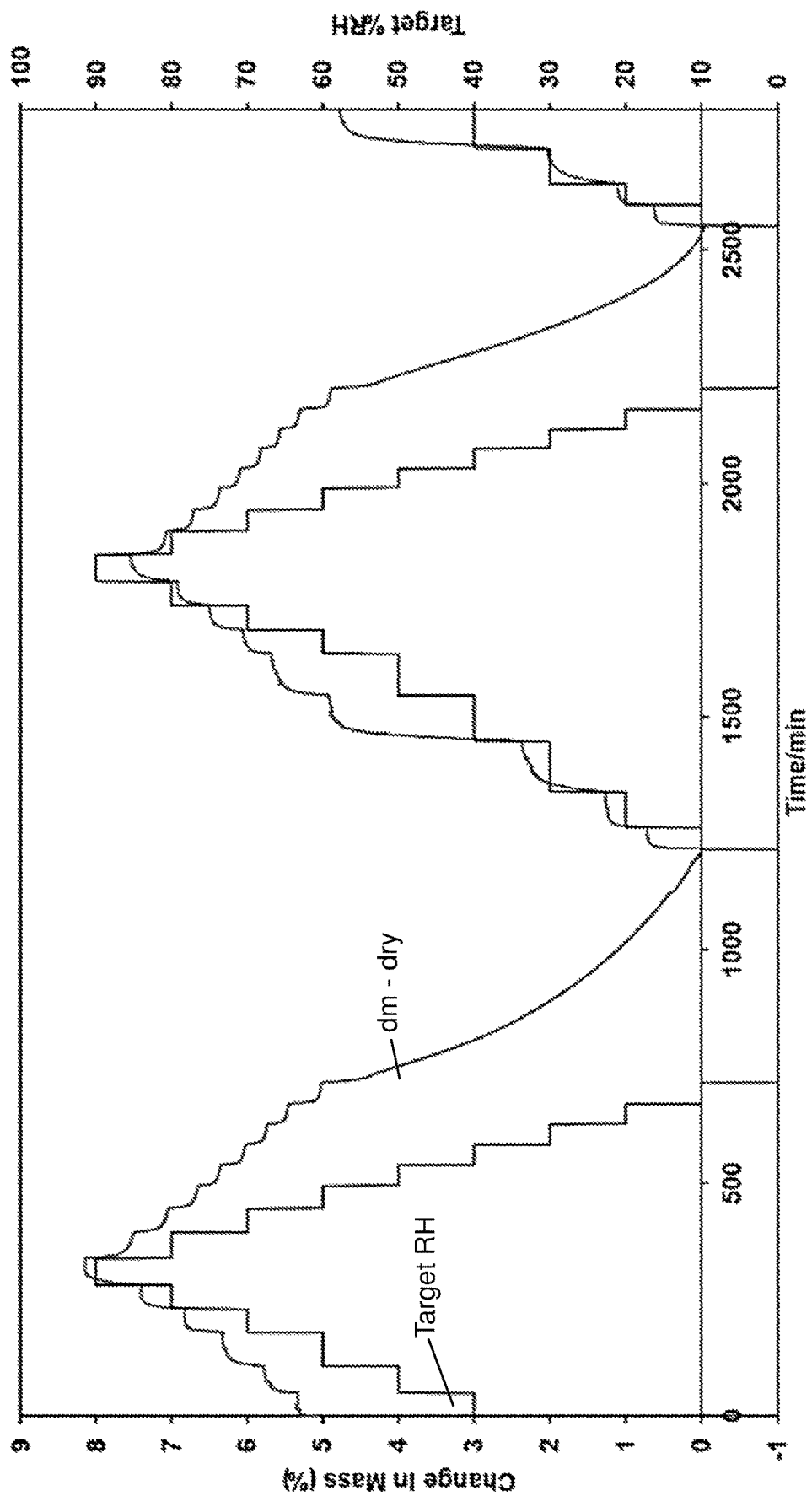

BT-11 Form 3 was characterized via dynamic vapor sorption. (FIGS. 24A-24B). DVS analysis showed a total 7.8% mass increase up to 90% RH (FIG. 24A). Only 2.8% of total moisture uptake was due to surface moisture. 5.0% of total mass was lost below 20% RH. Rehydration appeared slower than dehydration. No evidence of re-crystallization or form change occurring during the DVS experiment (FIG. 24B). Dehydration step was more pronounced that the rehydration step.

Example 5. Crystal Form 4 of BT-11

Form 4 Preparation Methods

Acetic acid was added to BT-11 dihydrochloride in a 100:1 (v/w) ratio to form a slurry. Slurry was thermally cycled with agitation for 72 hours between ambient temperature for 4 hours followed by 40° C. for 4 hours. Solid material was isolated by filtration and analyzed by XRPD to have a unique crystalline form, designated to be Form 4.

Characterization

BT-11 Form 4 was characterized via XRPD (FIG. 25). Diffraction peaks are presented in Table 9.

TABLE 9

Diffraction peaks observed for Form 4 of BT-11 dihydrochloride.

| No. | Pos. [°2θ] | d-spacing [Å] | Height [cts] | Area [cts * °2θ] | Rel. Int. [%] |
|---|---|---|---|---|---|
| 1 | 3.5565 | 24.84392 | 203.22 | 15.39 | 22.06 |
| 2 | 7.1292 | 12.39974 | 573.9 | 57.94 | 62.3 |
| 3 | 8.6264 | 10.25064 | 242.81 | 21.45 | 26.36 |
| 4 | 13.1455 | 6.73515 | 696.7 | 96.71 | 75.63 |
| 5 | 14.2953 | 6.1959 | 302.47 | 34.35 | 32.83 |
| 6 | 17.8608 | 4.96626 | 110.89 | 27.99 | 12.04 |
| 7 | 19.0407 | 4.66111 | 162.23 | 16.38 | 17.61 |
| 8 | 20.3714 | 4.35955 | 301.82 | 38.09 | 32.76 |
| 9 | 20.6541 | 4.30051 | 248.6 | 37.64 | 26.99 |
| 10 | 21.0797 | 4.21462 | 119.7 | 18.13 | 12.99 |
| 11 | 21.9166 | 4.05554 | 186.13 | 32.88 | 20.2 |
| 12 | 22.4612 | 3.95843 | 249.19 | 50.31 | 27.05 |
| 13 | 23.6032 | 3.76944 | 921.22 | 302.24 | 100 |
| 14 | 24.5428 | 3.62721 | 186.76 | 47.13 | 20.27 |
| 15 | 25.4064 | 3.50584 | 243.11 | 73.63 | 26.39 |
| 16 | 26.0308 | 3.42314 | 149.89 | 45.39 | 16.27 |
| 17 | 26.8957 | 3.31225 | 87.21 | 10.47 | 9.47 |
| 18 | 27.4974 | 3.24381 | 422.07 | 37.28 | 45.82 |
| 19 | 29.9564 | 2.9829 | 93.81 | 14.21 | 10.18 |
| 20 | 30.4171 | 2.93877 | 80.15 | 12.14 | 8.7 |

Example 6. Crystal Form 5 of BT-11

Form 5 Preparation Methods

Acetonitrile was added to BT-121 dihydrochloride in a 100:1 (v/w) ratio to form a slurry. Slurry was thermally cycled with agitation for 72 hours between ambient temperature for 4 hours followed by 40° C. for 4 hours. Solid material was isolated by filtration and analyzed by XRPD to have a unique crystalline form, designated to be Form 5.

Characterization

BT-11 Form was characterized via XRPD (FIG. 26). Diffraction peaks are presented in Table 10.

TABLE 10

Diffraction peaks observed for Form 5 of BT-11 dihydrochloride.

| No. | Pos. [°2θ] | d-spacing [Å] | Height [cts] | Area [cts * °2θ] | Rel. Int. [%] |
|---|---|---|---|---|---|
| 1 | 3.6941 | 23.91843 | 1530.44 | 96.56 | 64.49 |
| 2 | 7.0177 | 12.59648 | 460.23 | 58.07 | 19.39 |
| 3 | 7.3929 | 11.958 | 2373.27 | 179.69 | 100 |
| 4 | 11.0881 | 7.97978 | 447.47 | 28.23 | 18.85 |
| 5 | 13.4866 | 6.56555 | 699.4 | 70.6 | 29.47 |
| 6 | 13.9403 | 6.3529 | 536.93 | 60.98 | 22.62 |
| 7 | 14.8072 | 5.98285 | 1224.35 | 154.5 | 51.59 |
| 8 | 19.8257 | 4.47828 | 319.4 | 24.18 | 13.46 |
| 9 | 20.1935 | 4.39754 | 482.22 | 48.68 | 20.32 |
| 10 | 20.736 | 4.28371 | 464.46 | 58.61 | 19.57 |
| 11 | 21.3206 | 4.16756 | 574.55 | 87 | 24.21 |
| 12 | 21.8298 | 4.07147 | 528.2 | 33.33 | 22.26 |
| 13 | 22.5514 | 3.9428 | 582.66 | 102.93 | 24.55 |
| 14 | 22.8797 | 3.88696 | 681.69 | 103.22 | 28.72 |
| 15 | 23.5297 | 3.78104 | 720.97 | 163.76 | 30.38 |
| 16 | 24.7009 | 3.60435 | 967.04 | 195.24 | 40.75 |
| 17 | 25.3182 | 3.51786 | 256.23 | 25.87 | 10.8 |
| 18 | 27.1604 | 3.28329 | 731.5 | 92.31 | 30.82 |
| 19 | 27.422 | 3.25256 | 643.43 | 97.43 | 27.11 |
| 20 | 28.2596 | 3.15803 | 439.56 | 77.65 | 18.52 |

Figure 27:
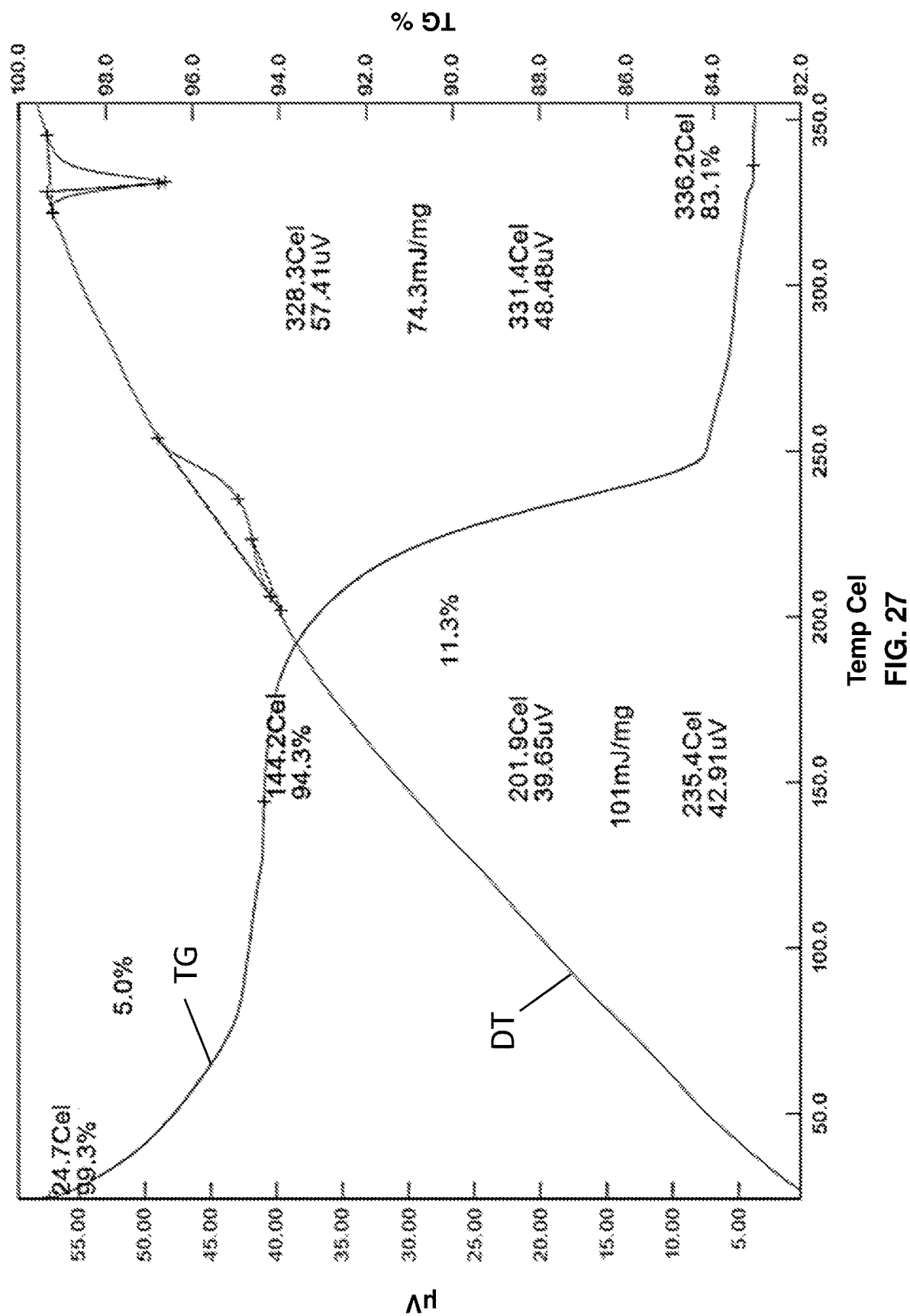
FIG. 27. TG/DTA thermogram of BT-11 dihydrochloride Form 5. The thermal gravimetric trace (TG) trace and differential thermal (DT) trace are indicated.

BT-11 Form 5 was characterized via thermal gravimetric trace (FIG. 27). The thermal gravimetric trace (TG) showed a 5.0% loss in mass below 150° C. A mass loss of ~11.3% was observed above 150° C. to just above 250° C. A broad endothermic event was observed (onset ~202° C.). A sharp endothermic event (onset ~328° C.) was observed.

Example 7. Crystal Form 6 of BT-11

Form 6 Preparation Methods

Water was added to BT-11 dihydrochloride in a 100:1 (v/w) ratio to form a slurry. Slurry was thermally cycled with agitation for 72 hours between ambient temperature for 4 hours followed by 40° C. for 4 hours. Solid material was isolated by filtration and analyzed by XRPD to have a unique crystalline form, designated to be Form 6.

Characterization

BT-11 Form 6 was characterized via XRPD (FIG. 28). Diffraction peaks are presented in Table 11. Reduced cell parameters are presented in Table 12.

TABLE 11

Diffraction peaks observed for Form 6 of BT-11.

| No. | Pos. [°2θ] | d-spacing [Å] | Height [cts] | Area [cts * °2θ] | Rel. Int [%] | h | k | l | Position Calc. [°2θ] |
|---|---|---|---|---|---|---|---|---|---|
| 1 | 3.2893 | 26.86163 | 129.02 | 104.2 | 6.92 | 0 | 0 | 1 | 3.8177 |
| 2 | 7.4943 | 11.79648 | 68.65 | 10.4 | 3.68 | 0 | 0 | 2 | 7.6396 |
| 3 | 9.4388 | 9.37014 | 772.3 | 48.73 | 41.42 | 0 | 1 | 1 | 9.4362 |
| 4 | 9.8112 | 9.01531 | 358.81 | 45.28 | 19.24 | 0 | 1 | 0 | 9.7881 |
| 5 | 13.9587 | 6.34457 | 356.46 | 35.98 | 19.12 | 1 | 0 | 1 | 13.7132 |
| 6 | 14.9672 | 5.91927 | 303.73 | 107.32 | 16.29 | 1 | 0 | 2 | 15.2391 |

TABLE 11-continued

Diffraction peaks observed for Form 6 of BT-11.

| No. | Pos. [°2θ] | d-spacing [Å] | Height [cts] | Area [cts * °2θ] | Rel. Int [%] | h | k | l | Position Calc. [°2θ] |
|---|---|---|---|---|---|---|---|---|---|
| 7 | 15.6759 | 5.65318 | 206.9 | 41.77 | 11.1 | 0 | 0 | 4 | 15.3135 |
| 8 | 16.3126 | 5.42946 | 145.55 | 17.47 | 7.81 | 0 | 1 | 2 | 16.3131 |
| 9 | 16.9298 | 5.23722 | 294.13 | 89.08 | 15.77 | 0 | 1 | −1 | 16.9293 |
| 10 | 17.5467 | 5.05026 | 71.65 | 8.6 | 3.84 | 1 | 0 | 3 | 17.4952 |
| 11 | 18.9455 | 4.68431 | 379.61 | 47.9 | 20.36 | 0 | 0 | 5 | 19.1743 |
| 12 | 19.6453 | 4.51899 | 128.28 | 32.37 | 6.88 | 0 | 2 | 0 | 19.6486 |
| 13 | 20.4165 | 4.35 | 96.87 | 12.22 | 5.19 | 1 | 0 | 4 | 20.2471 |
| 14 | 21.2313 | 4.18487 | 109.82 | 55.43 | 5.89 | 1 | 0 | 0 | 21.2313 |
| 15 | 24.3455 | 3.65616 | 68.78 | 34.71 | 3.69 | 1 | 1 | 2 | 24.1799 |
| 16 | 25.737 | 3.46155 | 155.46 | 47.08 | 8.34 | 1 | 1 | 3 | 25.6879 |
| 17 | 26.7952 | 3.3272 | 1864.76 | 705.92 | 100 | 2 | 0 | 1 | 26.7938 |
| 18 | 27.7537 | 3.21443 | 1319.22 | 332.94 | 70.74 | 1 | 1 | 4 | 27.6702 |
| 19 | 28.2776 | 3.15606 | 481.78 | 97.27 | 25.84 | 1 | 2 | 0 | 28.2776 |
| 20 | 29.1773 | 3.06076 | 126.16 | 31.84 | 6.77 | 2 | 0 | 3 | 28.9689 |

TABLE 12

Reduced Cell Parameters of Form 6 of BT-11 (suspected free base).

| Cell Parameters | Value |
|---|---|
| a sigma [Å] | 4.21 |
| b sigma [Å] | 10.65 |
| c sigma [Å] | 10.47 |
| alpha (sigma) [°] | 117.79 |
| beta (sigma) [°] | 89.76 |
| gamma (sigma) [°] | 84.35 |

Figure 29:
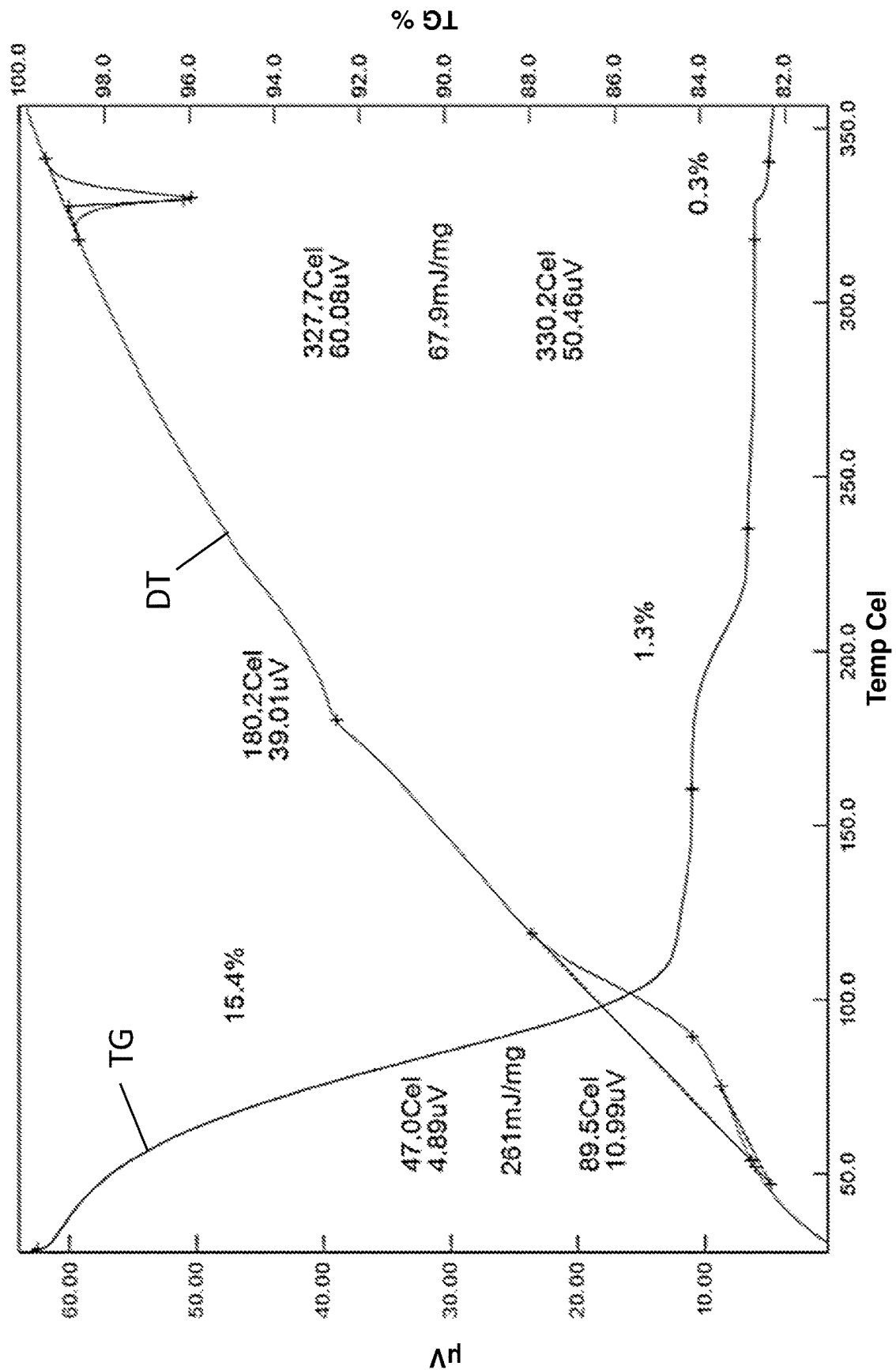
FIG. 29. TG/DTA thermogram of BT-11 dihydrochloride Form 6. The thermal gravimetric trace (TG) trace and differential thermal (DT) trace are indicated.

BT-11 Form 6 was characterized via thermal gravimetric trace (FIG. 29). The thermal gravimetric trace (TG) showed a 15.4% loss in mass below around 130° C. A mass loss of ~1.3% was observed above 150° C. to just below 250° C. with a weak exothermic event noted during the loss in mass (onset ~180° C.). A sharp endothermic event (onset ~328° C.) was observed.

Example 8. Crystal Form 7 of BT-11

Form 7 Preparation Methods

Methanol:water (80:20) was added to BT-11 dihydrochloride in a 40:1 (v/w) ratio to form a slurry. Slurry was thermally cycled with agitation for 72 hours between ambient temperature for 4 hours followed by 40° C. for 4 hours. Solid material was isolated by filtration and analyzed by XRPD to have a unique crystalline form, designated to be Form 7.

Characterization

BT-11 Form 7 was characterized via XRPD (FIG. 30). Post-drying, BT-11 Form 7 was observed to convert to Form 2. Diffraction peaks are presented in Table 13. Reduced cell parameters are presented in Table 14.

TABLE 13

Diffraction peaks observed for Form 7 of BT-11 dihydrochloride.

| No. | Pos. [°2θ] | d-spacing [Å] | Height [cts] | Area [cts * °2θ] | Rel. Int [%] | h | k | l | Position Calc. [°2θ] |
|---|---|---|---|---|---|---|---|---|---|
| 1 | 9.4586 | 9.35057 | 152.63 | 15.41 | 18.88 | 0 | 1 | 0 | 9.4629 |
| 2 | 10.0617 | 8.79144 | 557.22 | 28.13 | 68.94 | 1 | 0 | 0 | 10.0481 |
| 3 | 12.2614 | 7.2187 | 723.5 | 36.52 | 89.51 | 0 | 1 | 1 | 12.2943 |
| 4 | 13.6865 | 6.4701 | 168.28 | 16.99 | 20.82 | 0 | 1 | −1 | 13.6472 |
| 5 | 14.2039 | 6.23557 | 200.82 | 15.2 | 24.84 | 1 | 1 | 1 | 14.729 |
| 6 | 15.1273 | 5.85695 | 148.7 | 22.52 | 18.4 | 1 | 1 | 0 | 15.121 |
| 7 | 18.5131 | 4.79272 | 177.1 | 17.88 | 21.91 | 2 | 0 | 1 | 18.4052 |
| 8 | 20.2243 | 4.39092 | 172.42 | 15.23 | 21.33 | 2 | 0 | 0 | 20.1745 |
| 9 | 20.6669 | 4.29786 | 346.38 | 30.6 | 42.85 | 1 | −2 | 1 | 20.7074 |
| 10 | 22.5078 | 3.95033 | 224.87 | 28.38 | 27.82 | 1 | −2 | −1 | 22.5086 |
| 11 | 22.7248 | 3.91311 | 185.79 | 14.07 | 22.98 | 1 | 2 | 1 | 22.5882 |
| 12 | 24.5678 | 3.62358 | 191.1 | 24.11 | 23.64 | 1 | 0 | 3 | 24.4743 |
| 13 | 24.9061 | 3.57512 | 298.63 | 15.07 | 36.94 | 2 | −2 | 0 | 24.9162 |
| 14 | 25.9358 | 3.43547 | 392.06 | 34.63 | 48.5 | 1 | 1 | 3 | 25.9976 |
| 15 | 27.1472 | 3.28486 | 808.31 | 91.8 | 100 | 1 | 1 | −2 | 27.1268 |
| 16 | 27.5788 | 3.23442 | 208.04 | 21 | 25.74 | 0 | 1 | 3 | 27.5554 |
| 17 | 31.5353 | 2.83707 | 158.95 | 20.06 | 19.66 | 1 | 3 | 1 | 31.5456 |
| 18 | 31.5353 | 2.83707 | 158.95 | 20.06 | 19.66 | 2 | −1 | 3 | 31.4949 |
| 19 | 32.6526 | 2.7425 | 138.8 | 14.01 | 17.17 | 3 | −2 | 0 | 32.6918 |
| 20 | 32.6526 | 2.7425 | 138.8 | 14.01 | 17.17 | 0 | 1 | −4 | 32.6523 |

TABLE 14

Reduced Cell Parameters of Form 7 of BT-11 dihydrochloride.

| Cell Parameters | Value |
|---|---|
| a sigma [Å] | 9.78 |
| b sigma [Å] | 9.53 |
| c sigma [Å] | 10.91 |
| alpha (sigma) [°] | 88.50 |
| beta (sigma) [°] | 66.51 |
| gamma (sigma) [°] | 99.77 |

Example 9. Crystal Form 8 of BT-11

Form 8 Preparation Methods 2-propanol was added to BT-11 dihydrochloride in a 100:1 (v/w) ratio to form a slurry. Slurry was thermally cycled with agitation for 72 hours between ambient temperature for 4 hours followed by 40° C. for 4 hours. Solid material was isolated by filtration and dried at 40° C. for 2 hours. Dried material was analyzed by XRPD to have a unique crystalline form, designated to be Form 8.

Characterization

BT-11 Form 8 was characterized via XRPD (FIG. 31). Diffraction peaks are presented in Table 15.

TABLE 15

Diffraction peaks observed for Form 8 of BT-11 dihydrochloride.

| No. | Pos. [°2θ] | d-spacing [Å] | Height [cts] | Area [cts * °2θ] | Rel. Int. [%] |
|---|---|---|---|---|---|
| 1 | 6.6209 | 13.35038 | 315.65 | 19.92 | 29.09 |
| 2 | 7.5707 | 11.6776 | 1085.17 | 82.16 | 100 |
| 3 | 11.3551 | 7.79276 | 227.61 | 8.62 | 20.97 |
| 4 | 13.2915 | 6.66149 | 614.77 | 38.79 | 56.65 |
| 5 | 13.5731 | 6.52393 | 586.72 | 44.42 | 54.07 |
| 6 | 15.1814 | 5.83621 | 540.27 | 61.36 | 49.79 |
| 7 | 19.5347 | 4.54434 | 450.02 | 34.07 | 41.47 |
| 8 | 22.2588 | 3.99396 | 847.58 | 149.73 | 78.11 |
| 9 | 22.933 | 3.87805 | 444.11 | 67.25 | 40.93 |
| 10 | 23.5098 | 3.7842 | 323.89 | 40.87 | 29.85 |
| 11 | 24.0544 | 3.69974 | 710.31 | 107.56 | 65.46 |
| 12 | 24.4886 | 3.63512 | 320.6 | 48.55 | 29.54 |
| 13 | 25.3358 | 3.51545 | 555.82 | 112.22 | 51.22 |
| 14 | 25.8734 | 3.44361 | 258.38 | 39.13 | 23.81 |
| 15 | 26.6435 | 3.3458 | 322.06 | 56.9 | 29.68 |
| 16 | 27.451 | 3.24919 | 424.16 | 85.64 | 39.09 |
| 17 | 27.9198 | 3.19569 | 524.57 | 66.19 | 48.34 |
| 18 | 29.1013 | 3.06858 | 300.27 | 53.05 | 27.67 |
| 19 | 30.3273 | 2.94727 | 275.82 | 48.73 | 25.42 |
| 20 | 32.3621 | 2.76645 | 226.25 | 34.26 | 20.85 |

Figure 32:
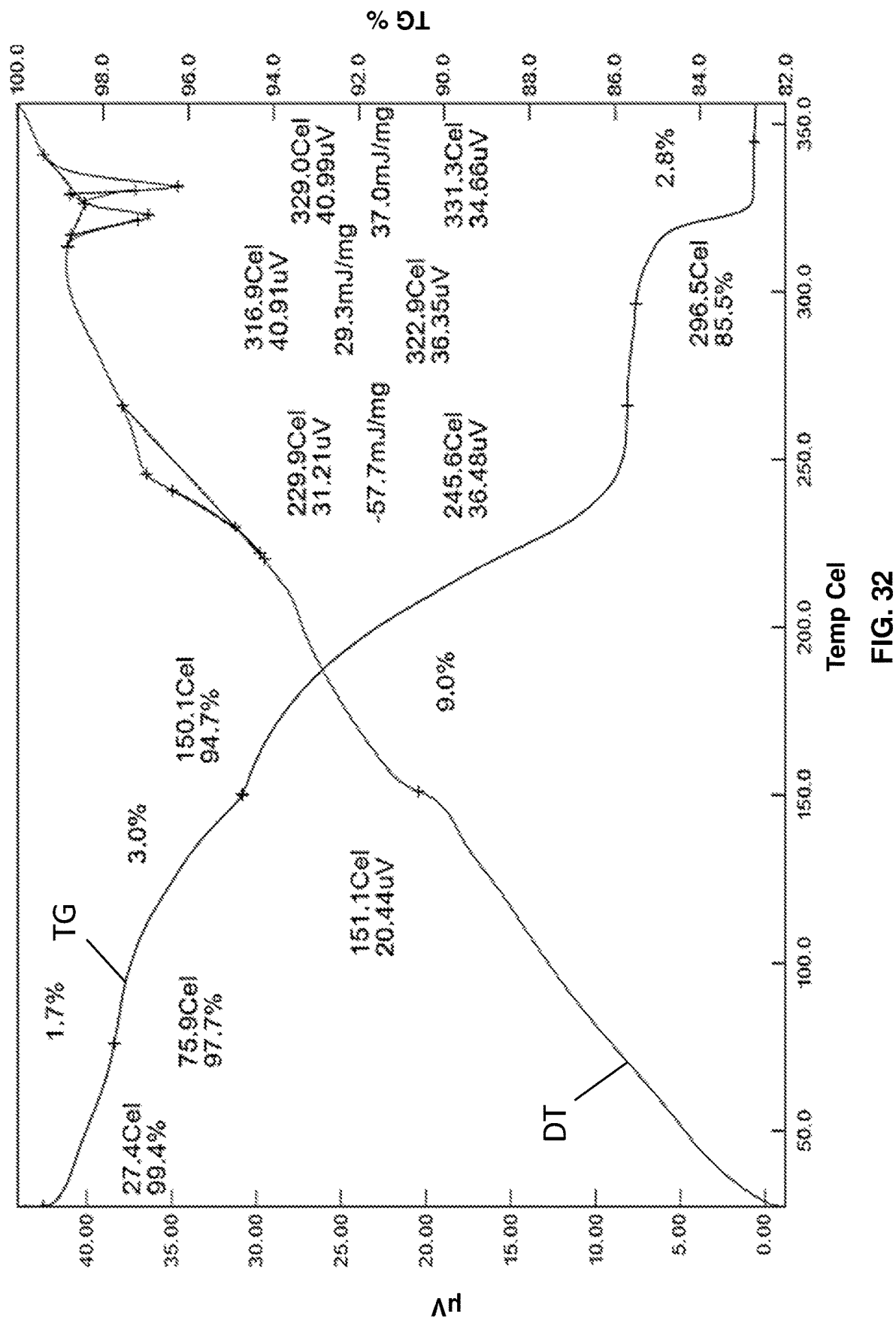
FIG. 32. TG/DTA thermogram of the BT-11 dihydrochloride Form 8. The thermal gravimetric trace (TG) trace and differential thermal (DT) trace are indicated.

BT-11 Form 8 was characterized via thermal gravimetric trace (FIG. 32). The thermal gravimetric trace showed consecutive losses in mass observed from the outset of heating up to ~250° C. The 1.7% and 3.0% mass losses were observed. A 9.0% mass loss was observed. The differential thermogram (TG) showed a broad exothermic event (onset 230° C.) followed by two endothermic events (onsets of 317 and 329° C.). No further loss in mass until the onset of the first endothermic event observed.

Example 10. Crystal Form 9 of BT-11

Form 9 Preparation Methods

Ethanol was added to BT-11 dihydrochloride in a 100:1 (v/w) ratio to form a slurry. Slurry was thermally cycled with agitation for 72 hours between ambient temperature for 4 hours followed by 40° C. for 4 hours. Solid material was isolated by filtration and dried at 40° C. for 2 hours. Dried material was analyzed by XRPD to have a unique crystalline form, designated to be Form 9.

Characterization

BT-11 Form 9 was characterized via XRPD (FIG. 33). Diffraction peaks are presented in Table 16. Reduced cell parameters are presented in Table 17.

TABLE 16

Diffraction peaks observed for Form 9 of BT-11 dihydrochloride.

| No. | Pos. [°2θ] | d-spacing [Å] | Height [cts] | Area [cts * °2θ] | Rel. Int [%] | h | k | l | Position Calc. [°2θ] |
|---|---|---|---|---|---|---|---|---|---|
| 1 | 9.4586 | 9.35057 | 152.63 | 15.41 | 18.88 | 0 | 1 | 0 | 9.4629 |
| 2 | 10.0617 | 8.79144 | 557.22 | 28.13 | 68.94 | 1 | 0 | 0 | 10.0481 |
| 3 | 12.2614 | 7.2187 | 723.5 | 36.52 | 89.51 | 0 | 1 | 1 | 12.2943 |
| 4 | 13.6865 | 6.4701 | 168.28 | 16.99 | 20.82 | 0 | 1 | −1 | 13.6472 |
| 5 | 14.2039 | 6.23557 | 200.82 | 15.2 | 24.84 | 1 | 1 | 1 | 14.729 |
| 6 | 15.1273 | 5.85695 | 148.7 | 22.52 | 18.4 | 1 | 1 | 0 | 15.121 |
| 7 | 18.5131 | 4.79272 | 177.1 | 17.88 | 21.91 | 2 | 0 | 1 | 18.4052 |
| 8 | 20.2243 | 4.39092 | 172.42 | 15.23 | 21.33 | 2 | 0 | 0 | 20.1745 |
| 9 | 20.6669 | 4.29786 | 346.38 | 30.6 | 42.85 | 1 | −2 | 1 | 20.7074 |
| 10 | 22.5078 | 3.95033 | 224.87 | 28.38 | 27.82 | 1 | −2 | −1 | 22.5086 |
| 11 | 22.7248 | 3.91311 | 185.79 | 14.07 | 22.98 | 1 | 2 | 1 | 22.5882 |
| 12 | 24.5678 | 3.62358 | 191.1 | 24.11 | 23.64 | 1 | 0 | 3 | 24.4743 |
| 13 | 24.9061 | 3.57512 | 298.63 | 15.07 | 36.94 | 2 | −2 | 0 | 24.9162 |
| 14 | 25.9358 | 3.43547 | 392.06 | 34.63 | 48.5 | 1 | 1 | 3 | 25.9976 |
| 15 | 26.0429 | 3.42159 | 1698.52 | 192.9 | 48.45 | 4 | −3 | −3 | 26.0557 |
| 16 | 27.1381 | 3.28594 | 1849.07 | 209.99 | 52.74 | 1 | −5 | −2 | 27.1918 |
| 17 | 27.1472 | 3.28486 | 808.31 | 91.8 | 100 | 1 | 1 | −2 | 27.1268 |
| 18 | 27.5788 | 3.23442 | 208.04 | 21 | 25.74 | 0 | 1 | 3 | 27.5554 |
| 19 | 27.64 | 3.2274 | 1658.27 | 188.33 | 47.3 | 5 | −2 | 0 | 27.6262 |
| 20 | 31.5353 | 2.83707 | 158.95 | 20.06 | 19.66 | 1 | 3 | 1 | 31.5456 |

TABLE 17

Reduced Cell Parameters of Form 9 of BT-11 dihydrochloride.

| Cell Parameters | Value |
| --- | --- |
| a sigma [Å] | 16.93 |
| b sigma [Å] | 17.31 |
| c sigma [Å] | 10.08 |
| alpha (sigma) [°] | 100.23 |
| beta (sigma) [°] | 100.89 |
| gamma (sigma) [°] | 71.77 |

Figure 34:
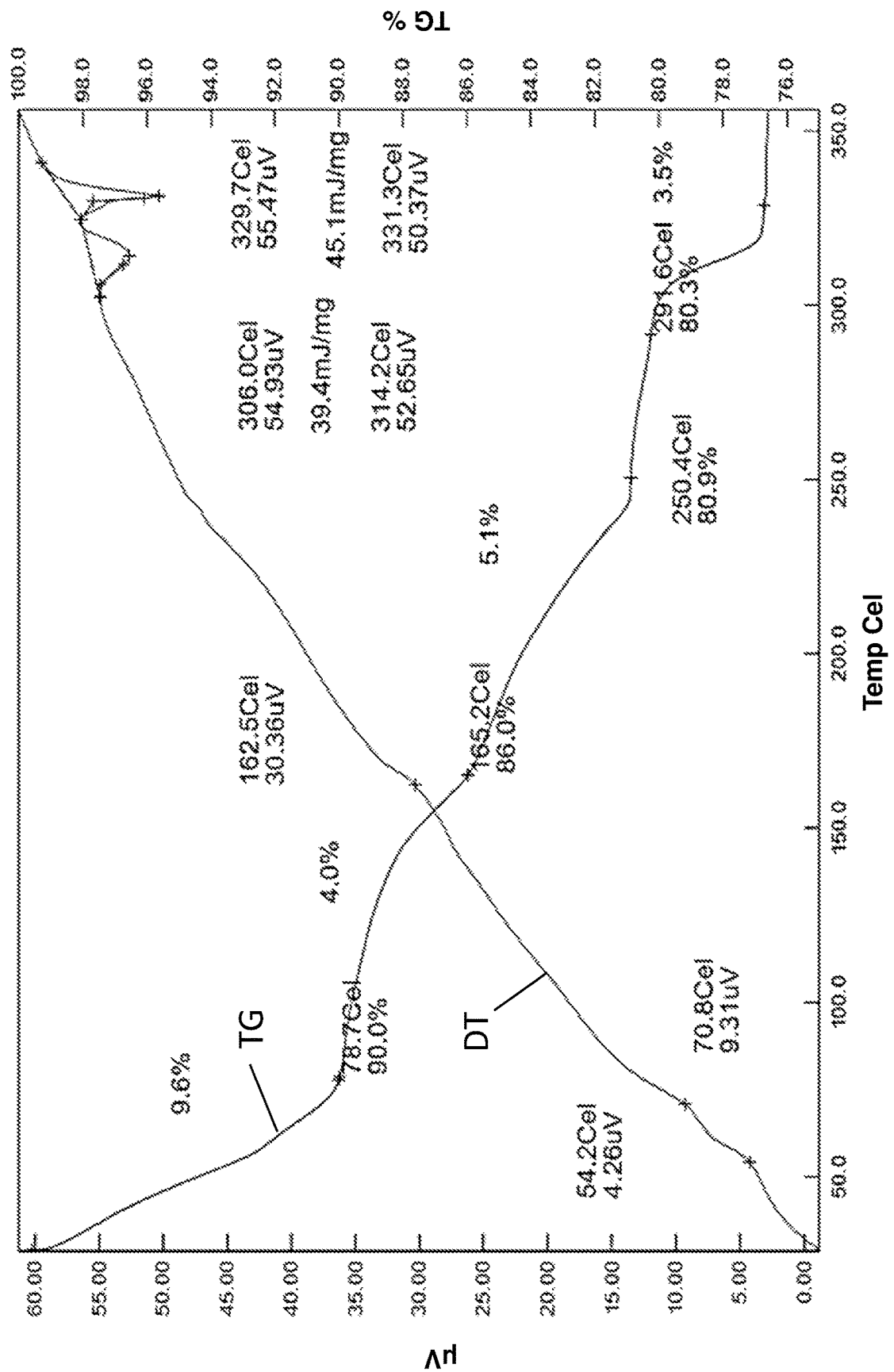
FIG. 34. TG/DTA thermogram of the BT-11 dihydrochloride Form 9. The thermal gravimetric trace (TG) trace and differential thermal (DT) trace are indicated.

BT-11 Form 9 was characterized via thermal gravimetric trace (FIG. 34). The thermal gravimetric trace (TG) showed a 9.6% loss in mass below around 90° C. Consecutive mass losses of 4.0 and 5.10 were observed. A broad endothermic event (onset ~306° C.) followed by a sharp endothermic event (onset ~330°) was observed.

Example 11. Crystal Form 10 of BT-11

Form 10 Preparation Methods

Form 3 was mixed with pH 1.2 buffer and shaken at 37° C. for 24 hours. pH 1.2 buffer was prepared mixing 0.2 M hydrochloric acid, 0.2M potassium chloride and water in an 18:6:1 ratio. Remaining solids were isolated by filtration and analyzed by XRPD to have a unique crystalline form, designated to be Form 10.

Characterization

BT-11 Form 10 was characterized via XRPD (FIG. 35). Diffraction peaks are presented in Table 18. Reduced cell parameters are presented in Table 19.

TABLE 18

Diffraction peaks observed for Form 10 of BT-11 dihydrochloride

| No. | Pos. [°2θ] | d-spacing [Å] | Height [cts] | Area [cts * °2θ] | Rel. Int [%] | h | k | l | Position Calc. [°2θ] |
| --- | --- | --- | --- | --- | --- | --- | --- | --- | --- |
| 1 | 8.9826 | 9.84494 | 684.44 | 77.73 | 100 | 1 | 2 | 0 | 8.9665 |
| 2 | 9.6234 | 9.19079 | 649.47 | 73.76 | 94.89 | 0 | 0 | 1 | 9.635 |
| 3 | 10.4558 | 8.46094 | 233.56 | 41.26 | 34.12 | 1 | 1 | −1 | 10.4658 |
| 4 | 12.9085 | 6.85826 | 154.48 | 19.49 | 22.57 | 2 | 2 | 0 | 12.9046 |
| 5 | 13.7375 | 6.44621 | 151.94 | 30.68 | 22.2 | 1 | 2 | 1 | 14.0958 |
| 6 | 14.5112 | 6.1042 | 238.72 | 60.25 | 34.88 | 0 | 3 | −1 | 14.4936 |
| 7 | 16.9278 | 5.23784 | 150.48 | 15.19 | 21.99 | 3 | 1 | −1 | 17.0269 |
| 8 | 17.5253 | 5.06059 | 313.71 | 47.5 | 45.83 | 1 | 4 | −1 | 17.4779 |
| 9 | 19.3197 | 4.59441 | 359.52 | 54.44 | 52.53 | 0 | 0 | 2 | 19.339 |
| 10 | 21.6188 | 4.11074 | 95.48 | 14.46 | 13.95 | 1 | 1 | 2 | 21.6128 |
| 11 | 23.2332 | 3.82862 | 358.23 | 54.24 | 52.34 | 3 | 2 | −2 | 23.1768 |
| 12 | 23.9357 | 3.71781 | 221.79 | 33.58 | 32.41 | 1 | 3 | 2 | 23.9437 |
| 13 | 25.4626 | 3.49824 | 299.3 | 60.43 | 43.73 | 2 | 2 | 2 | 25.4202 |
| 14 | 26.1681 | 3.40549 | 647.9 | 130.81 | 94.66 | 1 | 5 | −2 | 26.1582 |
| 15 | 27.5223 | 3.24094 | 569.78 | 100.66 | 83.25 | 4 | 3 | −2 | 27.5509 |
| 16 | 28.2002 | 3.16455 | 302.24 | 45.77 | 44.16 | 1 | 7 | 1 | 28.2007 |
| 17 | 29.1394 | 3.06211 | 195.24 | 23.43 | 28.53 | 5 | 3 | 0 | 29.1151 |
| 18 | 29.7769 | 3.00048 | 206.66 | 41.72 | 30.19 | 3 | 0 | −3 | 29.774 |
| 19 | 31.5542 | 2.83542 | 231.62 | 46.76 | 33.84 | 6 | 0 | −1 | 31.5527 |
| 20 | 33.2878 | 2.69161 | 85.5 | 25.89 | 12.49 | 4 | 2 | 2 | 33.2901 |

TABLE 19

Reduced Cell Parameters of Form 10 of BT-11 dihydrochloride.

| Cell Parameters | Value |
| --- | --- |
| a sigma [Å] | 17.03 |
| b sigma [Å] | 24.55 |
| c sigma [Å] | 9.45 |
| alpha (sigma) [°] | 90.00 |
| beta (sigma) [°] | 103.98 |
| gamma (sigma) [°] | 90.00 |

Example 12. Crystal Form 11 of BT-11

Form 11 Preparation Methods

N-methylpyrrolidone or 90:10 (v/v) mixtures of NMP:ethanol, NMP:2-propanol, NMP:1-propanol, NMP:acetonitrile, NMP:acetone, NMP:ethyl acetate, or NMP:water were added to BT-11 free base in 24:1, 36:1, 34:1, 34:1, 45:1, 36:1, 36:1, or 26:1 (w/v) ratios, respectively, to form slurries by stirring for 1 hour at 50° C. The temperature was decreased to 40° C., over approximately 10 minutes. 2.2 equivalents of HCl were added dropwise. The slurries were stirred at 40° C. for approximately 90 minutes. The slurries were cooled to 5° C. at a rate of 0.1° C./min and temperature cycled between 5° C. and 40° C. for 1 cycle (0.1° C./min) prior to holding at 5° C. for approximately 6 hours. Solid materials were filtered and dried under vacuum at approximately 40° C. for approximately 21 hours. Isolated material analyzed by XRPD to have a unique crystalline form, designated to be Form 11.

Characterization

BT-11 Form 11 was characterized via XRPD (FIG. 36).

Example 13. Crystal Form 12 of BT-11

Form 12 Preparation Methods

A 90:10 (v/v) mixture of NMP:methanol was added to BT-11 free base in 32:1 to form a slurry by stirring for 1 hour at 50° C. The temperature was decreased to 40° C., over approximately 10 minutes. 2.2 equivalents of HCl were added dropwise. The slurries were stirred at 40° C. for approximately 90 minutes. The slurries were cooled to 5° C. at a rate of 0.1° C./min and temperature cycled between 5° C. and 40° C. for 1 cycle (0.1° C./min) prior to holding at 5° C. for approximately 6 hours. Solid materials were filtered and dried under vacuum at approximately 40° C. for approximately 21 hours. Isolated material analyzed by XRPD to have a unique crystalline form, designated to be Form 12.

Alternatively, N-methylpyrrolidone:methanol (75:25) was added to BT-11 free base in a 42:1 (w/v) ratio to form a slurry by stirring for 1 hour at 50° C. BT-11 dihydrochloride Form 2 was seeded into the mixture (approximately 4% weight). Approximately 2.2 equivalents of HCl were added dropwise. An additional approximate 4% weight of BT-11 dihydrochloride Form 2 was added. The slurry was stirred at 50° C. for approximately 18 hours prior to cooling to 5° C. at a rate of 0.1° C./min and holding at 5° C. for approximately 18 hours. Solid materials were filtered. Isolated material analyzed by XRPD to have a unique crystalline form, designated to be Form 12.

Characterization

BT-11 Form 12 was characterized via XRPD (FIG. 37).

Example 14. Crystal Form 13 of BT-11

Form 13 Preparation Methods

DMSO:water (50:50) was added to BT-11 free base in a 59:1 (w/v) ratio to form a slurry by stirring for 1 hour at 50° C. BT-11 dihydrochloride Form 2 was seeded into the mixture (approximately 4% weight). Approximately 2.2 equivalents of HCl were added in a single aliquot. An additional approximate 4% weight of BT-11 dihydrochloride Form 2 was added. The slurry was stirred at 50° C. for approximately 18 hours prior to cooling to 5° C. at a rate of 0.1° C./min and holding at 5° C. for approximately 18 hours. Solid materials were filtered. Isolated material analyzed by XRPD to have a unique crystalline form, designated to be Form 13.

Characterization

BT-11 Form 13 was characterized via XRPD (FIG. 38).

Example 15. Pharmacokinetic Analysis

Experimental Methods

BT-11 Form 0, Form 1, and Form 2 were orally dosed to male and female mice (n=4) to provide 8 mg/kg. Plasma was collected at 1, 2, and 4 hours post-dose. At 4 hours post-dose, colons were excised and washed in PBS. Tissues were then homogenized by Fast-Prep24 instrument. Plasma and tissue homogenate were prepared by acetonitrile-based liquid-liquid extraction. BT-11 concentrations were determined by LC/MS/MS analysis using a linear calibration curve.

Results

Bioanalytical results of maximum concentration in plasma and colonic concentrations 4 hours post-dose are presented in Table 20.

TABLE 20

Bioanalytical analysis of BT-11 in plasma and colonic tissue.

| Form | Form 0 | Form 1 | Form 2 |
|---|---|---|---|
| Plasma BT-11 $C_{max}$ (ng/mL) | 186 | 177 | 41 |
| Colon BT-11 Concentration (ng/mg) | 1275 | 3000 | 4470 |

Exemplary Embodiments of the Invention

1. A crystal form of piperazine-1,4-diylbis((6-(1H-benzo[d]imidazo-2-yl)pyridine-2-yl)methanone) having a peak within at least one 2θ value range selected from 12.4 to 12.8, 16.9 to 17.3, 20.5 to 20.9, 22.1 to 22.5, 23.2 to 23.6, and 28.2 to 28.6 degrees in an X-ray powder diffraction pattern obtained using Cu K alpha radiation.
2. The crystal form of embodiment 1, wherein the crystal form of piperazine-1,4-diylbis((6-(1H-benzo[d]imidazo-2-yl)pyridine-2-yl)methanone) has a peak within one or both 2θ value range(s) selected from 12.4 to 12.8 and 16.9 to 17.3.
3. The crystal form of any one of embodiments 1-2, wherein the crystal form of piperazine-1,4-diylbis((6-(1H-benzo[d]imidazo-2-yl)pyridine-2-yl)methanone) has a peak within a 2θ value range of 12.4 to 12.8 degrees.
4. The crystal form of any one of embodiments 1-3, wherein the crystal form of piperazine-1,4-diylbis((6-(1H-benzo[d]imidazo-2-yl)pyridine-2-yl)methanone) has a peak within a 2θ value range of 16.9 to 17.3 degrees.
5. The crystal form of any one of embodiments 1-4, wherein the crystal form of piperazine-1,4-diylbis((6-(1H-benzo[d]imidazo-2-yl)pyridine-2-yl)methanone) has a peak within at least one, at least two, at least three, or each 2θ value range(s) selected from 20.5 to 20.9, 22.1 to 22.5, 23.2 to 23.6, and 28.2 to 28.6 degrees.
6. The crystal form of any one of embodiments 1-5, wherein the crystal form of piperazine-1,4-diylbis((6-(1H-benzo[d]imidazo-2-yl)pyridine-2-yl)methanone) has a peak within each 2θ value range selected from 12.4 to 12.8, 16.9 to 17.3, 20.5 to 20.9, 22.1 to 22.5, 23.2 to 23.6, and 28.2 to 28.6 degrees.
7. The crystal form of any one of embodiments 1-6, wherein the crystal form of piperazine-1,4-diylbis((6-(1H-benzo[d]imidazo-2-yl)pyridine-2-yl)methanone) further has a peak within a 2θ value range of 9.8 to 10.2 degrees.
8. The crystal form of any one of embodiments 1-7, wherein the crystal form of piperazine-1,4-diylbis((6-(1H-benzo[d]imidazo-2-yl)pyridine-2-yl)methanone) further has a peak within a 2θ value range of 14.1 to 14.5 degrees.
9. The crystal form of any one of embodiments 1-8, wherein the crystal form of piperazine-1,4-diylbis((6-(1H-benzo[d]imidazo-2-yl)pyridine-2-yl)methanone) further has a peak within a 2θ value range of 19.2 to 19.6 degrees.
10. The crystal form of any one of embodiments 1-9, wherein the crystal form of piperazine-1,4-diylbis((6-(1H-benzo[d]imidazo-2-yl)pyridine-2-yl)methanone) further has a peak within a 2θ value range of 25.3 to 25.7 degrees.
11. The crystal form of any one of embodiments 1-10, wherein the crystal form of piperazine-1,4-diylbis((6-(1H-benzo[d]imidazo-2-yl)pyridine-2-yl)methanone) has a Dv50 within a range of 13-55 μm, a Dv10 within a range of 5-28 μm, and a Dv90 within a range of 18-117 μm, with the proviso that the Dv10 is a lower value than the Dv50 and the Dv50 is a lower value than the Dv90.
12. The crystal form of any one of embodiments 1-11, wherein the crystal form of piperazine-1,4-diylbis((6-(1H-benzo[d]imidazo-2-yl)pyridine-2-yl)methanone)

has an X-ray powder diffraction pattern obtained using Cu K alpha radiation substantially similar to any pattern provided in any one of FIGS. 11, 12, 13, 14A, and 14B.

13. The crystal form of any one of embodiments 1-12, wherein the crystal form of piperazine-1,4-diylbis((6-(1H-benzo[d]imidazo-2-yl)pyridine-2-yl)methanone) has unit cell dimensions a=12.81 Å, α=90°, b=12.56 Å, β=105.25°, c=9.48 Å, γ=90°.

14. A crystal form of piperazine-1,4-diylbis((6-(1H-benzo[d]imidazo-2-yl)pyridine-2-yl)methanone) with the unit cell dimensions a=12.81 Å, α=90°, b=12.56 Å, p=105.25°, c=9.48 Å, γ=90°.

15. A crystal form of piperazine-1,4-diylbis((6-(1H-benzo[d]imidazo-2-yl)pyridine-2-yl)methanone) having a peak within at least one 2θ value range selected from 10.1 to 10.5, 13.8 to 14.2, 16.9 to 17.3, 23.7 to 24.1, 24.3 to 24.7, 27.7 to 28.1, and 28.8 to 29.2 degrees in an X-ray powder diffraction pattern obtained using Cu K alpha radiation.

16. The crystal form of embodiment 15, wherein the piperazine-1,4-diylbis((6-(1H-benzo[d]imidazo-2-yl)pyridine-2-yl)methanone) has a peak within at least one, at least two, at least three, or each 2θ value range(s) selected from 10.1 to 10.5, 16.9 to 17.3, 23.7 to 24.1, and 28.8 to 29.2 degrees.

17. The crystal form of any one of embodiments 15-16, wherein the crystal form of piperazine-1,4-diylbis((6-(1H-benzo[d]imidazo-2-yl)pyridine-2-yl)methanone) has a peak within a 2θ value range of 10.1 to 10.5 degrees.

18. The crystal form of any one of embodiments 15-17, wherein the crystal form of piperazine-1,4-diylbis((6-(1H-benzo[d]imidazo-2-yl)pyridine-2-yl)methanone) has a peak within a 2θ value range of 16.9 to 17.3 degrees.

19. The crystal form of any one of embodiments 15-18, wherein the crystal form of piperazine-1,4-diylbis((6-(1H-benzo[d]imidazo-2-yl)pyridine-2-yl)methanone) has a peak within a 2θ value range of 23.7 to 24.1 degrees.

20. The crystal form of any one of embodiments 15-19, wherein the crystal form of piperazine-1,4-diylbis((6-(1H-benzo[d]imidazo-2-yl)pyridine-2-yl)methanone) has a peak within a 2θ value range of 28.8 to 29.2 degrees.

21. The crystal form of any one of embodiments 15-20, wherein the crystal form of piperazine-1,4-diylbis((6-(1H-benzo[d]imidazo-2-yl)pyridine-2-yl)methanone) has peak within at least one, at least two, or three 2θ value range(s) selected from 13.8 to 14.2, 24.3 to 24.7, and 27.7 to 28.1 degrees.

22. The crystal form of any one of embodiments 15-21, wherein the crystal form of piperazine-1,4-diylbis((6-(1H-benzo[d]imidazo-2-yl)pyridine-2-yl)methanone) has a peak within each 2θ value range selected from 10.1 to 10.5, 13.8 to 14.2, 16.9 to 17.3, 23.7 to 24.1, 24.3 to 24.7, 27.7 to 28.1, and 28.8 to 29.2 degrees in an X-ray powder diffraction pattern obtained using Cu K alpha radiation.

23. The crystal form of any one of embodiments 15-22, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to any pattern provided in any one of FIGS. 21A, 21B, 21C, and 21D.

24. The crystal form of any one of embodiments 15-23, wherein the crystal form of piperazine-1,4-diylbis((6-(1H-benzo[d]imidazo-2-yl)pyridine-2-yl)methanone) has unit cell dimensions a=9.30 Å, α=71.15°, b=11.78 Å, β=106.99°, c=10.20 Å, γ=108.35°.

25. A crystal form of piperazine-1,4-diylbis((6-(1H-benzo[d]imidazo-2-yl)pyridine-2-yl)methanone) with the unit cell dimensions a=9.30 Å, α=71.15°, b=11.78 Å, p=106.99°, c=10.20 Å, γ=108.35°.

26. A crystal form of piperazine-1,4-diylbis((6-(1H-benzo[d]imidazo-2-yl)pyridine-2-yl)methanone) having a peak within at least one, at least two, at least three, at least four, at least five, at least six, or each 2θ value range(s) selected from 5.7 to 6.1, 9.6 to 10.0, 14.0 to 14.4, 19.4 to 19.8, 23.0 to 23.4, 24.1 to 24.5, and 27.9 to 28.3 degrees in an X-ray powder diffraction pattern obtained using Cu K alpha radiation.

27. The crystal form of embodiment 26, wherein the crystal form of piperazine-1,4-diylbis((6-(1H-benzo[d]imidazo-2-yl)pyridine-2-yl)methanone) has a peak within a 2θ value range of 5.7 to 6.1.

28. The crystal form of any one of embodiments 26-27, wherein the crystal form of piperazine-1,4-diylbis((6-(1H-benzo[d]imidazo-2-yl)pyridine-2-yl)methanone) has a peak within each 2θ value range selected from 5.7 to 6.1, 9.6 to 10.0, 14.0 to 14.4, 19.4 to 19.8, 23.0 to 23.4, 24.1 to 24.5, and 27.9 to 28.3 degrees in an X-ray powder diffraction pattern obtained using Cu K alpha radiation.

29. The crystal form of any one of embodiments 26-28, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to any pattern provided in any one of FIGS. 4A and 4B.

30. The crystal form of any one of claims 26-29, wherein the crystal form of piperazine-1,4-diylbis((6-(1H-benzo[d]imidazo-2-yl)pyridine-2-yl)methanone) has unit cell dimensions a=6.97 Å, α=98.26°, b=15.17 Å, β=101.74°, c=9.31 Å, γ=89.23°.

31. A crystal form of piperazine-1,4-diylbis((6-(1H-benzo[d]imidazo-2-yl)pyridine-2-yl)methanone) with the unit cell dimensions a=6.97 Å, α=98.26°, b=15.17 Å, β=101.74°, c=9.31 Å, γ=89.23°.

32. A crystal form of piperazine-1,4-diylbis((6-(1H-benzo[d]imidazo-2-yl)pyridine-2-yl)methanone) having a peak within at least one, at least two, at least three, at least four, at least five, or each 2θ value range(s) selected from 12.0 to 12.4, 15.0 to 15.4, 15.3 to 15.7, 21.9 to 22.3, 22.2 to 22.6, and 28.0 to 28.4 degrees in an X-ray powder diffraction pattern obtained using Cu K alpha radiation.

33. The crystal form of embodiment 32, wherein the crystal form of piperazine-1,4-diylbis((6-(1H-benzo[d]imidazo-2-yl)pyridine-2-yl)methanone) has a peak within each 2θ value range selected from 12.0 to 12.4, 15.0 to 15.4, 15.3 to 15.7, 21.9 to 22.3, 22.2 to 22.6, and 28.0 to 28.4 degrees in an X-ray powder diffraction pattern obtained using Cu K alpha radiation.

34. The crystal form of any one of embodiments 32-33, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to the pattern provided in FIG. 1.

35. A crystal form of piperazine-1,4-diylbis((6-(1H-benzo[d]imidazo-2-yl)pyridine-2-yl)methanone) having a peak within at least one, at least two, at least three, or each 2θ value range(s) selected from 6.9 to 7.3, 12.9 to 13.3, 23.4 to 23.8, and 27.3 to 27.7 degrees in an X-ray powder diffraction pattern obtained using Cu K alpha radiation.
36. The crystal form of embodiment 35, wherein the crystal form of piperazine-1,4-diylbis((6-(1H-benzo[d]imidazo-2-yl)pyridine-2-yl)methanone) has a peak within each 2θ value range selected from 6.9 to 7.3, 12.9 to 13.3, 23.4 to 23.8, and 27.3 to 27.7 degrees in an X-ray powder diffraction pattern obtained using Cu K alpha radiation.
37. The crystal form of any one of embodiments 35-36, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to the pattern provided in FIG. 25.
38. A crystal form of piperazine-1,4-diylbis((6-(1H-benzo[d]imidazo-2-yl)pyridine-2-yl)methanone) having a peak within at least one, at least two, at least three, or each 2θ value range(s) selected from 3.5 to 3.9, 7.2 to 7.6, 14.6 to 15.0, and 24.5 to 24.9 degrees in an X-ray powder diffraction pattern obtained using Cu K alpha radiation.
39. The crystal form of embodiment 38, wherein the crystal form of piperazine-1,4-diylbis((6-(1H-benzo[d]imidazo-2-yl)pyridine-2-yl)methanone) has a peak within each 2θ value range selected from 3.5 to 3.9, 7.2 to 7.6, 14.6 to 15.0, and 24.5 to 24.9 degrees in an X-ray powder diffraction pattern obtained using Cu K alpha radiation.
40. The crystal form of any one of embodiments 38-39, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to the pattern provided in FIG. 26.
41. A crystal form of piperazine-1,4-diylbis((6-(1H-benzo[d]imidazo-2-yl)pyridine-2-yl)methanone) having a peak within at least one, at least two, or each 2θ value range(s) selected from 9.2 to 9.6, 26.6 to 27.0, and 27.6 to 28.0 degrees in an X-ray powder diffraction pattern obtained using Cu K alpha radiation.
42. The crystal form of embodiment 41, wherein the crystal form of piperazine-1,4-diylbis((6-(1H-benzo[d]imidazo-2-yl)pyridine-2-yl)methanone) has a peak within each 2θ value range selected from 9.2 to 9.6, 26.6 to 27.0, and 27.6 to 28.0 degrees in an X-ray powder diffraction pattern obtained using Cu K alpha radiation.
43. The crystal form of any one of embodiments 41-42, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to the pattern provided in FIG. 28.
44. A crystal form of piperazine-1,4-diylbis((6-(1H-benzo[d]imidazo-2-yl)pyridine-2-yl)methanone) having a peak within at least one, at least two, at least three, at least four, or each 2θ value range(s) selected from 9.9 to 10.3, 12.1 to 12.5, 20.5 to 20.9, 25.7 to 26.1, and 26.9 to 27.3 degrees in an X-ray powder diffraction pattern obtained using Cu K alpha radiation.
45. The crystal form of embodiment 44, wherein the crystal form of piperazine-1,4-diylbis((6-(1H-benzo[d]imidazo-2-yl)pyridine-2-yl)methanone) has a peak within each 2θ value range selected from 9.9 to 10.3, 12.1 to 12.5, 20.5 to 20.9, 25.7 to 26.1, and 26.9 to 27.3 degrees in an X-ray powder diffraction pattern obtained using Cu K alpha radiation.
46. The crystal form of any one of embodiments 44-45, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to the pattern provided in FIG. 30.
47. A crystal form of piperazine-1,4-diylbis((6-(1H-benzo[d]imidazo-2-yl)pyridine-2-yl)methanone) having a peak within at least one, at least two, at least three, at least four, or each 2θ value range(s) selected from 7.4 to 7.8, 13.1 to 13.5, 22.1 to 22.5, 23.9 to 24.3, and 25.1 to 25.5 degrees in an X-ray powder diffraction pattern obtained using Cu K alpha radiation.
48. The crystal form of embodiment 47, wherein the crystal form of piperazine-1,4-diylbis((6-(1H-benzo[d]imidazo-2-yl)pyridine-2-yl)methanone) has a peak within each 2θ value range selected from 7.4 to 7.8, 13.1 to 13.5, 22.1 to 22.5, 23.9 to 24.3, and 25.1 to 25.5 degrees in an X-ray powder diffraction pattern obtained using Cu K alpha radiation.
49. The crystal form of any one of embodiments 47-48, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to the pattern provided in FIG. 31.
50. A crystal form of piperazine-1,4-diylbis((6-(1H-benzo[d]imidazo-2-yl)pyridine-2-yl)methanone) having a peak within at least one, at least two, at least three, or each 2θ value range(s) selected from 9.9 to 10.3, 12.1 to 12.5, 25.8 to 26.2, and 26.9 to 27.3 degrees in an X-ray powder diffraction pattern obtained using Cu K alpha radiation.
51. The crystal form of embodiment 50, wherein the crystal form of piperazine-1,4-diylbis((6-(1H-benzo[d]imidazo-2-yl)pyridine-2-yl)methanone) has a peak within each 2θ value range selected from 9.9 to 10.3, 12.1 to 12.5, 25.8 to 26.2, and 26.9 to 27.3 degrees in an X-ray powder diffraction pattern obtained using Cu K alpha radiation.
52. The crystal form of any one of embodiments 50-51, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to the pattern provided in FIG. 33.
53. A crystal form of piperazine-1,4-diylbis((6-(1H-benzo[d]imidazo-2-yl)pyridine-2-yl)methanone) having a peak within at least one, at least two, at least three, at least four, at least five, or each 2θ value range(s) selected from 8.8 to 9.2, 9.4 to 9.8, 19.1 to 19.5, 23.0 to 23.4, 26.0 to 26.4, and 27.3 to 27.7 degrees in an X-ray powder diffraction pattern obtained using Cu K alpha radiation.
54. The crystal form of embodiment 53, wherein the crystal form of piperazine-1,4-diylbis((6-(1H-benzo[d]imidazo-2-yl)pyridine-2-yl)methanone) has a peak within each 2θ value range selected from 8.8 to 9.2, 9.4 to 9.8, 19.1 to 19.5, 23.0 to 23.4, 26.0 to 26.4, and 27.3 to 27.7 degrees in an X-ray powder diffraction pattern obtained using Cu K alpha radiation.
55. The crystal form of any one of embodiments 53-54, wherein the crystal form of piperazine-1,4-diylbis((6-

(1H-benzo[d]imidazo-2-yl)pyridine-2-yl)methanone) has an X-ray powder diffraction pattern obtained using Cu K alpha radiation substantially similar to the pattern provided in FIG. 35.

56. A crystal form of piperazine-1,4-diylbis((6-(1H-benzo[d]imidazo-2-yl)pyridine-2-yl)methanone) having a peak within at least one, at least two, at least three, at least four, or each 2θ value range(s) selected from 15.6 to 16.0, 19.4 to 19.8, 21.4 to 21.8, 23.3 to 23.7, and 27.1 to 27.5 degrees in an X-ray powder diffraction pattern obtained using Cu K alpha radiation.

57. The crystal form of embodiment 56, wherein the crystal form of piperazine-1,4-diylbis((6-(1H-benzo[d]imidazo-2-yl)pyridine-2-yl)methanone) has a peak within each 2θ value range selected from 15.6 to 16.0, 19.4 to 19.8, 21.4 to 21.8, 23.3 to 23.7, and 27.1 to 27.5 degrees in an X-ray powder diffraction pattern obtained using Cu K alpha radiation.

58. The crystal form of any one of embodiments 56-57, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to any pattern provided in FIG. 36.

59. A crystal form of piperazine-1,4-diylbis((6-(1H-benzo[d]imidazo-2-yl)pyridine-2-yl)methanone) having a peak within at least one, at least two, at least three, or each 2θ value range(s) selected from 11.6 to 12.0, 18.3 to 18.7, 27.1 to 27.5, 28.0 to 28.4 degrees in an X-ray powder diffraction pattern obtained using Cu K alpha radiation.

60. The crystal form of embodiment 59, wherein the crystal form of piperazine-1,4-diylbis((6-(1H-benzo[d]imidazo-2-yl)pyridine-2-yl)methanone) has a peak within each 2θ value range selected from 11.6 to 12.0, 18.3 to 18.7, 27.1 to 27.5, 28.0 to 28.4 degrees in an X-ray powder diffraction pattern obtained using Cu K alpha radiation.

61. The crystal form of any one of embodiments 59-60, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to the pattern provided in FIG. 37.

62. A crystal form of piperazine-1,4-diylbis((6-(1H-benzo[d]imidazo-2-yl)pyridine-2-yl)methanone) having a peak within at least one, at least two, or each 2θ value range(s) selected from 9.4 to 9.8, 17.0 to 17.4, and 24.5 to 24.9 degrees in an X-ray powder diffraction pattern obtained using Cu K alpha radiation.

63. The crystal form of embodiment 62, wherein the crystal form of piperazine-1,4-diylbis((6-(1H-benzo[d]imidazo-2-yl)pyridine-2-yl)methanone) has a peak within each 2θ value range selected from 9.4 to 9.8, 17.0 to 17.4, and 24.5 to 24.9 degrees in an X-ray powder diffraction pattern obtained using Cu K alpha radiation.

64. The crystal form of any one of embodiments 62-63, wherein the crystal form of piperazine-1,4-diylbis((6-(1H-benzo[d]imidazo-2-yl)pyridine-2-yl)methanone) has an X-ray powder diffraction pattern obtained using Cu K alpha radiation substantially similar to the pattern provided in FIG. 38.

65. A composition comprising the crystal form of piperazine-1,4-diylbis((6-(1H-benzo[d]imidazo-2-yl)pyridine-2-yl)methanone) of any one of embodiments 1-64.

66. The composition of embodiment 65, wherein the composition comprises the crystal form of piperazine-1,4-diylbis((6-(1H-benzo[d]imidazo-2-yl)pyridine-2-yl)methanone) in an amount of at least 80% w/w of the of the total amount of crystalized piperazine-1,4-diylbis((6-(1H-benzo[d]imidazo-2-yl)pyridine-2-yl)methanone) present in the composition.

67. The composition of any one of embodiments 65-66, further comprising a pharmaceutically acceptable carrier.

68. A method of administering piperazine-1,4-diylbis((6-(1H-benzo[d]imidazo-2-yl)pyridine-2-yl)methanone), the method comprising administering the composition of any one of embodiments 65-68 to a subject.

69. The method of embodiment 68, wherein the subject is a subject suffering from a disease.

70. The method of embodiment 69, wherein the disease comprises a chronic inflammatory, immune-mediated, or autoimmune disease.

71. The method of any one of embodiments 69-70, wherein the disease comprises a disease of the gastrointestinal tract.

72. The method of any one of embodiments 69-71, wherein the disease comprises inflammatory bowel disease.

73. The method of any one of embodiments 69-71, wherein the disease comprises an eosinophilic disorder of the gastrointestinal tract.

74. The method of any one of embodiments 69-70, wherein the disease comprises a disease of a surface tissue.

75. The method of embodiment 74, wherein the disease comprises any one or more of psoriasis, cutaneous lupus erythematosus, dermatomyositis, pemphigoid, pemphigus, scleroderma, vasculitis, epidermolysis bullosa acquisita, vitiligo, lichen planus, scleritis, dermatitis or eczema, erythema nodosum, pyoderma gangrenosum, skin fissures, acne, enterocutaneous fistula, skin tags, canker sores, acrodermatitis enteropathica, pyoderma vegetans, leukocytoclastic vasculitis, anal fissures, Sweet's syndrome, rosacea, alopecia, keratoderma blennorrhagica, rosacea, cold sores, urticaria, actinic keratosis, carbuncle, cellulitis, ichthyosis vulgaris, skin infection, malar rash, photosensitivity, livedo reticularis, livedo reticularis, oral and nasal ulcers, purpura, mucositis, hemorrhoids, burn, and sunburn.

76. The method of any one of embodiments 69-75, wherein the pharmaceutical composition is administered in an amount effective to treat the disease.

77. A process for preparing the crystal form of piperazine-1,4-diylbis((6-(1H-benzo[d]imidazo-2-yl)pyridine-2-yl)methanone) of any one of embodiments 1-14, the process comprising mixing piperazine-1,4-diylbis((6-(1H-benzo[d]imidazo-2-yl)pyridine-2-yl)methanone) in a solvent to form a slurry.

78. The process of embodiment 77, wherein the solvent comprises at least one of methanol, 2-ethoxyethanol, methyl isobutyl ketone, N-methylpyrrolidone, and dimethylsulfoxide.

79. The process of embodiment 77, wherein the solvent is a mixture of dimethylsulfoxide, methanol, and water.

80. The process of embodiment 79, wherein the mixture of dimethylsulfoxide, methanol, and water is in a ratio of 45-55:35-45:5-15 (dimethylsulfoxide:methanol:water), such as 50:40:10.

81. The process of embodiment 77, wherein the solvent is N-methylpyrrolidone or a mixture of N-methylpyrrolidone and one or more of methanol, ethanol, 2-propanol, 1-propanol, acetonitrile, acetone, ethyl acetate, and water.

82. The process of embodiment 77, wherein the solvent is selected from the group consisting of 2-ethoxyethanol, methyl isobutyl ketone, and a mixture of methanol and water.

83. The process of any one of embodiments 77-82, further comprising isolating crystallized material from the slurry to obtain isolated material; washing the isolated material with a solvent comprising methanol or N-methylpyrrolidone to obtain washed material; and drying the washed material to obtain dried material comprising the crystal form of piperazine-1,4-diylbis((6-(1H-benzo[d]imidazo-2-yl)pyridine-2-yl)methanone).

84. The process of any one of embodiments 77-83, further comprising seeding the slurry with the crystal form of piperazine-1,4-diylbis((6-(1H-benzo[d]imidazo-2-yl)pyridine-2-yl)methanone).

85. The process of any one of embodiments 77-84, further comprising cyclically heating and cooling the slurry.

86. A process for preparing the crystal form of piperazine-1,4-diylbis((6-(1H-benzo[d]imidazo-2-yl)pyridine-2-yl)methanone) of any one of embodiments 15-25, the process comprising mixing piperazine-1,4-diylbis((6-(1H-benzo[d]imidazo-2-yl)pyridine-2-yl)methanone) in a solvent to form a slurry.

87. The process of embodiment 86, wherein solvent comprises at least one of tetrahydrofuran, 1,4-dioxane, 1-butanol, 1-propanol, 2-methyl THf, butyl acetate, dichloromethane, ethyl acetate, isopropyl alcohol, methanol, methyl ethyl ketone, and tert-butyl methyl ether.

We claim:

1. A composition comprising a crystal form of piperazine-1,4-diylbis((6-(1H-benzo[d]imidazo-2-yl)pyridine-2-yl)methanone) having a peak within at least one 2θ value range selected from 12.4 to 12.8, 16.9 to 17.3, 20.5 to 20.9, 22.1 to 22.5, 23.2 to 23.6, and 28.2 to 28.6 degrees in an X-ray powder diffraction pattern obtained using Cu K alpha radiation, wherein the crystal form of the piperazine-1,4-diylbis((6-(1H-benzo[d]imidazo-2-yl)pyridine-2-yl)methanone) has a peak within a 2θ value range of 12.4 to 12.8 degrees, wherein the composition comprises the crystal form of the piperazine-1,4-diylbis((6-(1H-benzo[d]imidazo-2-yl)pyridine-2-yl)methanone) in an amount of at least 85% w/w of the total amount of crystalized piperazine-1,4-diylbis((6-(1H-benzo[d]imidazo-2-yl)pyridine-2-yl)methanone) present in the composition.

2. The composition of claim 1, wherein the composition comprises the crystal form of the piperazine-1,4-diylbis((6-(1H-benzo[d]imidazo-2-yl)pyridine-2-yl)methanone) in an amount of at least 90% w/w of the total amount of crystalized piperazine-1,4-diylbis((6-(1H-benzo[d]imidazo-2-yl)pyridine-2-yl)methanone) present in the composition.

3. The composition of claim 1, wherein the composition comprises the crystal form of the piperazine-1,4-diylbis((6-(1H-benzo[d]imidazo-2-yl)pyridine-2-yl)methanone) in an amount of at least 95% w/w of the total amount of crystalized piperazine-1,4-diylbis((6-(1H-benzo[d]imidazo-2-yl)pyridine-2-yl)methanone) present in the composition.

4. The composition of claim 1, wherein the composition comprises the crystal form of the piperazine-1,4-diylbis((6-(1H-benzo[d]imidazo-2-yl)pyridine-2-yl)methanone) in an amount of at least 99% w/w of the total amount of crystalized piperazine-1,4-diylbis((6-(1H-benzo[d]imidazo-2-yl)pyridine-2-yl)methanone) present in the composition.

5. The composition of claim 1, wherein the composition comprises the crystal form of the piperazine-1,4-diylbis((6-(1H-benzo[d]imidazo-2-yl)pyridine-2-yl)methanone) in an amount of 100% w/w of the total amount of crystalized piperazine-1,4-diylbis((6-(1H-benzo[d]imidazo-2-yl)pyridine-2-yl)methanone) present in the composition.

6. The composition of claim 1, wherein the crystal form of the piperazine-1,4-diylbis((6-(1H-benzo[d]imidazo-2-yl)pyridine-2-yl)methanone) has a peak within each 2θ value range selected from 12.4 to 12.8, 16.9 to 17.3, 20.5 to 20.9, 22.1 to 22.5, 23.2 to 23.6, and 28.2 to 28.6 degrees.

7. The composition of claim 6, wherein the composition comprises the crystal form of the piperazine-1,4-diylbis((6-(1H-benzo[d]imidazo-2-yl)pyridine-2-yl)methanone) in an amount of at least 95% w/w of the total amount of crystalized piperazine-1,4-diylbis((6-(1H-benzo[d]imidazo-2-yl)pyridine-2-yl)methanone) present in the composition.

8. The composition of claim 6, wherein the composition comprises the crystal form of the piperazine-1,4-diylbis((6-(1H-benzo[d]imidazo-2-yl)pyridine-2-yl)methanone) in an amount of at least 99% w/w of the total amount of crystalized piperazine-1,4-diylbis((6-(1H-benzo[d]imidazo-2-yl)pyridine-2-yl)methanone) present in the composition.

9. The composition of claim 6, wherein the crystal form of the piperazine-1,4-diylbis((6-(1H-benzo[d]imidazo-2-yl)pyridine-2-yl)methanone) further has:
a peak within a 2θ value range of 9.8 to 10.2 degrees;
a peak within a 2θ value range of 14.1 to 14.5 degrees;
a peak within a 2θ value range of 19.2 to 19.6 degrees; and
a peak within a 2θ value range of 25.3 to 25.7 degrees.

10. The composition of claim 9, wherein the composition comprises the crystal form of the piperazine-1,4-diylbis((6-(1H-benzo[d]imidazo-2-yl)pyridine-2-yl)methanone) in an amount of at least 95% w/w of the total amount of crystalized piperazine-1,4-diylbis((6-(1H-benzo[d]imidazo-2-yl)pyridine-2-yl)methanone) present in the composition.

11. The composition of claim 9, wherein the composition comprises the crystal form of the piperazine-1,4-diylbis((6-(1H-benzo[d]imidazo-2-yl)pyridine-2-yl)methanone) in an amount of at least 99% w/w of the total amount of crystalized piperazine-1,4-diylbis((6-(1H-benzo[d]imidazo-2-yl)pyridine-2-yl)methanone) present in the composition.

12. The composition of claim 9, wherein the composition comprises the crystal form of the piperazine-1,4-diylbis((6-(1H-benzo[d]imidazo-2-yl)pyridine-2-yl)methanone) in an amount of 100% w/w of the total amount of crystalized piperazine-1,4-diylbis((6-(1H-benzo[d]imidazo-2-yl)pyridine-2-yl)methanone) present in the composition.

13. The composition of claim 4, wherein the crystal form of the piperazine-1,4-diylbis((6-(1H-benzo[d]imidazo-2-yl)pyridine-2-yl)methanone) has an X-ray powder diffraction pattern obtained using Cu K alpha radiation substantially similar to any pattern provided in any one of FIGS. 11, 12, 13, 14A, and 14B.

14. The composition of claim 13, wherein the composition comprises the crystal form of the piperazine-1,4-diylbis((6-(1H-benzo[d]imidazo-2-yl)pyridine-2-yl)methanone) in an amount of 100% w/w of the total amount of crystalized piperazine-1,4-diylbis((6-(1H-benzo[d]imidazo-2-yl)pyridine-2-yl)methanone) present in the composition.

15. The composition of claim 4, wherein the crystal form of piperazine-1,4-diylbis((6-(1H-benzo[d]imidazo-2-yl)

pyridine-2-yl)methanone) has unit cell dimensions a=12.81 Å, α=90°, b=12.56 Å, β=105.25°, c=9.48 Å, γ=90°.

16. The composition of claim 15, wherein the composition comprises the crystal form of the piperazine-1,4-diylbis ((6-(1H-benzo[d]imidazo-2-yl)pyridine-2-yl)methanone) in an amount of 100% w/w of the total amount of crystalized piperazine-1,4-diylbis((6-(1H-benzo[d]imidazo-2-yl)pyridine-2-yl)methanone) present in the composition.

* * * * *